United States Patent [19]

Andrews et al.

[11] Patent Number: 5,708,001
[45] Date of Patent: Jan. 13, 1998

[54] SUBSTITUTED 6-AZAANDROSTENONES

[75] Inventors: Robert Carl Andrews, Durham; Cynthia Markert Cribbs, Raleigh; Stephen Vernon Frye, Durham; Curt Dale Haffner, Cary; Patrick Reed Maloney, Durham, all of N.C.

[73] Assignee: Glaxo Wellcome Inc., Research Triangle Park, N.C.

[21] Appl. No.: 454,166

[22] PCT Filed: Dec. 17, 1993

[86] PCT No.: PCT/US93/12419

§ 371 Date: Jun. 7, 1995

§ 102(e) Date: Jun. 7, 1995

[87] PCT Pub. No.: WO94/14833

PCT Pub. Date: Jul. 7, 1994

[51] Int. Cl.[6] .................. A61K 31/58; C07D 221/18
[52] U.S. Cl. .................. 514/284; 514/213; 514/410; 540/576; 546/61; 548/420
[58] Field of Search ................ 540/576; 546/61; 548/420; 514/410, 213, 284

[56] References Cited

U.S. PATENT DOCUMENTS

| | | | |
|---|---|---|---|
| 4,377,584 | 3/1983 | Rasmusson et al. | 514/284 |
| 5,084,574 | 1/1992 | Bhattacharya et al. | 546/77 |
| 5,302,589 | 4/1994 | Frye et al. | 514/210 |
| 5,438,061 | 8/1995 | Bergman et al. | 514/284 |

FOREIGN PATENT DOCUMENTS

WO93/13124  7/1993  WIPO .

OTHER PUBLICATIONS

Jacobs, T.L. et al, J. Am. Chem. Soc. 1960, pp. 4033–4039.
J.P. Kutney, et al., "Synthesis of Ring A–Oxygenated 6–AZA–Steroids," *Tetrahedron*, 24, No. 2, pp. 845–857, Jan. 1968.

D. Vinod, et al., "Resolution of Conflicting Migratory Reports in Ring Expansion of 3–Keto Steroids to Oxygen and Nitrogen," *Canadian J. of Chem.*, 58, No. 23, pp. 2666–2678, Dec. 1980.

*Primary Examiner*—C. Warren Ivy
*Assistant Examiner*—Garth M. Dahlen
*Attorney, Agent, or Firm*—Robert H. Brink

[57] ABSTRACT

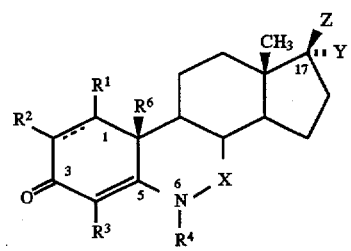

The present invention relates to certain substituted 17β-substituted carbonyl-6-azaandrost-4-en-3-ones of formula (I), wherein $R^1$ and $R^2$ i) are independently hydrogen or lower alkyl and the bond between the carbons bearing $R^1$ and $R^2$ is a single or a double bond, or ii) taken together are a —$CH_2$— group forming a cyclopropane ring, and the bond between the carbons bearing $R^1$ and $R^2$ is a single bond; $R^3$ is preferably hydrogen, halogen or lower alkyl, $R^4$ is preferably hydrogen or lower alkyl, X is preferably $CH_2$, Y is preferably hydrogen and Z is preferably $CONR^{14}R^{15}$ and $R^{14}$ and $R^{15}$ are a variety of organic groups, and pharmaceutically acceptable salts thereof, preparation, medical use and pharmaceutical formulations.

40 Claims, No Drawings

SUBSTITUTED 6-AZAANDROSTENONES

This application is a 371 of PCT/US93/12419 filed Dec. 17, 1993 which claims priority from U.S. Ser. No. 08/080,665 filed 18 Jun. 1992 now abandoned, and U.S. Ser. No. 07/993,930 filed 18 Dec. 1992 now abandoned.

The present invention relates to certain substituted 17β-substituted -6-azaandrost-4-en-3-ones and their use as 5α-testosterone reductase inhibitors.

BACKGROUND OF THE INVENTION

Androgens are responsible for many physiological functions in both males and females. Androgen action is mediated by specific intracellular hormone receptors expressed in androgen responsive cells. Testosterone, the major circulating androgen, is secreted by Leydig cells of the testes under the stimulation of pituitary-derived luteinizing hormone (LH). However, reduction of the 4,5 double bond of testosterone to dihydrotestosterone (DHT) is required in some target tissues, such as prostate and skin, for androgen action. Steroid 5α-reductases in target tissues catalyze conversion of testosterone to DHT in an NADPH dependent fashion as shown in Scheme A.

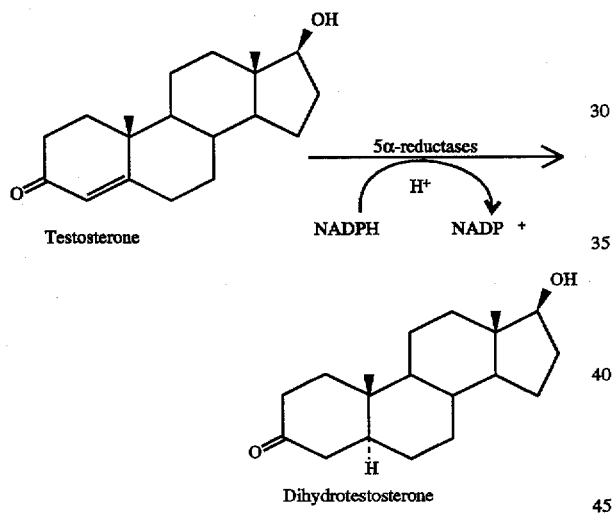

The requirement for DHT to act as an agonist in these target tissues has been highlighted by studies of steroid 5α-reductase deficient individuals who have vestigial prostate glands and do not suffer from acne vulgaris or male pattern baldness (see McGinley, J. et al., *The New England J. of Medicine*, 300, 1233 (1979)). Thus, inhibition of the conversion of testosterone to DHT in these target tissues is anticipated to be useful in the treatment of a variety of androgen responsive diseases, e.g., benign prostatic hyperplasia, prostate cancer, acne, male pattern baldness, and hirsutism.

Additionally, it has recently been discovered that two isozymes of 5α-reductase exist in humans which differ in their tissue distribution, affinity for testosterone, pH profile and sensitivity to inhibitors (see Russell, D. W. et al., *J. Clin. Invest.*, 89, 293 (1992); Russell, D. W. et al., *Nature*, 354, 159 (1991)). The steroid 5α-reductase deficient individuals studied by Imperato-McGinley are deficient in the type 2, 5α-reductase enzyme (Russell, D. W. et al., *J. Clin. Invest.*, 90, 799 (1992); Russell, D. W. et al., *New England J. Med.*, 327, 1216 (1992)), which is the predominant isozyme present in the prostate, while the type 1 isozyme is predominant in the skin. The relative value of isozyme specific and dual inhibitors of the two isozymes of 5α-reductase will depend upon the type of disease treated (benign prostatic hyperplasia, prostate cancer, acne, male pattern baldness, or hirsutism) as well as the stage of the disease (prevention versus treatment) and the anticipated side-effects in the intended patients (for example treatment of acne vulgaris in pubescent males).

Because of their valuable therapeutic potential, testosterone 5α-reductase inhibitors [hereinafter "5α-reductase inhibitors"] have been the subject of active research worldwide. For example, see: Hsia, S. and Voight, W., *J. Invest. Derm.*, 62, 224 (1973); Robaire, B. et al., *J. Steroid Biochem.*, 8, 307 (1977); Petrow, V. et al., *Steroids*, 38, 121 (1981); Liang, T. et al., *J. Steroid Biochem.*, 19, 385 (1983); Holt, D. et al., *J. Med. Chem.*, 33, 937 (1990); U.S. Pat. No. 4,377,584, U.S. Pat. No. 4,760,071 and U.S. Pat. No. 5,017,568. Two particularly promising 5α-reductase inhibitors are MK-906 (Merck), known by the generic name, finasteride, and marketed under the trademark, Proscar; and SKF-105657 (SmithKline Beecham), shown in Scheme B.

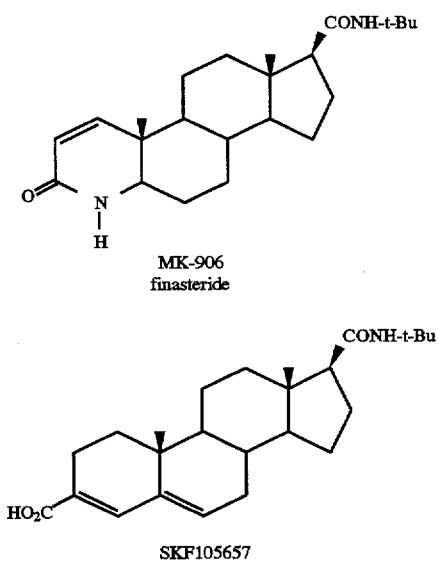

The potent inhibition of bovine adrenal and porcine granulosa cell 3β-hydroxy-Δ$^5$-steroid dehydrogenase/3-keto-Δ$^5$-steroid isomerase (3βHSD) by the 4-azasteroid derivative, 4-MA, shown in Scheme C and not by the drug finasteride (Tan, C. H.; Fong, C. Y.; Chah, W. K. *Biochem. Biophys. Res. Comm.*, 144, 166 (1987) and Brandt, M.; Levy, M. A. *Biochemistry*, 28, 140 (1989)) along with the critical role of 3βHSD in steroid biosynthesis (Potts, G. O. et al., *Steroids*, 32, 257 (1978)), suggests that optimal inhibitors of type 1 and 2 5α-reductase should also be selective versus human adrenal 3βHSD.

SCHEME C

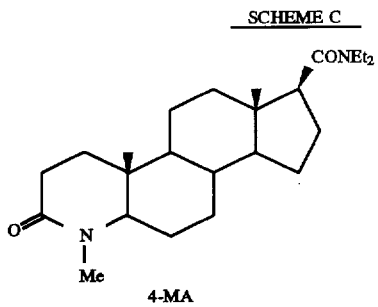

4-MA

The importance of selectivity in 5α-reductase inhibitors has been emphasized by reports of hepatotoxicity in certain 4-azasteroids such as 4-MA (McConnell, J. D. *The Prostate Suppl.*, 3, 49 (1990) and Rasmusson, G. H. et al. *J. Med. Chem.*, 27, 1690 (1984)).

SUMMARY OF THE INVENTION

One aspect of the present invention are the compounds of formula (I),

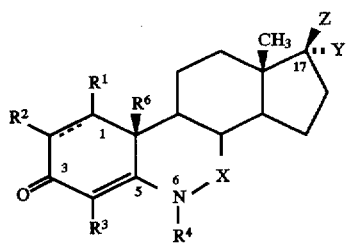

(I)

wherein
$R^1$ and $R^2$
  i) are independently hydrogen or lower alkyl and the bond between the carbons bearing $R^1$ and $R^2$ is a single or a double bond, or
  ii) taken together are a —$CH_2$— group forming a cyclopropane ring, and the bond between the carbons bearing $R^1$ and $R^2$ is a single bond;

$R^3$ is,
  hydrogen, —$Alk^1$—H (optionally substituted with one or more halogens), lower cycloalkyl, lower cycloalkyl-lower alkyl), halogen, —$(Alk^1)_n$—$CO_2H$, —$(Alk^1)_n$—$CO_2R^7$, —$(Alk^1)_n$—$Ar^1$, —$(Alk^1)_n$—$CONR^8R^9$, —$(Alk^1)_n$—$NR^8R^9$, —$(Alk^1)_n$—$S(O)_rR^7$, —$(Alk^1)_n$—$CN$, —$(Alk^1)$—OH, —$(Alk^1)_n$—$COR^7$; or —$(Alk^1)_n$—$OR^7$;
  wherein
  $Alk^1$ is lower alkylene, lower alkenylene or lower alkynylene,
  n is 0 or 1,
  r is 0, 1 or 2,
  $R^7$ is —$Alk^1$—H, —$(Alk^1)_n$—$Ar^1$ or lower cycloalkyl,
  $R^8$ and $R^9$ are independently hydrogen, —$Alk^1$—H or lower cycloalkyl,
  $Ar^1$ is a homocyclic aryl group of 6 to 14 carbons;

$R^4$ is,
  hydrogen, —$Alk^1$—H, lower cycloalkyl, lower cycloalkyl-lower alkyl, —$(Alk^1)_n$—$S(O)_rR^7$, —$(Alk^1)_n$-phthalimidyl, —$(Alk^1)$—$CO_2H$, —$(Alk^1)_n$—$CO_2R^7$, —$(Alk^1)_n$—$COR^7$, —$(Alk^1)_n$—$Ar^1$, —$(Alk^1)_n$—$CONR^8R^9$, —$(Alk^1)_n$—$NR^8R^9$, —$(Alk^1)_n$—OH or —$(Alk^1)_n$—$OR^7$;

X is,

wherein $R^{10}$, $R^{11}$, $R^{12}$ and $R^{13}$ are independently hydrogen or lower alkyl, p and q are independently either 0 or 1; and, i) Y is hydrogen or hydroxy and
Z is —$(Alk^2)_n$—$COR^5$, —$(Alk^2)_n$—$CO_2R^5$, —$(Alk^2)_n$—$COSR^5$, —$(Alk^2)_n$—$CONR^{14}R^{15}$, —$(Alk^2)$—$OCO_2R^5$, —$(Alk^2)$—$OCOR^5$, —$(Alk^2)$—$OCONR^{14}R^{15}$, —$(Alk^2)$—$OR^5$, —$(Alk^2)$—$NR^{5'}COR^5$, —$(Alk^2)$—$NR^{5'}CO_2R^5$, $CO_2R^5$, —$(Alk^2)$—$NR^5CONR^{14}R^{15}$, —$(Alk^2)_n$—$CONR^5NR^{14}R^{15}$, $(Alk^2)_n$—$CONR^5CONR^{14}R^{15}$, —$(Alk^2)$—$NR^5CSNR^{14}R^{15}$ or $(Alk^2)_n$—$CONR^5CSNR^{14}R^{15}$;
wherein $Alk^2$ is ($C_{1-12}$) alkylene, ($C_{2-12}$) alkenylene or ($C_{2-12}$) alkynylene, $R^5$ and $R^{5'}$ are independently hydrogen, —$Alk^1$—H (optionally substituted independently with one or more $CO_2H$, $CO_2R^7$, $Ar^2$, $Ar^3$ or cyano groups) —$(Alk^1)_n$-(lower cycloalkyl (optionally substituted independently with one or more —$Alk^1$—H groups)), adamantyl, norbornyl, $Ar^2$, $Ar^3$, (lower cycloalkyl)-$Ar^2$ or (lower cycloalkyl)-$Ar^3$;
wherein $Ar^2$ is a homocyclic aromatic group of 6 to 14 carbon ring atoms (optionally substituted independently with one or more —$Alk^2$-H (optionally substituted independently with one or more halogens), —$(Alk^1)_n COR^7$, —$(Alk^1)_n$—OH, —$(Alk^1)_n$—$OR^{16}$, —$(Alk^1)_n$—$Ar^3$—$(Alk^1)_n$—$CO_2H$, —$(Alk^1)_n$—$CO_2R^7$, $S(O)_rR^7$, $NR^8S(O)_rR^{16}$, $NR^8R^9$, $CONR^8R^9$, lower cycloalkyl, lower alkoxy, —$(Alk^1)_n$—$Ar^1$ (optionally substituted with one or more —$Alk^1$—H or halogen), methylenedioxy, ethylenedioxy, morpholino, thiomorpholino, cyano, nitro or halogens);
wherein $R^{16}$ is —$Alk^1$—H (optionally substituted independently with one or more halogens), lower cycloalkyl (optionally substituted independently with one or more halogens, or —$Alk^1$—H (optionally substituted independently with one or more halogens)) or —$(Alk^1)_n$—$Ar^1$ (wherein $Ar^1$ is optionally substituted independently with one or more, lower alkoxy, cyano groups, halogens or —$Alk^1$—H (optionally substituted independently with one or more halogens));
$Ar^3$ is an aromatic group of 5 to 14 ring atoms, at least one of which is O, N or S, (optionally substituted independently with one or more —$Alk^1$—H (optionally substituted independently with one or more halogens), lower cycloalkyl, lower alkoxy, $CO_2H$, $CO_2R^7$, —$(Alk^1)_n$—$Ar^1$, cyano or halogen);
$R^{14}$ and $R^{15}$ are,
a) independently, hydroxy, hydrogen, —$Alk^2$- H, lower alkoxy, —$(Alk^1)_n$-adamantyl, —$(Alk^1)_n$-myrantyl, —$(Alk^1)_n$-norbornyl, —$(Alk^1)_n$-fluorenyl, —$(Alk^1)_n$-fluorenonyl, —$(Alk^1)_n$-indanyl (optionally substituted with one or more —$Alk^1$—H), —$Alk^1$—H (optionally substituted independently with one or more, halogens, cyano, cycloalkyl, $SR^5, COR^5, CONR^5R^7, NR^{5'}COR^5$, $NR^{5'}CO_2R^5, NR^{5'}CONHR^5, CO_2R^5, OR^5, Ar^2$ or $Ar^3$), $Ar^2$ or $Ar^3$ or a saturated $C_{4-18}$ bicyclic ring or $C_{3-11}$ saturated ring, optionally containing an oxygen or sulfur atom (said rings optionally substituted independently with one or more cyano, $R^{16}$, $Ar^2$, $Ar^3$);
b) alkylene groups (optionally substituted with one or more $R^7$ groups, taken together with the linking nitrogen to form a 4 to 8 atom heterocyclic group)

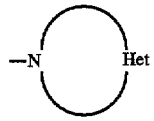

wherein;
Het represents —O—, —C $H_2$—, —S(O)$_r$—, —(NH)—or —(N(Alk$^1$—H))—;
with the proviso that
when Z is —(Alk$^2$)$_n$—COR$^5$, —(Alk$^2$)$_n$—CO$_2$R$^5$ or —(Alk$^2$)$_n$—CO-thiopyridyl and
R$^5$ is hydrogen, —Alk$^1$—H, lower cycloalkyl, or adamantyl or
when Z is —(Alk$^2$)$_n$—CONR$^{14}$R$^{15}$ and
R$^{14}$ and R$^{15}$ are
 a) independently hydrogen, —Alk$^2$-H, lower cycloalkyl, lower alkoxy, adamantyl, -Ar$^1$, benzyl, diphenylmethyl, triphenylmethyl or —(Alk$^1$)$_n$-norbornyl; or
 b) carbon atoms, optionally substituted with one or more lower alkyl groups, taken together with the linking nitrogen to form a 4 to 8 atom heterocylic ring as herein before defined,
Y is hydroxy; or
ii) Y is hydrogen and
Z is OR$^5$, OCOR$^5$, OCONR$^{14}$R$^{15}$, NR$^{5'}$COR$^5$, NR$^{5'}$CO$_2$R$^5$, NR$^5$CONR$^{14}$R$^{15}$ or NR$^5$CSR$^{14}$R$^{15}$; and
iii) Y and Z taken together are
=O, =CH—(Alk$^1$)$_n$—COR$^5$, =CH—(Alk$^1$)$_n$—CO$_2$R$^5$ or
=CH,(Alk$^1$)$_n$—CONR$^{14}$R$^{15}$;
R$^6$ is,
hydrogen or methyl;
and pharmaceutically acceptable salts thereof.
Other aspects of the invention are:
1. A method of inhibiting testosterone-5α-reductases comprising contacting testosterone-5α-reductases with a compound of formula (I).
2. A method of treatment of androgen responsive or mediated disease comprising administering an effective amount of a compound of formula (I) to a patient in need of such treatment.
3. Pharmaceutical formulations containing a compound of formula (I) as an active ingredient. Novel chemical intermediates used in the synthesis, as taught herein, of the compounds of formula (I) are also within the scope of the present invention.
4. A method of treatment of androgen responsive or mediated disease comprising administering an effective amount of a compound of formula (I) to a patient in need of such treatment in combination with an antiandrogen such as flutamide.
5. A method of treatment of benign prostatic hyperplasia comprising administering an effective amount of a compound of formula (I) to a patient in need of such treatment in combination with an alpha 1 adrenergic receptor blocker (e.g. terazosin).
6. A method of treatment of benign prostatic hyperplasia comprising administering an effective amount of a compound of formula (I) to a patient in need of such treatment in combination with an anti-estrogen.

DETAILED DESCRIPTION OF THE INVENTION

As used herein the term "lower" in reference to alkyl and alkoxy means 1–6 carbons, straight or branched chain, e.g., methyl, ethyl, propyl, butyl, pentyl and hexyl; and methoxy, ethoxy, propoxy, butoxy, pentoxy and hexoxy respectively.

In reference to alkenyl or alkynyl "lower" means 2–7 carbons, straight or branched chain e.g., ethenyl, propenyl, butenyl, pentenyl and hexenyl; and ethynyl, propynyl, butynyl, pentynyl and hexynyl respectively. In reference to cycloalkyl "lower" means 3–7 carbons, i.e., cyclopropyl, cyclobutyl, cyclopentyl, cyclohexyl, and cycloheptyl, preferably 3–6 carbons. The term "lower cycloalkyl-lower alkyl" means a lower alkyl bearing a lower cycloalkyl, e.g., cyclopropylmethyl which may also be named methylenecyclopropyl. Preferably "—Alk$^2$-" is the same as "—Alk$^1$".

The term "alkanoyl of 2–6 carbons" refers to alkyl, straight or branched, carboxylic acid groups with a total of 2–6 carbons attached to the structure of formula (I) at a carbon of the alkyl portion of the group, e.g., —CH$_2$COOH, —(CH$_2$)$_2$COOH, —(CH$_2$)$_3$COOH, —(CH$_2$)$_4$COOH and —(CH$_2$)$_5$COOH. The term "halogen" means fluoro, chloro, bromo and iodo moieties. Where —(Alk$^1$)—H is optionally substituted with one or more halogens, the fluoro moiety is preferable, e.g., trifluoromethyl.

The term "aromatic group" includes, but is not limited to, phenyl, napthyl, anthryl, thiophenyl, isothiazolyl, pyrrolyl, imidazolyl, oxazolyl, isoxaolyl, quinolyl, isoquinolyl, indanyl, pyridyl and furyl. The term "aryl" means homocylic aromatic groups having 6 to 14 carbons, e.g., phenyl, naphthyl and anthryl.

Where R$^{14}$ and R$^{15}$ are carbon atoms, optionally substituted with one or more lower alkyl groups, taken together with the linking nitrogen form a 4 to 8 atom heterocyclic group, such groups which may be formed include, but are not limited to, pyrrolidinyl, imidazolidinyl, pyrazolidinyl, piperidinyl, piperazinyl, morpholinyl or thiomorpholinyl each optionally substituted with one or more lower alkyl groups.

Examples of $C_{3-11}$ saturated rings containing an oxygen or sulfur atom include, but are not limited to tetrahydropyran and tetrahydrothiopyran. An example of a saturated $C_{4-18}$ bicyclic ring is bicyclononyl.

Unless specified otherwise, attachment of heteroaromatic or non-aromatic heterocyclic groups containing nitrogen and/or sulfur may be through any carbon or nitrogen. However, if the heterocyclic group is non-aromatic, the preferred position of attachment is through the nitrogen. Further, if the group is a six member, hetero-aromatic ring, attachment through a carbon atom is preferred.

Preferably R$^3$ is hydrogen, halogen, lower alkyl, lower cycloalkyl or lower cycloalkyl-lower alkyl, especially hydrogen, halogen or lower alkyl.

R$^4$ is preferably hydrogen, lower alkyl, lower cycloalkyl or lower cycloalkyl-lower alkyl, especially hydrogen or lower alkyl.

X is preferably —CH$_2$—.

Preferably Y is hydrogen and Z is —(Alk$^2$)$_n$—COR$^5$, —(Alk$^2$)$_n$—CONR$^{14}$R$^{15}$, —(Alk$^2$)—OCO$_2$R$^5$, —(Alk$^2$)—OCOR$^5$, —(Alk$^2$)—NR$^{5'}$COR$^5$, —(Alk$^2$)$_n$—

$CONR^5NR^{14}R^{15}$, —$(Alk^2)$—$NR^5CONR^{14}R^{15}$, or —$(Alk^2)_n$—$CONR^5CONR^{14}R^{15}$, especially —$COR^5$, —$CONR^{14}R^{15}$, —$CH_2OCO_2R^5$, —$CH_2OCOR^5$, —$CH_2NR^{5'}COR^5$, —$CONR^5NR^{14}R^{15}$, —$CH_2NR^5CONR^{14}R^{15}$ or —$CONR^5CONR^{14}R^{15}$.

Compounds wherein Y is hydrogen and Z is —$CONR^{14}R^{15}$ are particularly of interest.

$Ar^1$ is preferably a phenyl group, and $Ar^2$ is preferably a phenyl group optionally substituted independently with one or more —$Alk^2$-H (optionally substituted independently with one or more halogens), —$OR^{16}$, —$S(O)_rR^7$, $Ar^1$, methylenedioxy, ethylenedioxy, morpholino, thiomorpholino, cyano, nitro or halogen groups.

Preferably $R^{14}$ is hydrogen or hydroxy, and $R^{15}$ is hydrogen, lower cycloalkyl (optionally substituted independently with one or more $R^7$ or $Ar^2$ groups), —$(Alk^1)$-adamantyl, —$(Alk^1)_n$-myrantyl, —$(Alk^1)_n$-norbornyl, —$(Alk^1)_n$-fluorenyl, —$(Alk^1)_n$-indanyl, —$Alk^1$—H (optionally substituted independently with one or more lower cycloalkyl, $SR^5$, $OR^5$, $Ar^2$ or $Ar^3$ groups), $Ar^2$ or $Ar^3$; or $R^{14}$ and $R^{15}$ are carbon atoms, optionally substituted with one or more $R^7$ groups, taken together with the linking nitrogen to form a 5 to 7 atom heterocyclic group

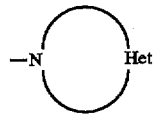

wherein Het represents —$CH_2$—.

Preferably $Ar^3$ is an aromatic group of five or six ring atoms, at least one of which is O, N or S, optionally substituted independently with one or more $Alk^1$ H groups, especially optionally substituted pyrrolyl, thienyl, furyl and pyridyl groups.

$R^5$ is preferably hydrogen, lower alkyl optionally substituted independently with one or more $Ar^2$ groups, (lower alkyl)$_n$-lower cycloalkyl, menthyl, adamantyl, norbornyl or $Ar^2$.

A particular group of the compounds of formula (I) are the compounds wherein:

$R^1$ and $R^2$
  i) are independently hydrogen or lower alkyl and the bond between the carbons bearing $R^1$ and $R^2$ is a single or a double bond, or
  ii) taken together are a —$CH_2$— group forming a cyclopropane ring, and the bond between the carbons bearing $R^1$ and $R^2$ is a single bond;

$R^3$ is,
  hydrogen, —$Alk^1$—H (optionally substituted with one or more halogens), lower cycloalkyl, lower cycloalkyl-lower alkyl), halogen, —$(Alk^1)_n$—$CO_2H$, —$(Alk^1)_n$—$CO_2R^7$, —$(Alk^1)_n$—$Ar^1$, —$(Alk^1)_n$—$CONR^8R^9$, —$(Alk^1)_n$—$NR^8R^9$, —$(Alk^1)_n$—$S(O)_rR^7$, —$(Alk^1)_n$—CN, —$(Alk^1)$—OH, —$(Alk^1)_n$—$COR^7$; or —$(Alk^1)_n$—$OR^7$;
  wherein
  $Alk^1$ is lower alkylene, lower alkenylene or lower alkynylene,
  n is 0 or 1,
  r is 0, 1 or 2,
  $R^7$ is —$Alk^1$—H, —$(Alk^1)_n$—$Ar^1$ or lower cycloalkyl,
  $R^8$ and $R^9$ are independently hydrogen, —$Alk^1$—H or lower cycloalkyl,
  $Ar^1$ is a homocyclic aryl group of 6 to 14 carbons;

$R^4$ is,
  hydrogen, —$Alk^1$—H, lower cycloalkyl, lower cycloalkyl-lower alkyl, —$(Alk^1)_n$—$S(O)_rR^7$, —$(Alk^1)_n$-phthalimidyl, —$(Alk^1)$—$CO_2H$, —$(Alk^1)_n$—$CO_2R^7$, —$(Alk^1)_n$—$COR^7$, -$(Alk1)_n$—$Ar^1$, —$(Alk1)_n$—$CONR^8R^9$, —$(Alk^1)_n$—$NR^8R^9$, —$(Alk^1)_n$—OH or —$(Alk^1)_n$—$OR^7$;

X is,

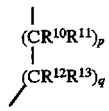

wherein $R^{10}$, $R^{11}$, $R^{12}$ and $R^{13}$ are independently hydrogen or lower alkyl, p and q are independently either 0 or 1; and, i) Y is hydrogen of hydroxy and
Z is —$(Alk^2)_n$—$COR^5$, —$(Alk^2)_n$—$CO_2R^5$, —$(Alk^2)_n$—$COSR^5$, —$(Alk^2)_n$—$CONR^{14}R^{15}$, —$(Alk^2)$—$OCO_2R^5$, —$(Alk^2)$—$OCOR^5$, —$(Alk^2)$—$OCONR^{14}R^{15}$, —$(Alk^2)$—$OR^5$, —$(Alk^2)$—$NR^{5'}COR^5$, —$(Alk^2)$—$NR^{5'}CO_2R^5$, —$(Alk^2)$—$NR^5CONR^{14}R^{15}$, —$(Alk^2)_n$—$CONR^5NR^{14}R^{15}$, —$(Alk^2)_n$—$CONR^5CONR^{14}R^{15}$, —$(Alk^2)$—$NR^5CSNR^{14}R^{15}$ or —$(Alk^2)_n$—$CONR^5CSNR^{14}R^{15}$;
  wherein $Alk^2$ is ($C_{1-12}$) alkylene, ($C_{2-12}$) alkenylene or ($C_{2-12}$) alkynylene, $R^5$ and $R^{5'}$ are independently hydrogen, —$Alk^1$—H (optionally substituted independently with one or more $CO_2H$, $CO_2R^7$, $Ar^2$, $Ar^3$ or cyano groups) —$(Alk^1)_n$-(lower cycloalkyl (optionally substituted independently with one or more —$Alk^1$—H groups)), adamantyl, norbornyl, $Ar^2$, $Ar^3$, (lower cycloalkyl)-$Ar^2$ or (lower cycloalkyl)-$Ar^3$;
  wherein $Ar^2$ is a homocyclic aromatic group of 6 to 14 carbon ring atoms (optionally substituted independently with one or more —$Alk^2$-H (optionally substituted independently with one or more halogens), —$(Alk^1)_n$—OH, —$(Alk^1)_n$—$OR^{16}$, —$(Alk^1)_n$—$Ar^3$, —$(Alk^1)_n$—$CO_2H$, —$(Alk^1)_n$—$CO_2R^7$, $S(O)_rR^7$, $NR^8S(O)_rR^{16}$, $NR^8R^9$, $CONR^8R^9$, lower cycloalkyl, lower alkoxy, —$(Alk^1)_n$—$Ar^1$, methylenedioxy, ethylenedioxy, morpholino, thiomorpholino, cyano, nitro or halogens);
  wherein $R^{16}$ is —$Alk^1$—H (optionally substituted independently with one or more halogens), lower cycloalkyl (optionally substituted independently with one or more halogens, or —$Alk^1$—H (optionally substituted independently with one or more halogens)) or —$(Alk^1)_n$—$Ar^1$ (wherein $Ar^1$ is optionally substituted independently with one or more, lower alkoxy, cyano groups, halogens or —$Alk^1$—H (optionally substituted independently with one or more halogens));
  $Ar^3$ is an aromatic group of 5 to 14 ring atoms, at least one of which is O, N or S, (optionally substituted independently with one or more —$Alk^1$—H (optionally substituted independently with one or more halogens), lower cycloalkyl, lower alkoxy, $CO_2H$, $CO_2R^7$, —$(Alk^1)_n$—$Ar^1$, cyano or halogen);

$R^{14}$ and $R^{15}$ are,
  a) independently, hydroxy, hydrogen, —$Alk^2$- H, lower cycloalkyl (optionally substituted independently with one or more cyano, $R^{16}$, $Ar^2$, $Ar^3$), lower alkoxy, —(Alk$^1$)$_n$-adamantyl, —(Alk$^1$)$_n$-myrantyl, —(Alk$^1$)$_n$-norbornyl, —(Alk$^1$)$_n$-fluorenyl, —(Alk$^1$)$_n$-indanyl, —Alk$^1$—H (optionally substituted independently with one or more, halogens, cyano, cycloalkyl, SR$^5$, COR$^5$, CONR$^5$R$^7$, NR$^5$'COR$^5$, NR$^5$'CO$_2$R$^5$, NR$^5$'CONHR$^5$, CO$_2$R$^5$, OR$^5$, Ar$^2$ or Ar$^3$), Ar$^2$ or Ar$^3$;

b) alkylene groups (optionally substituted with one or more R$^7$ groups, taken together with the linking nitrogen to form a 4 to 8 atom heterocyclic group)

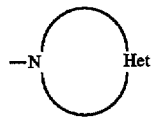

wherein;
Het represents —O—, —CH$_2$—, —S(O)$_r$—, —(NH)— or —(N(Alk$^1$—H))—;

with the proviso that
when Z is —(Alk$^2$)$_n$—COR$^5$, —(Alk$^2$)$_n$—CO$_2$R$^5$ or —(Alk$^2$)$_n$—CO-thiopyridyl and
R$^5$ is hydrogen, —Alk$^1$—H, lower cycloalkyl, —(Alk$^1$)$_n$—Ar$^1$, adamantyl or
when Z is —(Alk$^2$)$_n$—CONR$^{14}$R$^{15}$ and
R$^{14}$ and R$^{15}$ are
  a) independently hydrogen, —Alk$^2$-H, lower cycloalkyl, lower alkoxy, adamantyl, -Ar$^1$, benzyl, diphenylmethyl, triphenylmethyl or —(Alk$^1$)$_n$-norbornyl; or
  b) carbon atoms, optionally substituted with one or more lower alkyl groups, taken together with the linking nitrogen to form a 4 to 8 atom heterocylic ring as herein before defined,
Y is hydroxy; or
ii) Y is hydrogen and
Z is OR$^5$, OCOR$^5$, OCONR$^{14}$R$^{15}$, NR$^5$'COR$^5$, NR$^5$'CO$_2$R$^5$, NR$^5$CONR$^{14}$R$^{15}$ or NR$^5$CSR$^{14}$R$^{15}$; and
iii) Y and Z taken together are
=O, =CH—(Alk$^1$)$_n$—COR$^5$, =CH—(Alk$^1$)$_n$—CO$_2$R$^5$ or
=CH—(Alk$^1$)$_n$—CONR$^{14}$R$^{15}$;
R$^6$ is,
hydrogen or methyl;
and pharmaceutically acceptable salts thereof.
A subgroup of the compounds of formula (I) are the compounds wherein:
R$^1$ and R$^2$ are,
i) independently hydrogen or lower alkyl and the bond between the carbons bearing R$^1$ and R$^2$ is a single or a double bond, or
ii) taken together are a —CH$_2$— group to form a cyclopropane ring, and the bond between the carbons bearing R$^1$ and R$^2$ is a single bond;
R$^3$ is hydrogen, —Alk$^1$—H, —Alk$^1$—H substituted with one or more halogens, lower cycloalkyl, lower cycloalkyl-lower alkyl, halogen, —(Alk$^1$)$_n$—CO$_2$H, —(Alk$^1$)$_n$—CO$_2$R$^7$, —(Alk$^1$)$_n$—Ar$^1$, —(Alk$^1$)$_n$—CONR$^8$R$^9$, —(Alk$^1$)$_n$—NR$^8$R$^9$, —(Alk$^1$)$_n$—S(O)$_r$R$^7$, —(Alk$^1$)$_n$—CN, —(Alk$^1$)—OH or —(Alk$^1$)$_n$—OR$^7$;
wherein
Alk$^1$ is lower alkylene, lower alkenylene or lower alkynylene,
n is 0 or 1,
r is 0, 1 or 2, R$^7$ is —Alk$^1$—H, —(Alk$^1$)$_n$—Ar$^1$ or lower cycloalkyl,
R$^8$ and R$^9$ are independently hydrogen, —Alk$^1$—H or lower cycloalkyl,
Ar$^1$ is a homocyclic aryl group of 6 to 14 carbons;
R$^4$ is hydrogen, —Alk$^1$—H, lower cycloalkyl, lower cycloalkyl-lower alkyl, —(Alk$^1$)$_n$—S(O)$_r$R$^7$, —(Alk$^1$)$_n$-phthalimidyl, (—Alk$^1$—)CO$_2$H, —(Alk$^1$)$_n$—CO$_2$R$^7$, —(Alk$^1$)$_n$—Ar$^1$, —(Alk$^1$)$_n$—CONR$^8$R$^9$, —(Alk$^1$)$_n$—NR$^8$R$^9$, —(Alk$^1$)$_n$—OH or —(Alk$^1$)$_n$—OR$^7$;

X is,

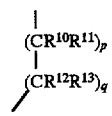

wherein R$^{10}$, R$^{11}$, R$^{12}$ and R$^{13}$ are independently hydrogen or lower alkyl, p and q are independently either 0 or 1;

Y and Z are,
i) Y is hydrogen or hydroxy and
Z is —(Alk$^2$)$_n$—COR$^5$, —(Alk$^2$)$_n$—CO$_2$R$^5$, —(Alk$^2$)$_n$—COSR$^5$, —(Alk$^2$)$_n$—CONR$^{14}$R$^{15}$, —(Alk$^2$)—OCOR$^5$, —(Alk$^2$)—OCONR$^{14}$R$^{15}$, —(Alk$^2$)—OR$^5$, —(Alk$^2$)—NR$^5$COR$^5$, —(Alk$^2$)—NR$^5$CO$_2$R$^5$, —(Alk$^2$)—NR$^5$CONR$^{14}$R$^{15}$, (Alk$^2$)—$_n$CONR$^5$NR$^{14}$R$^{15}$, —(Alk$^2$)$_n$—CONR$^5$CONR$^{14}$R$^{15}$, (—Alk$^2$-)NR$^5$CSNR$^{14}$R$^{15}$ or —(Alk$^2$)$_n$—CONR$^5$CSNR$^{14}$R$^{15}$;
wherein
Alk$^2$ is (C$_{1-12}$) alkylene, (C$_{2-12}$) alkenylene or (C$_{2-12}$ alkynylene, R$^5$ is hydrogen, —Alk$^1$—H, —(Alk$^1$)$_n$-(lower cycloalkyl), adamantyl, —(Alk$^1$)$_n$—Ar$^2$, —(Alk$^1$)$_n$—Ar$^3$, (lower cycloalkyl)$_n$Ar$^2$, (lower cycloalkyl)$_n$Ar$^3$ or —Alk$^1$-substituted independently with one or more CO$_2$H, CO$_2$R$^7$, Ar$^2$ or Ar$^3$ groups;
wherein Ar$^2$ is an aromatic group of 6 to 14 carbon ring atoms, optionally substituted with one or more Alk$^1$, Alk$^1$ substituted with one or more halogens, —(Alk$^1$)$_n$—OH, —(Alk$^1$)$_n$—OR$^7$, —(Alk$^1$)$_n$—CO$_2$H, —(Alk$^1$)$_n$—CO$_2$R$^7$, S(O)$_r$R$^7$ or NR$^8$R$^9$, lower cycloalkyl, lower alkoxy, —(Alk$^1$)$_n$-Ar$^1$, methylenedioxy, ethylenedioxy, morpholino, thiomorpholino, cyano or halogen groups;
Ar$^3$ is an aromatic group of 5 to 14 ring atoms, at least one of which is O, N or S, optionally substituted with one or more Alk$^1$, lower cycloalkyl, lower alkoxy, CO$_2$H, CO$_2$R$^7$, —(Alk$^1$)$_n$—Ar$^1$, cyano or halogen groups;
R$^{14}$ and R$^{15}$ are,
  a) independently, hydrogen or —Alk$^2$-H, lower cycloalkyl, lower alkoxy, adamantyl, —(Alk$^1$)$_n$-norbornyl, Ar$^2$, Ar$^3$, —Alk$^1$-substituted independently with one or more, SR$^5$, COR$^5$, CONR$^5$R$^7$, NR$^5$COR$^5$, NR$^5$CO$_2$R$^5$, NR$^5$CONHR$^5$ CO$_2$R$^5$, OR$^5$, Ar$^2$ or Ar$^3$ groups, —(Alk$^1$)$_n$-fluorenyl or —(Alk$^1$)$_n$-indanyl; or
  b) carbon atoms, optionally substituted with one or more lower alkyl groups, taken together with the linking nitrogen to form a 4 to 8 atom heterocyclic group

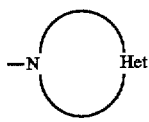

wherein;
Her represents —O—, —CH$_2$—, —S(O)$_r$—, —(NH)— or —(N(Alk$^1$))—;
with the proviso that
when Z is (—Alk$^2$-)$_n$COR$^5$, (—Alk$^2$-)$_n$CO$_2$R$^5$ or —(Alk$^2$)$_n$—CO-thiopyridyl and R$^5$ is hydrogen, —Alk$^1$-H, lower cycloalkyl, —(Alk$^1$)$_n$—Ar$^1$, adamantyl or when Z is (—Alk$^2$-)$_n$CONR$^{14}$R$^{15}$ and R$^{14}$ and R$^{15}$ are
(a) independently hydrogen, —Alk$^2$-H, lower cycloalkyl, lower alkoxy, adamantyl, -Ar$^1$, benzyl, diphenylmethyl, triphenylmethyl or —(Alk$^1$)$_n$-norbornyl; or
(b) carbon atoms, optionally substituted with one or more lower alkyl groups, taken together with the linking nitrogen to form a 4 to 8 atom heterocylic ring as herein before defined, Y is hydroxy;
ii) Y is hydrogen and
Z is OR$^5$, OCOR$^5$, OCONR$^{14}$R$^{15}$, NR$^5$COR$^5$NR$^5$CO$_2$R$^5$, NR$^5$CONR$^{14}$R$^{15}$ or NR$^5$CSR$^{14}$R$^{15}$;
iii) Y and Z taken together are =O, =CH—(Alk$^1$)$_n$—COR$^5$, =CH—(Alk$^1$)$_n$—CO$_2$R$^5$ or =CH—(Alk$^1$)$_n$—CONR$^{14}$R$^{15}$;
R$^6$ is hydrogen or methyl;
and pharmaceutically acceptable salts thereof.

Particular groups of compounds of formula (I) are the compounds of formulas (IA), (IB), (IC) and (ID)

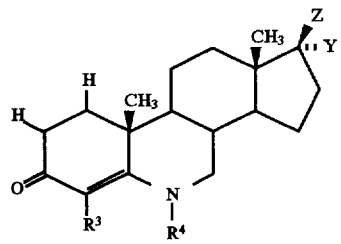
(IA)

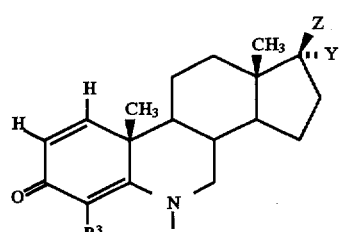
(IB)

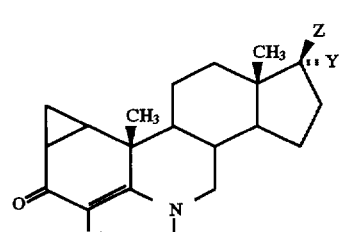
(IC)

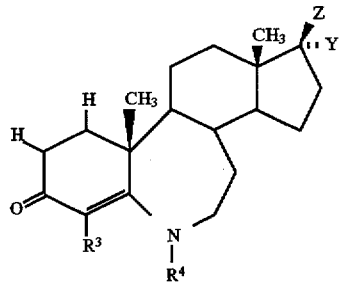
(ID)

Compounds of formula (IA) are especially of interest.
In an alternative aspect the invention provides compounds of formula (I) wherein Z is -COR$^5$ including:
17β-(1-Oxo-2-cyclohexylethyl)-6-azaandrost-4-en-3-one
17β-(1-Oxo-1-(2,4-difluorophenyl)methyl)-6-azaandrost-4-en-3-one
17β-(1-Oxo-1-(4-isopropoxyphenyl)methyl)-6-azaandrost-4-en-3-one
17β-(1-Oxo-3,3-diphenylpropyl)-6-azaandrost-4-en-3-one
17β-(1-Oxo-1-(2-norbornyl)methyl)-6-azaandrost-4-en-3-one A particular aspect of the invention provides compounds of formula (I) wherein Z is —CONR$^{14}$R$^{15}$, R$^{14}$ is hydrogen and R$^{15}$ is Ar$^2$ or C$_{3-11}$ saturated ring, optionally containing an oxygen or a sulfur atom, (optionally substituted independently with one or more R$^7$ or Ar$^2$ groups). Preferably R$^{15}$ is a group of formula Ar$^{2a}$

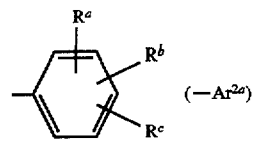
(—Ar$^{2a}$)

wherein R$^a$ and R$^b$ are independently hydrogen, lower alkyl, trifluoromethyl, halogen or phenyl (optionally substituted with one or more halogens or branched C$_{4-7}$ alkyl) and R$^c$ is hydrogen or one or more halogens, or R$^{15}$ is a C$_{3-11}$ saturated ring, optionally containing an oxygen or a sulfur atom, substituted with a group of formula Ar$^{2a}$. In a particular group of compounds Ar$^{2a}$ is a group of formula Ar$^{2aa}$

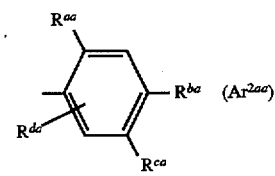
(Ar$^{2aa}$)

where R$^{aa}$ is branched C$_{4-7}$ alkyl, trifluoromethyl or phenyl optionally substituted with one or more halogens; one of R$^{ba}$ and R$^{ca}$ is branched C$_{4-7}$alkyl, trifluoromethyl, halogen or phenyl optionally substituted with one or more halogens, and the other is hydrogen or halogen; and R$^{da}$ is hydrogen or halogen.

Particular compounds of the invention include:
17β-N-((2,6-Di-i-propyl)phenyl)-carbamoyl-6-azaandrost-4-en-3-one
17β-N-(2,4,6-trimethyl)phenyl-carbamoyl-6-azaandrost-4-en-3-one
17β-N-(2-Chloro-5-trifluoromethyl)phenyl-carbamoyl-6-azaandrost-4-en-3-one 17β-N-(2,6-Dimethyl-4-bromo)phenyl-carbamoyl-6-azaandrost-4-en-3-one 17β-N-(2,6-Dimethyl-4-t-butyl)phenyl-carbamoyl-6-azaandrost-4-en-3-one 17β-N-(2,6-Dibromo-4-isopropyl)phenyl-carbamoyl-6-azaandrost-4-en-3-one 17β-N-(2,5-Ditrifluoromethyl)phenyl-carbamoyl-6-azaandrost-4-en-3-one 17β-N-(2-Phenyl)phenyl-carbamoyl-6-azaandrost-4-en-3-one 17β-N-(2,6-Diethyl-3,5-dichloro)phenyl-carbamoyl-6-azaandrost-4-en-3-one 17β-N-(2,6-Diethyl-3-chloro)phenyl-carbamoyl-6-azaandrost-4-en-3-one 17β-N-(2-t-Butyl)phenyl-carbamoyl-6-azaandrost-4-en-3-one 17β-N-(2,4,6-Trichloro)phenyl-carbamoyl-6-azaandrost-4-en-3-one 17β-N-(2-Bromo-5-trifluoromethyl)phenyl-carbamoyl-6-azaandrost-4-en-3-one 17β-N-(2-t-Butyl-6-methyl)phenyl-carbamoyl-6-azaandrost-4-en-3-one 17β-N-(4-Chlorophenyl)cyclopentyl-carbamoyl-6-azaandrost-4-en-3-one 17β-N-(2,6-Dibromo-4-chloro)phenyl-carbamoyl-6-azaandrost-4-en-3-one 17β-N-(2,6-Diethyl-4-bromo)phenyl-carbamoyl-6-azaandrost-4-en-3-one 17β-N-(2-Bromo-4-t-butyl)phenyl-carbamoyl-6-azaandrost-4-en-3-one 17β-N-(2-Chloro-4-t-butyl)phenyl-carbamoyl-6-azaandrost-4-en-3-one 17β-N-(5-Bromo-2-t-butyl)phenyl-carbamoyl-6-azaandrost-4-en-3-one 17β-N-(5-Chloro-2-t-butyl)phenyl-carbamoyl-6-azaandrost-4-en-3-one 17β-N-(2,6-Diethyl)phenyl-carbamoyl-6-azaandrost-4-en-3-one 17β-N-(4-Bromo-2-t-butyl)phenyl-carbamoyl-6-azaandrost-4-en-3-one 17β-N-(2-t-Butyl-5-cyano)phenyl-carbamoyl-6-azaandrost-4-en-3-one 17β-N-(2-(O-4-Tolyl)-5-trifluoromethyl)phenyl-carbamoyl-6-azaandrost-4-en-3-one 17β-N-(2-(O-4-Chlorophenyl)-5-trifluoromethyl)phenyl-carbamoyl-6-azaandrost-4-en-3-one 17β-N-(2-Nitro-4-t-butyl)phenyl-carbamoyl-6-azaandrost-4-en-3-one 17β-N-(2-(O-Phenyl)-5-(1,1-dimethyl)propyl)phenyl-carbamoyl-6-azaandrost-4-en-3one 17β-N-(2-Ethylsulfonyl-5-trifluoromethyl)phenyl-carbamoyl-6-azaandrost-4-en-3-one 17β-N-(3,5-Di-t-butyl)phenyl-carbamoyl-6-azaandrost-4-en-3-one 17β-N-(2-t-Butyl)-5-trifluoromethyl)phenyl-carbamoyl-6-azaandrost-4-en-3-one 17β-N-(2-t-Butyl-5-phenyl)phenyl-carbamoyl-6-azaandrost-4-en-3-one 17β-N-(2,6-Di-i-propyl)phenyl-carbamoyl-6-azaandrost-1,4-dien-3-one 17β-N-(2,6-Di-i-propyl)phenyl-carbamoyl-6-azaandrost-4-methyl-1,4-dien-3-one 17β-N-(4-Trifluoromethylphenyl)cyclopentyl-carbamoyl-6-azaandrost-4-en-3-one 17β-N-(4-Fluorophenyl)cyclohexyl-carbamoyl-6-azaandrost-4-en-3-one 17β-N-(4-Methoxyphenyl)cyclohexyl-carbamoyl-6-azaandrost-4-en-3-one 17β-N-(4-Methoxyphenyl)cyclopentyl-carbamoyl-6-azaandrost-4-en-3-one 17β-N-(2,5-bis(Trifluoromethyl))phenyl-carbamoyl-6-azaandrost-4-methyl-4-en-3-one 17β-N-(2-t-Butyl-5-trifluoromethyl)phenyl-carbamoyl-6-azaandrost-4-methyl-4-en-3-one 17β-N-(2,5-Di-t-butyl)phenyl-carbamoyl-6-azaandrost-4-methyl-4-en-3-one 17β-N-(2-t-Butyl-5-(4-chlorophenyl))phenyl-carbamoyl-6-azaandrost-4-en-3-one 17β-N-1-(4-t-Butylphenyl)cyclopentyl-carbamoyl-6-azaandrost-4-en-3-one 17β-N-1-(4-t-Butylphenyl)cyclohexyl-carbamoyl-6-azaandrost-4-en-3-one 17β-N-1-(4-Chlorophenyl)cyclopentyl-carbamoyl-6-azaandrost-4-methyl-4-en-3-one 17β-N-(2,5-bis(Trifluoromethyl))phenyl-carbamoyl-6-azaandrost-4-chloro-4-en-3-one 17β-N-(2-t-Butyl-5-trifluoromethyl)phenyl-carbamoyl-6-azaandrost-4-chloro-4-en-3-one 17β-N-1-(4-t-Butylphenyl)cycloheptyl-carbamoyl-6-azaandrost-4-en-3-one 17β-N-1-(4-t-Butylphenyl) cyclohexyl-carbamoyl-6-azaandrost-4-chloro-4-en-3-one 17β-N-(2,6-Diethyl-4-(4-chlorophenyl))phenyl-carbamoyl-6-azaandrost-4-en-3-one 17β-N-4-(4-t-Butylphenyl)tetrahydrothiopyranyl-carbamoyl-6-azaandrost-4-en-3-one 17β-N-9-(4-t-Butylphenyl)bicyclo[3.3.1]nonyl-carbamoyl-6-azaandrost-4-en-3-one 17β-N-4-(4-t-Butylphenyl)tetrahydropyranyl-carbamoyl-6-azaandrost-4-en-3-one 17β-N-1-(4-Chlorophenyl)cyclohexyl-carbamoyl-6-azaandrost-4-en-3-one 17β-N-(2-t-Butyl-5-(4-t-butyl)phenyl)phenyl-carbamoyl-6-azaandrost-4-en-3-one or 17β-N-1-(4-Chlorophenyl)cyclopentyl-carbamoyl-6-azaandrost-4-chloro-4-en-en-3-one and pharmaceutically acceptable salts thereof.

A particular compound is 17β-N-(2-t-Butyl-5-trifluoromethyl)phenyl-carbamoyl-6-azaandrost-4-en-3-one and pharmaceutically acceptable salts thereof.

One particular aspect of the invention provides compounds of formula (I) wherein $R^1$ and $R^2$ are as hereinbefore defined, $R^3$ is hydrogen or lower alkyl;

$R^4$ is hydrogen or lower alkyl;

Y is hydrogen; and

Z is $-COR^5$, $-CONR^{14}R^{15}$, $-CH_2OCO_2R^5$, $-CH_2OCOR^5$, $-CH_2NR^{5'}COR^5$, $-CONR^5NR^{14}R^{15}$, $-CH_2NR^5CONR^{14}R^5$, or $-CON^5CONR^{14}R^{15}$ wherein $R^5$ and $R^{5'}$ are independently hydrogen, lower alkyl optionally substituted independently with one or more $Ar^2$ groups (lower alkyl)$_n$-lower cycloalkyl, menthyl, adamantyl, norbornyl or $Ar^2$;

$Ar^2$ is a phenyl group optionally substituted independently with one or more —Alk-H (optionally substituted independently with one or more halogens), —$OR^{16}$, —$S(O)_rR^7$, phenyl, methylenedioxy, ethylenedioxy, morpholino, thiomorpholino, cyano, nitro or halogen groups;

Alk is lower alkylene, lower alkenylene or lower alkynylene;

n is 0 or 1;

r is 0, 1 or 2;

$R^7$ is —Alk-H, —(Alk)$_n$-phenyl or lower cycloalkyl;

$R^{16}$ is —Alk-H (optionally substituted independently with one or more halogens), lower cycloalkyl (optionally substituted independently with one or more halogens or —Alk-H (optionally substituted independently with one or more halogens)) or —(Alk)$_n$-phenyl (wherein phenyl is optionally substituted independently with one or more lower alkoxy, cyano, halogen or —Alk-H groups (optionally substituted independently with one or more halogens)); $R^{14}$ is hydrogen or hydroxy, and $R^{15}$ is hydrogen, lower cycloalkyl (optionally substituted independently with one or more $R^7$ or $Ar^2$ groups), —(Alk)-adamantyl, —(Alk)$_n$-myrantyl, —(Alk)$_n$-norbornyl, —(Alk)$_n$-fluorenyl, —(Alk)$_n$-indanyl, —Alk-H (optionally substituted independently with one or more lower cycloalkyl, $SR^5$, $OR^5$, $Ar^2$ or $Ar^3$ groups), $Ar^2$ or $Ar^3$, or $R^{14}$ and $R^{15}$ taken together with the linking nitrogen form a pyrrolidinyl, piperidinyl or perhydroazepinyl ring optionally substituted with one or more $R^7$ groups; $Ar^3$ is a pyrrolyl, thienyl, furyl or pyridyl group optionally substituted independently with one or more Alk-H groups; with the provisos that when Z is $COR^5$, $R^5$ is substituted lower alkyl, lower alkyl lower cycloalkyl, menthyl, norbornyl or $Ar^2$;

when Z is $CONR^{14}R^{15}$ and $R^{15}$ is hydrogen, —Alk-H, lower cycloalkyl, lower alkoxy, adamantyl, phenyl, benzyl, diphenylmethyl, triphenylmethyl or —(Alk)$_n$-norbornyl, $R^{14}$ is hydroxy; and when Z is $CONR^{14}R^{15}$ and $R^{14}$ and $R^{15}$ taken together with the linking nitrogen form a pyrrolidinyl, piperidinyl or perhydroazepinyl ring, said ring is substituted with one or more lower alkenyl, lower alkynyl, —(Alk)$_n$-phenyl or lower cycloalkyl groups; and pharmaceutically acceptable salts thereof. Compounds of formula (IA) are especially of interest. In a still further aspect of the invention of partiucalr interest, Z is $CONR^{14}R^{15}$.

Some of the substituents of the compound of formula (I) may cause asymmetry about the atoms to which they are attached giving rise to either α or β stereochemical configuration. (For a detailed explanation of stereochemical configuration see March, *J. Advanced Organic Chemistry*, 3rd Ed., ch 4, John Wiley & Sons, New York (1985).) Unless otherwise indicated, either the α and β stereo configurations are intended for the substituents.

The compounds of formula (I) can be used in the form of an acid addition salt derived from inorganic or organic acids. Where the salt of a compound of formula (I) is to be used for a human or veterinary medicinal application the salt must be pharmaceutically acceptable. However, non-pharmaceutically acceptable salts of the compounds of formula (I) may be useful as intermediates in the preparation of a corresponding pharmaceutically acceptable salt. Pharmaceutically acceptable salts include, but are not limited to, salts with inorganic acids such as hydrochloride, sulfate, phosphate, diphosphate, hydrobromide and nitrate salts or salts with an organic acid such as the acetate, malate, maleate, fumarate, tartrate, succinate, citrate, lactate, methanesulfonate, p-toluenesulfonate, palmitoate, salicylate and stearate salts.

Preparation of Compounds

According to one general process (A) the compounds of the present invention may be prepared by the procedure shown in step 8 of Scheme I, wherein $R^1$-$R^4$, $R^6$, Y and Z are as defined for formula (I) and "JO" is a protected hydroxy group:

SCHEME I

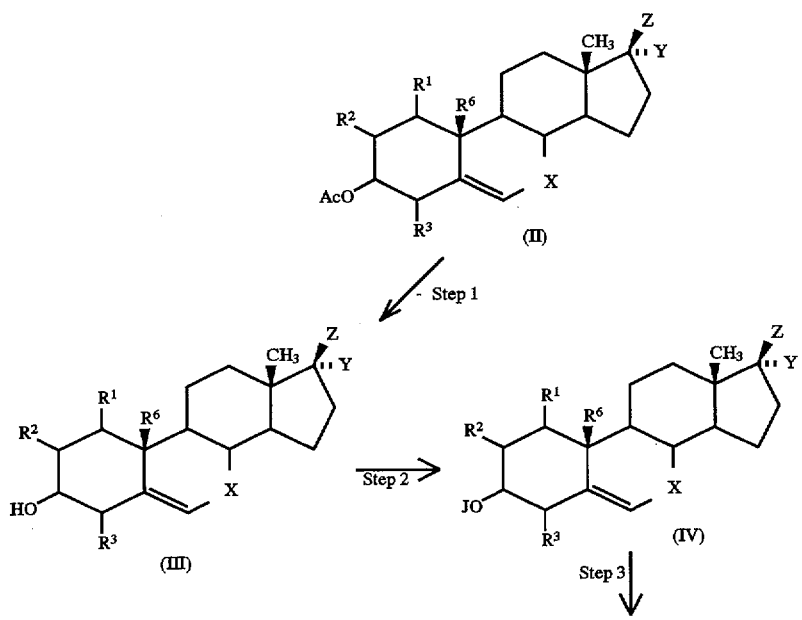

-continued
SCHEME I

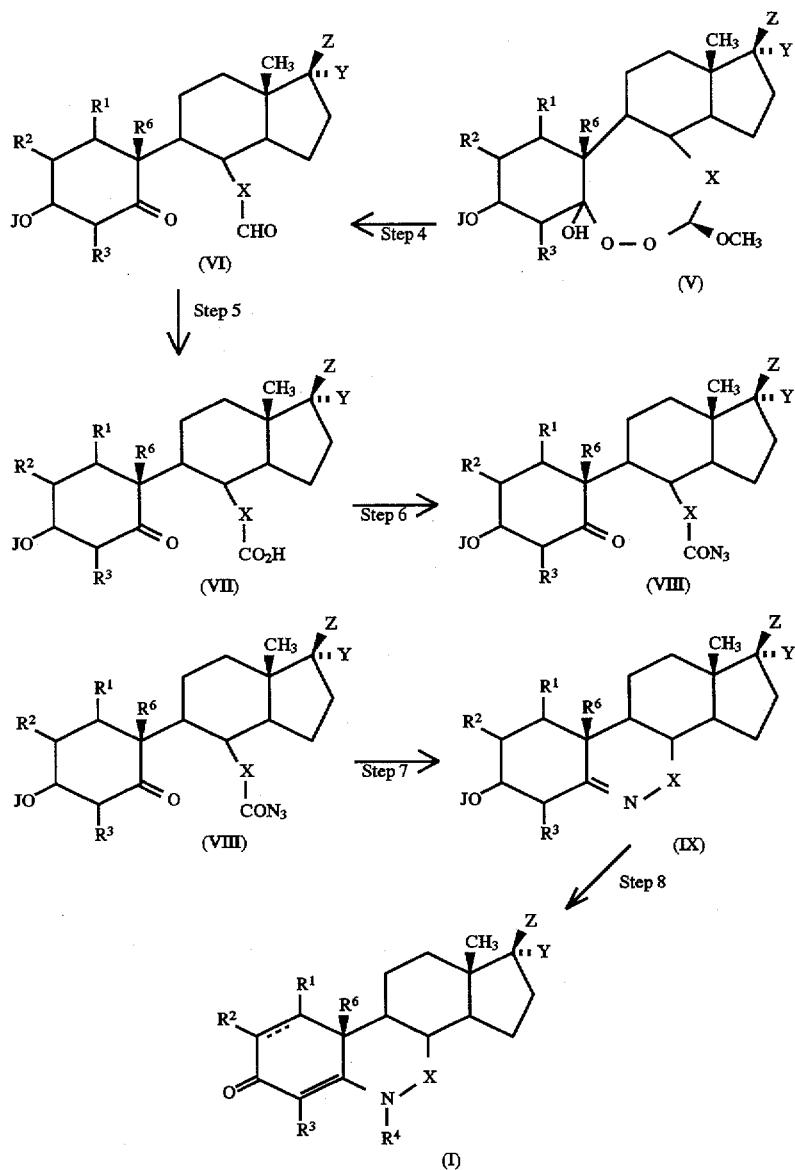

In Step 1 of Scheme I when Z is $CO_2H$, the acid group at the 17 position of a compound of formula (II) is converted to the corresponding ketone, ester or amide of compound (III) accompanied by deprotection of the hydroxy group at the 3 position. Alternatively a compound of formula (III) wherein Z is $CO_2CH_3$ and Y is H may be prepared from pregnenolone as described by Rasmusson, et al., *J. Med. Chem.*, 27, 1690 (1984).

This may be accomplished by activating the carboxylic acid group toward nucleophilic displacement by treatment with an activating agent such as N,N-bis(2-oxo-3-oxazolidinyl)phosphorinic chloride (BOP-Cl) or conversion to the corresponding acid halide group by treatment with a halogenating agent such as oxalyl chloride or thionyl chloride in an aprotic solvent such methylene chloride or toluene at −5 to 10° C. The intermediate activated carboxylic acid, e.g., an acid chloride, may be reacted with H—$NR^{14}R^{15}$ or HO$R^5$ (wherein $R^5$, $R^{14}$ and $R^{15}$ are as defined for formula (I)) at or above room temperature in an aprotic solvent.

When $R^5$ is alkyl, alkenyl, lower cycloalkyl, or adamantyl, the activated acid is treated with $R^5M$ (wherein M is a metal, such as magnesium or lithium) in a polar, aprotic solvent such as THF or diethyl ether containing catalytic CuI, at a temperature in the range of about 0 ° to about −78° C.

Additionally, when, H—$NR^{14}R^{15}$ is a hindered, nonnucleophilic aniline the corresponding metal salt may be prepared and the activated acid treated with M—$NR^{14}R^{15}$ (wherein M is a metal, such as magnesium or lithium) in a polar, aprotic solvent such as THF or diethyl ether at a temperature in the range of about 0° to about −78° C.

The amines, H—$NR^{14}R^{15}$ are commercially available or conveniently prepared by methods known in the art. For example, when either $R^{14}$ or $R^{15}$ is an alkyl or aryl substituted aromatic residue the alkyl group may be introduced as described by Reetz, M. T. et al., *Angew. Chem. Int. Ed. Engl.*, 19, 900 and 901 (1980) or the aryl group introduced as described by Stille, J. K. *Pure Appl. Chem.*, 57, 1771 (1985).

When either $R^{14}$ or $R^{15}$ is an aryl substituted cycloalkyl residue the amine may be prepared by Curtius rearrangement of the corresponding acid, where available, or by the method of He, X. et al., *J. Med. Chem.*, 36, 1188 (1993), i.e. by reacting the corresponding cycloalkanone with the appropriate aryl Grignard reagent followed by conversion of the resulting alcohol to the amine by treatment with sodium azide and trifluoroacetic acid followed by reduction of the azide with lithium aluminum hydride. Aryl substituted cyclopropylamines are prepared by rhodium catalyzed insertion of the appropriate aryl-α-diazo-ester (prepared by the method of Baum, J. S. et al., *Synthetic Comm.*, 17, 1709 (1987)) into the appropriate olefin (as described by Davies, H. W. et al, *Tetrahedron Lett.*, 30, 5057 (1989)) followed by saponification of the ester and Curtius rearrangement of the acid to give the desired amine.

In Step 2, a compound of formula (III) is treated with a suitable hydroxy protecting group such as for example a silicon derivative such as a trisubstituted silyl halide, a tetrahydropyran derivative or an arylalkyl group such as a paramethoxybenzyl group. Typically the compound of formula (III) is treated with a trialkylsilyl halide, e.g., triisopropylsilyl chloride, at about 25° to 75° C. in an aprotic solvent such as dimethylformamide to protect the hydroxy group in the 3-position to yield the corresponding trisubstituted silylated compound of formula (IV).

In Step 3, a compound of formula (IV) is treated with ozone in methanol alone or as a mixture with one or more polar, protic or aprotic solvents, e.g., methylene chloride and methanol, at a temperature substantially below 0° C., e.g., from about −50° to about −80° C. to yield a corresponding compound of formula (V).

In Step 4, the compound of formula (V) in methanol alone or as a mixture with one or more polar, protic or aprotic solvents, e.g., methylene chloride and methanol, at about −20° C. is treated with a reductant such as zinc and acetic acid then allowed to slowly warm to room temperature to yield the aldehyde of formula (VI). Alternatively the compound of formula (V) may be taken directly to step 5.

In Step 5, a compound of formula (V or VI) is reacted with an oxidant, such as Jones reagent (see Bowden, et al., *J. Chem. Soc.*, 39, (1946)) at about 0° C., to yield the corresponding compound of formula (VII).

In Step 6, a compound of formula (VII) is converted to an activated carboxylate derivative such as an acid halide, e.g., chloride, by treatment with a halogenating agent, e.g., oxalyl chloride. The resulting acid halide is reacted with an alkali metal azide, e.g., sodium azide, at about 0° to 30° C. in an aqueous solvent mixture, such as water and acetone, to yield the corresponding acyl azide compound of formula (VIII). Alternatively, the acid is treated with triphenyl phosphoryl azide in an aprotic solvent such as toluene to yield the acyl azide directly.

In Step 7, an acyl azide compound of formula (VIII) is rearranged with ring closure by warming to reflux in an aprotic solvent, such as toluene, to induce rearrangment to the corresponding isocyanate followed by stirring with a weak acid such as silica gel or by reaction with a strong, sterically hindered base, e.g., potassium t-butoxide, in a protic or aprotic solvent at a temperature in the range of about 90° to about 180° C. to generate the corresponding compound of formula (IX).

Finally, in Step 8 (general process A), the hydroxy function of a compound of formula (IX) is deprotected and oxidized. Thus, in general process (A1) compounds of formula (I) wherein $R^4$ is hydrogen may be prepared by converting the protected hydroxy group of a compound of formula (IX) to the corresponding hydroxy group, i.e., the hydroxy group is deprotected by conventional means. Thus, for example a trisubstituted silyl group may be removed by reaction with aqueous hydrogen fluoride in a polar solvent such as acetonitrile at about 0° C. to room temperature. Next the hydroxy group is oxidized by reaction with a suitable oxidizing agent, for example, with Jones reagent with migration of the double bond to the 4,5 position to generate the corresponding compound of formula (I) where $R^4$ is hydrogen.

Alternatively, in general process (A2) for the preparation of compounds of formula (I), wherein $R^4$ is an acyl group, the compound of formula (IX) is treated with an acylating agent such as di-t-butyldicarbonate to acylate the 6-nitrogen with migration of the double bond to the 4, 5 position. The hydroxy protecting group is then removed in a conventional manner, for example, a trisubstituted silyl protecting group may be removed with a reagent such as tetrabutylammonium fluoride and treated with an oxidant such as pyridinium dichromate or manganese dioxide to generate the corresponding compound of formula (I) where $R^4$ is t-butoxycarbonyl.

Alternatively, intermediate compounds of formula (IX) may be prepared from the corresponding compounds of formula (VII) according to Scheme 1A.

SCHEME 1A

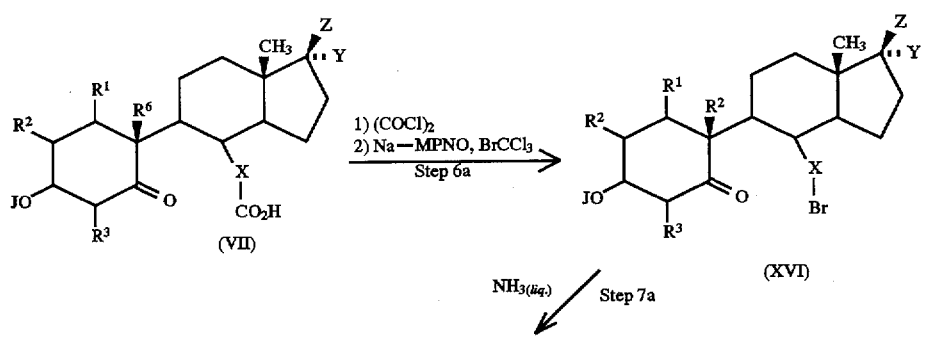

-continued
SCHEME 1A

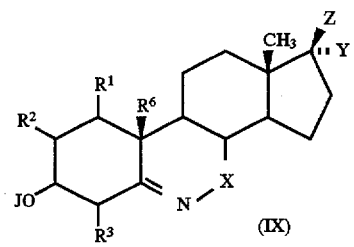

(IX)

In step 6a of Scheme 1A, a compound of formula (VII) is reacted sequentially with 1) (COCl)$_2$ in a non polar solvent, e.g., toluene or methylene chloride, in the presence of a tertiary amine, e.g., triethyl amine or pyridine, then 2) with 2-mercaptopyridine N-oxide sodium salt (Na-MPNO) in BrCCl$_3$ to yield the corresponding compound of formula (XVI). In step 7a the compound of formula (XVI) is reacted with liquid ammonia at about 50° C. in the presence of an ammonium salt of a weak acid, e.g., ammonium carbonate, in a pressure vessel to yield the corresponding compound of formula (IX).

Alternatively, according to another general process (B), the compounds of formula (I) wherein X is

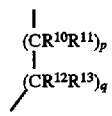

and both p and q are 1, and $R^{10}$, $R^{11}$, $R^{12}$ and $R^{13}$ are hydrogen, may be prepared by the procedure shown in Step 5 of Scheme II wherein $R^{1-6}$ are as defined for formula (I):

SCHEME II

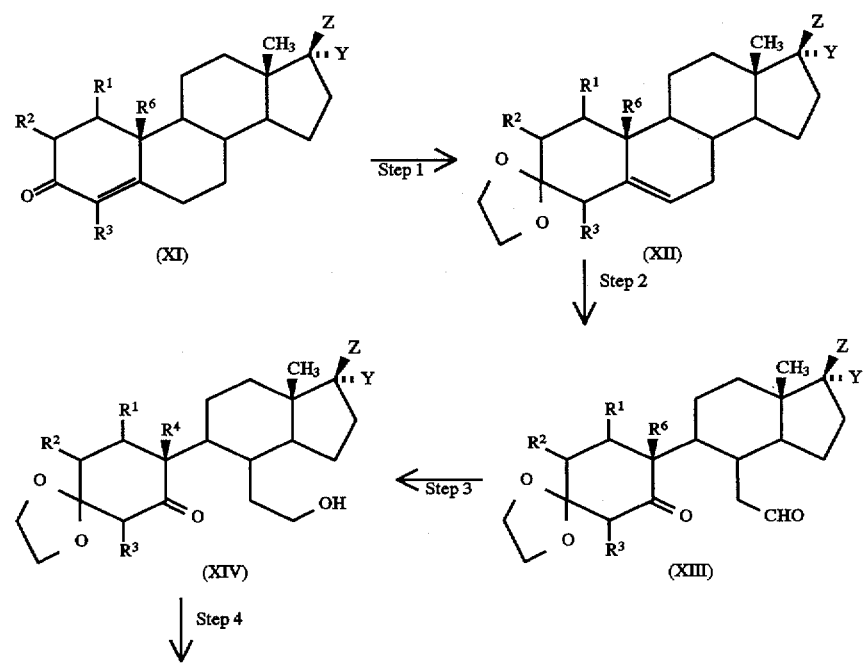

-continued
SCHEME II

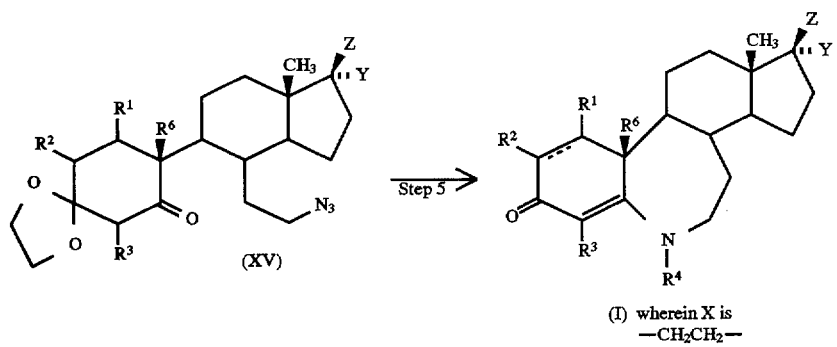

(I) wherein X is
—CH$_2$CH$_2$—

In Step 1 of Scheme II, the enone function of compound (XI) is protected as a ketal with concomitant migration of the double bond to the 5, 6 position by refluxing with ethylene glycol in the presence of an acid, such as p-toluenesulfonic acid, in a solvent such as toluene which allows azeotropic removal of water to yield the corresponding compound of formula (XIII).

In Step 2, a compound of formula (XII) is treated with ozone in methanol alone or with one or more polar, protic or aprotic solvents mixtures, e.g., methylene chloride and methanol, at a temperature substantially below 0° C., e.g., from about −50° to about −80° C., followed by treatment at about −20° C. with a reductant, such as zinc and acetic acid, then allowed to slowly warm to room temperature to yield the aldehyde of formula (XIII).

In Step 3, a compound of formula (XIII) is reduced with a selective reducing agent, such as lithium tri-t-butoxyaluminumhydride in an aprotic solvent such as THF or diethyl ether to give the corresponding alcohol of formula (XIV).

In Step 4, the alcohol functionality of a compound of formula (XIV) is converted to a leaving group, such as the corresponding methanesulfonate by treatment with methanesulfonyl chloride in an aprotic solvent such as methylene chloride in the presence of a hindered tertiary amine base such as triethylamine. Once transformed to a leaving group, the alcohol is displaced by treatment with a source of azide, such as sodium azide, in a polar, aprotic solvent, such as DMF, to give the corresponding alkyl azide of formula (XV).

In Step 5, a compound of formula (XIV) is treated with a reductant such as triphenylphosphine in THF at reflux followed by a strong protic acid such as 4M HCl to give the corresponding compound of formula (I) where X is —CH$_2$CH$_2$—.

Alternatively, according to another general process (C), a compound of formula (I) may be converted into another compound of formula (I) using conventional procedures. Thus for example, a double bond may then be inserted between the carbon in the 1 position and the carbon in the 2 position by conventional means such as dehydrogenation with 2,3-dichloro-5,6-dicyano-1,4-benzoquinone by refluxing in an aprotic solvent such as dioxane to produce a compound of formula (I) which is unsaturated in the 1,2 position. A compound of formula (I) with a double bond in the 1, 2 position may then be treated with the anion of trimethylsulfoxonium iodide, prepared by deprotonation with a base such as sodium hydride, in an aprotic, polar solvent such as DMSO to give a compound of formula (I) wherein R$^1$ and R$^2$ taken together form a cyclopropane ring.

Optionally, a compound of formula (I) wherein R$^3$ is H and R$^4$ is acyl or acyloxy, such as t-butoxycarbonyl, may be treated with bromine at 0° C. in an aprotic solvent such as methylene chloride to give the corresponding compound of formula (I) wherein R$^3$ is Br, which may then be treated with an organotin species such as phenyltrimethyltin in the presence of a palladium catalyst such as PdCl$_2$(PPh$_3$)$_2$ and lithium chloride in a polar aprotic solvent such as dimethylformamide to give the corresponding compound of formula (I) wherein R$^3$ is methyl.

Additionally, a compound of formula (I) wherein R$^4$ is acyl or acyloxy, such as t-butoxycarbonyl, may be treated with a strong hindered base such as lithium diisopropylamide at −78° C. in an aprotic solvent such as THF followed by an electrophile, such as methyl iodide to give compounds of formula (I) wherein R$^4$ is methyl or lower alkyl.

Also, a compound of formula (I) wherein R$^3$ is H may be treated with cuprous cyanide or N,N-dimethylmethyleneammonium iodide in polar, aprotic solvents such as DMF or acetonitrile to give compounds of formula (I) wherein R$^3$ is —CN and —CH$_2$N(CH$_3$)$_2$ respectively.

Additionally, a compound of formula (I) wherein R$^3$ is H may be treated with a halogenated succinimide such as N-iodosuccinimide in a solvent such as THF to give a compound of formula (I) wherein R$^3$ is I.

The compounds of formula (I) wherein R$^4$ is hydrogen may be reacted, via a nucleophilic reaction of the corresponding sodium or potassium salt, with L-lower alkyl, L-lower alkenyl, L-alkanoyl of 2 to 6 carbons, L—Alk$^1$, L-lower cycloalkyl, L-lower cycloalkyl-lower alkyl, cycloalkyl, L—(Alk$^1$)$_n$S(O)$_r$R$^7$, L—(Alk$^1$)$_n$-phthalimidyl, L—(Alk$^1$)—CO$_2$H, L—(Alk$^1$)$_n$—CO$_2$R$^7$, L—(Alk$^1$)$_n$—Ar$^1$, L—(Alk$^1$)$_n$—CONR$^8$R$^9$, L—(Alk$^1$)$_n$—NR$^8$R$^9$, L—(Alk$^1$)$_n$—OH or L—(Alk$^1$)$_n$—OR$^7$ at a temperature of about 5° to about 100° C. in a polar, aprotic solvent such as dimethylformamide, to yield the compounds of formula (I) wherein R$^4$ is other than hydrogen. The groups, R$^7$–R$^9$, Ar$^1$ and n, are as defined for formula (I) and L is a leaving group, such as defined in March, J., *Advanced Organic Chemistry*, 3d. Ed., 179, John Wiley & Sons, New York (1985) and in Hendrickson, J, et al., *Organic Chemistry*, 3d. Ed., 375–377, McGraw Hill, New York (1970), e.g., a halogen atom.

Additionally, a compound of formula (I) wherein Z is CO$_2$R$^5$, and in particular wherein R$^5$ is CH$_3$, may be treated with a strong base, such as lithium hydroxide in a solvent system such as THF or dioxane and water to give a compound of formula (I) where Z is CO$_2$H. An acid of this formula may then be treated as described in Step 1 of Scheme 1 to yield the corresponding compounds of formula (I) wherein Z is COR$^5$, CO$_2$R$^5$ or CONR$^{14}$R$^{15}$.

A particular step for the preparation of compound of formula (I) wherein Z is —$(Alk^2)_n CONR^{14}R^{15}$ involves reacting a compound of formula (I) wherein Z is $(Alk^2)_n CO_2R^5$ with an amine of formula $HNR^{14}R^{15}$, especially compounds wherein $R^{14}$ is hydrogen and $R^{15}$ is $Ar^2$ or lower cycloalkyl (optionally substituted independently with one or more $R^7$ or $Ar^2$ groups), e.g., a group of formula $Ar^{2a}$ or a cycloalkyl group substituted with a group of formula $Ar^{2a}$. Intermediates of formula $HNR^{14}R^{15}$ wherein $R^{14}$ is hydrogen and $R^{15}$ is $Ar^{2a}$ or lower cycloalkyl substituted with a group of formula $Ar^{2a}$ are novel compounds and represent a further aspect of the invention.

Optionally, a compound of formula (I) wherein Z is $CO_2R^5$, and in particular wherein $R^5$ is $CH_3$, may be reduced with a reducing agent such as diisobutyl-aluminum hydride and then reoxidized with Collins' reagent ($CRO_3$-2 pyridine) or another mild oxidant to produce a compound of formula (I) wherein Z is CHO, which may be treated with $R^5M$ (wherein M is a metal such as magnesium or lithium) and $R^5$ is $Alk^1$—H (optionally substituted independently with one or more —$CO_2H$, $CO_2R^7$, $Ar^2$ or $Ar^3$ groups), lower cycloalkyl (optionally substituted independently with one or more —$Alk^1$—H groups), adamantyl, $Ar^2$, $Ar^3$, -(lower cycloalkyl)$_n$—$Ar^2$ or —(lower cycloalkyl)$_n$—$Ar^3$ to give, after oxidation with pyridinium dichromate, a compound of formula (I) wherein Z is $COR^5$.

The above product of diisobutylaluminum hydride reduction may also be selectively oxidized at the 3-position by treatment with manganese (II) oxide to give a compound of formula (I) wherein the substitutent on C-17, that is, Z, is $CH_2$—OH, i.e., a $(Alk^2)$alkanol. This alcohol may then be converted to an amine by standard methods, e.g., conversion to a mesylate, displacement with a metal azide such as sodium azide, and reduction with hydrogen in the presence of a catalyst such as palladium on carbon. The alcohol or amine may then be reacted with acid chlorides, chloroformales, isocyanates or isothiocyanates to give compounds of formula (I) wherein Z is —$(Alk^2)$—$OCOR^5$, —$(Alk^2)$—$OCO_2R^5$, —$(Alk^2)$—$NR^5COR^5$, $(Alk^2)$—$NR^5$-$CO_2R^5$, —$(Alk^2)$—$NR^5CONR^{14}R^{15}$, —$(Alk^2)$—$NR^5CSNR^{14}R^{15}$ or —$(Alk^2)$—$OCO$—$NR^{14}R^{15}$.

Further, these compounds of formula (I), wherein Z is —CHO, may be treated with a Wittig reagent, such as $Et_2OPOCH_2COR^5$   $Et_2OPOCH_2CO_2R^5$ or $Et_2OPOCH_2CONR^{14}R^{15}$ to give a compounds of formula (I) wherein Z is —CH=CH—$COR^5$, CH=CH—$CO_2R^5$ or CH=CH—$CONR^{14}R^{15}$ respectively.

It will be appreciated by those skilled in this art that for certain cases of $R^3$ and Z some Steps in the procedures shown in Scheme I and Scheme II are incompatible with survival of the functional groups of interest. In these cases, $R^3$ or Z is either introduced subsequent to the incompatible Step or is present in a protected form. An example of the former is the case where $R^3$ is halogen, in which case the halogen is introduced by reaction of a compound of formula (I) with a halogenated succinimide, such as N-bromosuccinimide. An example of the latter is the use of an ester or ether to protect a carboxylic acid or alcohol, respectively.

Thus, according to another general pocess (D), a compound of formula (I) according to the invention, or a salt thereof may be prepared by subjecting a protected derivative of formula (I) or a salt thereof to a reaction to remove the protecting group or groups.

Thus, at an earlier stage in the preparation of a compound of formula (I) or a salt thereof it may have been necessary and/or desirable to protect one or more sensitive groups in the molecule to prevent undesirable side reactions.

The protecting groups used in the preparation of compounds of formula (I) may be used in a conventional manner. See for example Protective Groups in Organic Chemistry, Ed. J. F. W. McOmie, Plenum Press, London (1973) or Protective Groups in Organic Synthesis, Theodora Green, John Wiley and Sons, New York (1981).

Conventional amino protecting groups may include, for example, arylalkyl groups, such as benzyl, diphenylmethyl or triphenylmethyl groups; and acyl groups, such as N-benzyloxycarbonyl or t-butoxycarbonyl. Thus, compounds of formula (I) when $R^4$ represents hydrogen may be prepared by deprotection of a corresponding protected compound.

Hydroxy groups may be protected, for example, by benzyl, diphenylmethyl or triphenylmethyl groups, acyl groups, such as acetyl, silicon protecting groups, such as triisopropysilyl or t-butyldimethylsilyl groups, or as tetrahydropyran derivatives, Removal of any protecting groups present may be achieved by conventional procedures. An arylalkyl group such as benzyl, may be cleaved by hydrogenolysis in the presence of a catalyst, e.g., palladium on charcoal; an acyl group such as N-benzyloxycarbonyl may be removed by hydrolysis with, for example, hydrogen bromide in acetic acid or by reduction, for example by catalytic hydrogenation; silicon protecting groups may be removed, for example, by treatment with fluoride ion or by hydrolysis under acidic conditions; tetrahydropyran groups may be cleaved by hydrolysis under acidic conditions.

As will be appreciated, in any of the general processes (A) to (C) described above it may be desirable or even necessary to protect any sensitive groups in the molecule as just described. Thus, a reaction step involving deprotection of a protected derivative of general formula (I) or a salt thereof may be carried out subsequent to any of the above described processes (A) to (C).

Thus, according to a further aspect of the invention, the following reactions may, if necessary and/or desired be carried out in any appropriate sequence subsequent to any of the processes (A) to (C):

(i) removal of any protecting groups; and (ii) conversion of a compound of formula (I) or a salt thereof into a pharmaceutical acceptable salt or solvate thereof.

Where it is desired to isolate a compound of the invention as a salt, for example as an acid addition salt, this may be achieved by treating the free base of formula (I) with an appropriate acid, particularly with an equivalent amount, or with creatinine sulfate in a polar, protic solvent, e.g., aqueous ethanol.

As well as being employed as the last main step in the preparative sequence, the general methods indicated above for the preparation of the compounds of the invention may also be used for the introduction of the desired groups at an intermediate stage in the preparation of the required compound. It should therefore be appreciated that in such multi-stage processes, the sequence of reactions should be chosen in order that the reaction conditions do not affect groups present in the molecule which are desired in the final product.

The compound of formula (I) and the intermediate compounds, (II)–(XIV), shown in Schemes I and II may be purified by convenient methods of the art, e.g., chromatography or crystallization.

Steroid 5α-Reductases

In Vitro Assay

Enzyme activies may be determined using microsomes derived from: 1) prostate tissue from benign prostatic hyperplasia (BPH) patients; 2) recombinant baculovirus infected SF9 cells that express human type 1 5α-reductase; 3) prostate tissue from the rat; or 4) recombinant baculovirus infected SF9 cells that express human type 2 5α-reductase. Microsomes were prepared by homogenization of the tissue or cells, followed by differential centrifugation of the homogenate. Microsome extracts were incubated with varying concentrations of [1,2,6,7-3H]-testosterone, 1 mM NADPH, and varying amounts of the compounds of Formula I, i.e. a test compound, in buffer containing a NADPH regenerating system capable of maintaining NADPH concentrations for a period of time within the range 0.5–240 minutes. Corresponding incubations were carried out with no test compound as a control study. For type 1 $IC_{50}$ measurements, assay components except testosterone were preincubated for 10 minutes at pH 7.0, and following the addition of 100 nM testosterone the assays were allowed to proceed for 10–120 minutes.

For type 2 $IC_{50}$ measurements, assay components except testosterone were preincubated for 20 minutes at pH 6.0, and following the addition of 8 nM testosterone the assays were allowed to proceed for 20–40 minutes. The percentage of conversion of testosterone to DHT in the presence of test compounds compared to the corresponding conversion in the control study was estimated using high pressure liquid chromatography (HPLC) with radiochemical detection. The results of these assays appear as $IC_{50}$'s reported in Table 1.

TABLE 1

5-REDUCTASE in vitro INHIBITORY ACTIVITY

| Compound/ Example | $IC_{50}$ Human Type 1 | $IC_{50}$ Human Type 2 | $IC_{50}$ Rat Prostatic |
| --- | --- | --- | --- |
| 1 | + | +++ | ++ |
| 2 | +++ | +++ | +++ |
| 3 | ++ | ++ | +++ |
| 4 | + | +++ | + |
| 5 | + | ++ | ++ |
| 6 | + | ++ | ++ |
| 7 | + | +++ | ++ |
| 9 | ++ | +++ | +++ |
| 10 | +++ | +++ | ++ |
| 11 | ++ | +++ | +++ |
| 12 | ++ | +++ | +++ |
| 13 | ++ | +++ | +++ |
| 14 | ++ | +++ | +++ |
| 15 | + | +++ | +++ |
| 16 | ++ | +++ | +++ |
| 17 | ++ | +++ | +++ |
| 18 | ++ | +++ | +++ |
| 19 | + | ++ | ++ |
| 20 | + | ++ | ++ |
| 21 | + | ++ | + |
| 22 | ++ | +++ | +++ |
| 23 | ++ | +++ | nt |
| 24 | ++ | +++ | +++ |
| 25 | ++ | +++ | +++ |
| 26 | ++ | +++ | nt |
| 27 | +++ | +++ | ++ |
| 28 | ++ | ++ | +++ |
| 29 | + | ++ | ++ |
| 30 | ++ | +++ | + |
| 31 | ++ | +++ | +++ |
| 32 | ++ | +++ | +++ |
| 33 | + | ++ | ++ |
| 34 | ++ | +++ | +++ |
| 35 | + | +++ | +++ |

TABLE 1-continued

5-REDUCTASE in vitro INHIBITORY ACTIVITY

| Compound/ Example | $IC_{50}$ Human Type 1 | $IC_{50}$ Human Type 2 | $IC_{50}$ Rat Prostatic |
| --- | --- | --- | --- |
| 36 | + | +++ | +++ |
| 37 | ++ | +++ | nt |
| 38 | ++ | +++ | + |
| 39 | ++ | +++ | ++ |
| 40 | ++ | +++ | ++ |
| 41 | ++ | +++ | + |
| 42 | ++ | +++ | +++ |
| 43 | +++ | +++ | + |
| 44 | ++ | +++ | + |
| 45 | + | +++ | ++ |
| 46 | ++ | +++ | +++ |
| 47 | ++ | +++ | +++ |
| 48 | +++ | +++ | ++ |
| 49 | +++ | +++ | +++ |
| 50 | +++ | +++ | ++ |
| 51 | + | ++ | + |
| 52 | ++ | +++ | ++ |
| 53 | ++ | +++ | +++ |
| 54 | ++ | +++ | nt |
| 55 | ++ | +++ | nt |
| 56 | ++ | +++ | nt |
| 57 | ++ | ++ | nt |
| 58 | ++ | +++ | nt |
| 59 | + | ++ | nt |
| 60 | + | ++ | nt |
| 61 | ++ | +++ | nt |
| 62 | + | +++ | nt |
| 63 | + | +++ | nt |
| 64 | +++ | +++ | nt |
| 65 | ++ | +++ | nt |
| 66 | + | +++ | nt |
| 67 | + | +++ | nt |
| 68 | ++ | +++ | nt |
| 69 | ++ | +++ | nt |
| 70 | ++ | +++ | nt |
| 71 | ++ | +++ | nt |
| 72 | ++ | +++ | nt |
| 73 | +++ | +++ | nt |
| 74 | +++ | +++ | nt |
| 75 | +++ | +++ | nt |
| 76 | ++ | +++ | nt |
| 77 | +++ | +++ | nt |
| 78 | ++ | +++ | nt |
| 79 | ++ | +++ | nt |
| 80 | ++ | +++ | nt |
| 81 | ++ | +++ | nt |
| 82 | +++ | +++ | nt |
| 83 | ++ | +++ | nt |
| 84 | ++ | +++ | nt |
| 85 | +++ | +++ | nt |
| 86 | +++ | +++ | nt |
| 87 | +++ | +++ | nt |
| 88 | +++ | +++ | nt |
| 89 | ++ | +++ | nt |
| 90 | +++ | +++ | nt |
| 91 | ++ | +++ | ++ |
| 92 | ++ | +++ | nt |
| 93 | ++ | +++ | + |
| 94 | ++ | +++ | nt |
| 95 | + | ++ | nt |
| 96 | ++ | +++ | nt |
| 97 | + | ++ | nt |
| 98 | +++ | +++ | nt |
| 99 | +++ | +++ | nt |
| 100 | +++ | +++ | nt |
| 101 | +++ | +++ | nt |
| 102 | +++ | +++ | nt |
| 103 | ++ | +++ | nt |
| 104 | ++ | +++ | nt |
| 105 | +++ | +++ | nt |
| 106 | +++ | +++ | nt |
| 107 | + | +++ | nt |
| 108 | ++ | +++ | nt |
| 109 | +++ | +++ | nt |

TABLE 1-continued

5-REDUCTASE in vitro INHIBITORY ACTIVITY

| Compound/ Example | IC$_{50}$ Human Type 1 | IC$_{50}$ Human Type 2 | IC$_{50}$ Rat Prostatic |
|---|---|---|---|
| 110 | ++ | +++ | nt |
| 111 | +++ | +++ | nt |
| 112 | ++ | +++ | nt |
| 113 | ++ | +++ | nt |
| 114 | ++ | +++ | nt |
| 115 | +++ | +++ | nt |
| 116 | +++ | +++ | nt |
| 117 | +++ | +++ | nt |
| 118 | +++ | +++ | nt |
| 119 | ++ | +++ | nt |
| 120 | +++ | +++ | nt |
| 121 | +++ | +++ | nt |
| 122 | +++ | +++ | nt |
| 123 | ++ | +++ | nt |
| 124 | ++ | +++ | nt |
| 125 | +++ | +++ | nt |
| 126 | +++ | +++ | nt |
| 127 | +++ | +++ | nt |
| 128 | +++ | +++ | nt |
| 129 | ++ | +++ | nt |
| 130 | +++ | +++ | nt |
| 131 | +++ | +++ | nt |
| 132 | ++ | +++ | nt |
| 133 | + | +++ | nt |
| 134 | ++ | +++ | nt |
| 135 | + | +++ | nt |
| 136 | +++ | +++ | nt |
| 137 | + | +++ | nt |
| 138 | ++ | +++ | nt |
| 139 | +++ | +++ | nt |
| 140 | +++ | +++ | nt |
| 141 | + | +++ | nt |
| 142 | + | +++ | nt |
| 143 | +++ | +++ | nt |
| 144 | +++ | +++ | nt |
| 145 | +++ | +++ | nt |
| 146 | +++ | +++ | nt |
| 147 | +++ | +++ | nt |
| 148 | nt | nt | nt |

+++ = <10 nM
++ = 10–100 nM
+ = >100 nM
nt = not tested

In Vivo Evaluation of Steroid 5α-Reductase Inhibitor

The in vivo activity of steroid 5α-reductase inhibitors may be determined in both acute and chronic rat models. The acute model utilizes castrated male rats that receive testosterone (1 mg) subcutaneously and test compound (10 mg/kg) p.o., at 0.5 hr. and 4.5 hr. prior to sacrifice, respectively. Levels of DHT in the serum and prostate indicate the ability of the test compound to inhibit steroid 5α-reductase in an acute rat model. Known steroid 5α-reductase inhibitors were tested in parallel to ensure consistency of the assay method.

The chronic model also utilizes castrated male rats that are dosed daily with testosterone (20 μg/rat) subcutaneously and with test compound (0.01–10 mg/kg) p.o. for 7 days. The animals are then sacrificed and their prostates weighed. Reduction in the size of testosterone-stimulated prostate weight demonstrated activity of the test compound. Known steroid 5α-reductase inhibitors were tested in parallel to ensure consistency of the assay method.

Utility

The steroid 5α-reductase inhibitors of the present invention are useful in the treatment of androgen responsive diseases, e.g., benign and malignant diseases of the prostate, especially benign prostatic hyperplasia. For correlation of in vitro, rat in vivo and human clinical data relating to an inhibitor of 5α-reductase, see Stoner, *J. Steroid Biochem. Molec. Biol.*, 37, 375 (1990); Brooks, et al., *Steroids*, 47, 1 (1986) and Rasmusson, *J. Med. Chem.*, 29, 2298 (1986)). They are also useful in the treatment of prostatitis, prostate cancer, androgen mediated diseases of the skin, such as acne, hirsutism and male pattern baldness. Other hormone related diseases, e.g., polycystic ovary disease, would be expected to respond to treatment with these inhibitors.

The amount of compound of formula (I) required to be effective as an 5α-reductase inhibitor will, of course, vary with the individual mammal being treated and is ultimately at the discretion of the medical or veterinary practitioner. The factors to be considered include the condition being treated, the route of administration, the nature of the formulation, the mammal's body weight, surface area, age and general condition, and the particular compound to be administered. However, a suitable effective 5α-reductase inhibitory dose is in the range of about 0.01 to about 5 mg/kg body weight per day, preferably in the range of about 0.05 to about 2 mg/kg per day.

The total daily dose may be given as a single dose, multiple doses, e.g., two to six times per day, or by intravenous infusion for a selected duration. Dosages above or below the range cited above are within the scope of the present invention and may be administered to the individual patient if desired and necessary. For example, for a 75 kg mammal, a dose range would be about 5 to about 150 mg per day, and a typical dose would be about 20 mg per day. If discrete multiple doses are indicated, treatment might typically be 5 mg of a compound of formula (I) given 4 times per day.

The compounds of formula (I) may also be administered in a topical formulation, e.g., ointment, cream, gel, or lotion, in cases of dermatological disorders such as acne vulgaris. An effective topical formulation contains from about 0.25% to about 10% by weight, of a compound of formula (I) which is applied at the rate of about 0.1 g to about 1.0 g per square centimeter of infected skin area. Typically a dose is about 1 gram of a 1% ointment, cream, gel, or lotion of a compound of formula (I) gently rubbed onto the square centimeter of skin in need of treatment.

Formulations

Formulations of the present invention for medical use comprise an active compound, i.e., a compound of formula (I), together with an acceptable carrier thereof and optionally other therapeutically active ingredients. The carrier must be pharmaceutically acceptable in the sense of being compatible with the other ingredients of the formulation and not deleterious to the recipient thereof.

The present invention, therefore, further provides a pharmaceutical formulation comprising a compound of formula (I) together with a pharmaceutically acceptable carrier thereof.

The formulations include those suitable for oral, rectal, topical or parenteral (including subcutaneous, intramuscular and intravenous) administration. Preferred are those suitable for oral or parenteral administration.

The formulations may conveniently be presented in unit dosage form and may be prepared by any of the methods well known in the art of pharmacy. All methods include the step of bringing the active compound into association with a carrier which constitutes one or more accessory ingredients. In general, the formulations are prepared by uniformly and intimately bringing the active compound into association with a liquid carrier or a finely divided solid carrier and then, if necessary, shaping the product into desired unit dosage form.

Formulations of the present invention suitable for oral administration may be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, an emulsion or a draught.

A tablet may be made by compression or molding, optionally with one or more accessory ingredients. Compressed tablets may be prepared by compressing in a suitable machine the active compound in a free-flowing form, e.g., a powder or granules, optionally mixed with accessory ingredients, e.g., binders, lubricants, inert diluents, surface active or dispersing agents. Molded tablets may be made by molding in a suitable machine, a mixture of the powdered active compound with any suitable carrier.

A syrup or suspension may be made by adding the active compound to a concentrated, aqueous solution of a sugar, e.g., sucrose, to which may also be added any accessory ingredients. Such accessory ingredient(s) may include flavoring, an agent to retard crystallization of the sugar or an agent to increase the solubility of any other ingredient, e.g., as a polyhydric alcohol, for example, glycerol or sorbitol.

Formulations for rectal administration may be presented as a suppository with a conventional carrier, e.g., cocoa butter or Witepsol S55 (trademark of Dynamite Nobel Chemical, Germany), for a suppository base.

Formulations suitable for parenteral administration conveniently comprise a sterile aqueous preparation of the active compound which is preferably isotonic with the blood of the recipient. Such formulations suitably comprise a solution or suspension of a pharmaceutically and pharmacologically acceptable acid addition salt of a compound of the formula (I) that is isotonic with the blood of the recipient.

Thus, such formulations may conveniently contain distilled water, 5% dextrose in distilled water or saline and a pharmaceutically and pharmacologically acceptable acid addition salt of a compound of the formula (I) that has an appropriate solubility in these solvents, for example the hydrochloride, isothionate and methanesulfonate salts, preferably the latter. Useful formulations also comprise concentrated solutions or solids containing the compound of formula (I) which upon dilution with an appropriate solvent give a solution suitable for parental administration above.

Topical formulations include ointments, creams, gels and lotions which may be prepared by conventional methods known in the art of pharmacy. In addition to the ointment, cream, gel, or lotion base and the active ingredient, such topical formulation my also contain preservatives, pedumes, and additional active pharmaceutical agents.

In addition to the aforementioned ingredients, the formulations of this invention may further include one or more optional accessory ingredient(s) utilized in the art of pharmaceutical formulations, e.g., diluents, buffers, flavoring agents, binders, sudace active agents, thickeners, lubricants, suspending agents, preservatives (including antioxidants) and the like.

EXAMPLES

The following examples illustrate aspects of this invention but should not be construed as limitations. The symbols and conventions used in these examples are consistent with those used in the contemporary chemical literature, for example, the Journal of the American Chemical Society.

Example 1

17β-N-9-Flourenyl-carbamoyl-6-azaandrost-4-en-3-one (Compound 1)

A. 3β-Triisopropylsilyloxyetienic acid methyl ester

A suspension of 3β-hydroxyetienic acid methyl ester (*J. Med. Chem.* 27, 1690) (516 g, 1.55 mol) in DMF (800 mL) is heated to 55° C., imidazole (264 g, 3.88 mol) added with vigorous mechanical stirring, followed by dropwise addition of triisopropylsilylchloride (360 g, 1.87 mol). The reaction becomes homogeneous after about half of the triisopropylsilylchloride is added and the reaction temperature increases to ca. 70° C. The reaction is complete by TLC (35% ethyl acetate/hexanes) after 1.5 hrs and a thick slurry forms. The reaction is cooled to 0° C., 1 L of ice water added with stirring, the solid collected by filtration and washed with water (500 mL) and methanol (500 mL). The resulting tan solid is suspended in methanol (1 L) and allowed to stir overnight to give, on filtration, 3β-triisopropylsilyloxyetienic acid methyl ester as a tan solid of sufficient purity to carry on to the following steps; yield: 667 g (88%); m.p. 116°–118° C. Recrystallization from hexane gives an analytical sample as a white crystalline solid: m.p. 124°–125° C. Anal. Calcd. for $C_{30}H_{52}O_3Si$; C, 73.71; H, 10.72. Found: C, 73.79; H, 10.74.

B. A solution of 3β-triisopropylsilyloxyetienic acid methyl ester (166 g, 0.34 mol), from part A, in methylene chloride (2 L) and methanol (800 mL) is cooled to −78° C. and treated with ozone until a blue color persists. At this stage, the peroxy compound of formula (V) may be isolated and recrystallized from hexanes to give an analytical sample; m.p. 119°–121° C. Anal. Calcd. for $C_{31}H_{56}O_7Si$; C, 65.45; H, 9.92. Found: C, 65.37; H, 9.86. However, more conveniently, the reaction is allowed to warm to −50° C. under a stream of nitrogen, zinc dust added (89 g, 1.36 mol), followed by glacial acetic acid (150 mL). The reaction is then allowed to warm to room temperature with stirring, filtered to remove zinc, the solution washed with water, saturated aqueous NaCl, saturated aqueous bicarbonate, dried over $MgSO_4$ and concentrated by rotary evaporation to give crude keto-aldehyde of formula (VI) as a white foam; yield: 176 g (99%).

C. The compound prepared in part B above (176 g, 0.34 mol) is dissolved in acetone, cooled to 0° C. and treated with Jones reagent (1.05 eq.) by dropwise addition over 15 min. After 10 min isopropanoi is added, the reaction is allowed to stir for 10 min, is filtered, concentrated, dissolved in ethyl acetate (400 mL), washed with saturated NaCl, dried ($MgSO_4$) and concentrated to a green oil. The oil is dissolved in methylene chloride (150 mL), silica gel added (50 g), the mixture filtered through silica gel (200 g) and eluted with hexane/methylene chloride/ethyl acetate/methanol (8:8:4:1) to give on concentration the corresponding keto-acid of formula (VII) as an off-white solid; yield: 163 g (89%). Recrystallization from ethyl acetate/hexanes gives a white crystalline solid; m.p. 143°–145° C. Anal. Calcd. for $C30H_{52}O_6Si$; C, 67.12; H, 9.76. Found: C, 67.21; H, 9.80.

D. 17β-Carbomethoxy-3β-triisopropylsilyloxy-6-azaandrost-5-ene

A portion of the keto-acid of formula (VII) prepared above (110 g, 0.205 mol) is dissolved in methylene chloride (120 mL) and pyridine (44.7 mL) and is added dropwise to a solution of oxalyl chloride (48.3 mL, 0.553 mol) in methylene chloride (770 mL) at 0° C. After stirring 30 min, the reaction is poured into a mixture of saturated aqueous NaCl and ice (700 mL), the layers separated, the methylene chloride is washed with ice-cold 0.5M HCl (2×800 mL), ice-cold saturated $NaHCO_3$ (3×700 mL), dried ($Na_2SO_4$) and concentrated to give the acid chloride as a white foam; yield: 110 g (96%). This material is then dissolved in acetone (1 L) and pentane (55 mL), cooled to 0° C., and treated with an aqueous solution of sodium azide (53 g, 0.82 mol, 164 mL). After 30 min the reaction is poured into a mixture of saturated NaCl (300 mL), saturated $NaHCO_3$ (300 mL) and ice (300 mL). Toluene is added (1 L), the layers separated, toluene layer washed with ice-cold saturated $NaHCO_3$ (3×400 mL), dried ($Na_2SO_4$), filtered and heated to 110° C. to distill down to one-half the original volume. The solution is cooled to 38° C. and treated with silica gel (212 g). The reaction is allowed to stir overnight, the silica removed by filtration and washed with 4:1 ethyl acetate/methanol (770 mL) to give 17β-carbomethoxy-3β-triisopropylsilyloxy-6-azaandrost-5-ene (a compound of formula ((IX)) as a white foam; yield: 106 g (94%). Flash chromatography on silica gel (30% ethyl acetate/hexanes) gives an analytical sample as a white foam. Anal. Calcd. for $C_{29}H_{51}NO_3Si$; C, 71.11; H, 10.49; N, 2.86. Found: C, 71.04; H, 10.51; N, 2.80.

E. 17β-Carbomethoxy-6-t-butoxycarbonyl-6-azaandrost-4-en-3-one

A portion of the crude product from above, 17β-carbomethoxy-3β-triisopropylsilyloxy-6-azaandrost-5-ene (66 g, 0.135 mol) is dissolved in pyridine (500 mL), treated with di-t-butyldicarbonate (150 g, 0.69 mol) and allowed to stir overnight. The pyridine is removed by rotary evaporation and tetrabutylammonium fluoride (500 mL, 1M, 0.5 mol) in tetrahydrofuran (THF) added carefully and the reaction heated to reflux for 5 min. The THF is removed by rotary evaporation, the residue dissolved in ethyl acetate (500 mL), washed cautiously with water, saturated aqueous NaCl, dried with $MgSO_4$ and concentrated. This material is dissolved in DMF (500 mL), is treated with pyridinium dichromate (153 g, 0.41 mol) and allowed to stir overnight. The reaction is poured into water (700 mL) and extracted with ethyl acetate (2×500 mL). The combined extracts are washed with water, 5% aqueous $CuSO_4$, saturated aqueous NaCl, dried over $MgSO_4$, concentrated and flash chromatographed (0–60%, diethyl ether/hexanes) to give 17β-carbomethoxy-6-t-butoxycarbonyl-6-azaandrost-4-en-3-one as an off-white foam; yield: 37.5 g (64%); FAB mass spec. $MH^+432$.

F. 17β-Carboxy-6-t-butoxycarbonyl-6-azaandrost-4-en-3-one

A solution of 17β-carbomethoxy-6-t-butoxycarbonyl-6-azaandrost-4-en-3-one (15.4 g, 36 mmol), from part E, in dioxane (150 mL) and water (100 mL) is treated with $LiOH.H_2O$ (3.31 g, 79 mmol) and stirred overnight in a water bath. The reaction is poured into saturated aqueous $NaHSO_4$ (150 mL), extracted with methylene chloride (3×100 mL), extracts washed with saturated aqueous NaCl, dried over $MgSO_4$ and concentrated to a volume of 100 mL. At this point crystals begin to form and 2:1 hexanes/ethyl acetate (50 mL) is added, the mixture triturated, cooled to room temperature and 17β-carboxy-6-t-butoxycarbonyl-6-azaandrost-4-en-3-one collected as a fluffy white powder; yield: 9.44 g (63%); m.p. 215°–216° C. Anal. Calcd. for $C_{24}H_{35}NO_5.¼H_2O$; C, 68.30; H, 8.48; N, 3.32. Found: C, 68.45; H, 8.41; N, 3.28.

The mother liquor is diluted with methylene chloride (100 mL), filtered through silica gel, silica washed with 1:1 diethyl ether/hexanes and the eluant concentrated to give recovered 17β-carbomethoxy-6-t-butoxycarbonyl-6-azaandrost-4-en-3-one; yield: 2.63 g (17%). The silica pad is then washed with 1:9 methanol/methylene chloride (250 mL), the eluant concentrated, the resulting solid triturated with 2:1 hexanes/ethyl acetate (50 mL), cooled to 0° C. and 17β-carboxy-6-t-butoxycarbonyl-6-azaandrost-4-en-3-one collected as a white powder; yield: 2.25 g (15%). The combined yield based on recovered starting material is 94%.

G. 17β-N-9-Fluorenyl-carbamoyl-6-azaandrost-4-en-3-one

A sample of 17β-carboxy-6-t-butoxycarbonyl-6-azaandrost-4-en-3-one (502 mg, 1.20 mmol), from part F, is suspended in toluene (15 mL), treated with pyridine (0.15 mL, 1.5 eq.), cooled to 0° C. and thionyl chloride added (0.13 mL, 1.5 eq.). After 1 hr at 0° C. the reaction is concentrated to a yellow solid, this crude acid chloride is dissolved in methylene chloride (15 mL) and added to a biphasic mixture of methylene chloride (5 mL) and saturated aqueous $NaHCO_3$ (5 mL) which contains 9-fluorenyl amine hydrochloride (2.5 eq.). After stirring 45 min, ethyl acetate (50 mL) is added, the layers separated, the ethyl acetate layer washed with saturated aqueous $NaHSO_4$, saturated aqueous NaCl, dried over $MgSO_4$, concentrated and chromatographed on silica gel (35–50% ethyl acetate/hexanes) to give 17β-N-9-fluorenyl-carbamoyl-6-t-butoxycarbonyl-6-azaandrost-4-en-3-one as a yellow oil; yield: 558 mg (80%). This material is dissolved in methylene chloride (15 mL) and treated with trifluoroacetic acid (2 mL at room temperature. After 3 hrs the reaction is concentrated, methylene chloride (50 mL) and saturated aqueous bicarbonate (50 mL) added, the layers separated, methylene chloride washed with saturated aqueous NaCl, dried over $MgSO_4$, concentrated and crystallized from acetonitrile to give 17β-N-9-fluorenyl-carbamoyl-6-azaandrost-4-en-3-one as a white crystalline solid; yield: 325 mg (56%); m. p. 227°–230° C. Anal. Calcd. for $C_{32}H_{36}N_2O_2.½H_2O$; C, 78.49; H, 7.62; N, 5.72. Found: C, 78.25; H, 7.67; N, 5.65.

Example 2

17β-(1-Oxo-2-cyclohexylethyl)-6-azaandrost-4-en-3-one (Compound 2)

A solution of 17β-carboxy-6-t-butoxycarbonyl-6-azaandrost-4-en-3-one (260 mg, 0.62 mmol), example 1, part F, is dissolved in toluene (10 mL) and treated with pyridine (3 eq) and catalytic dimethylformamide, cooled to 0° C., and thionyl chloride added (80 mL, 1.10 mmol). The reaction is then allowed to warm to room temperature and stir for 1 hr. The solids are then removed by filtration, the solution concentrated, the resulting crude acrid chloride dissolved in THF (6 mL), CuI added (120 mg, 0.62 mmol), cooled to −78° C. and treated with methylenecyclohexylmagnesium bromide (2.0M in diethyl ether, 0.5 mL, 1 mmol). The reaction is allowed to warm to room temperature, stir for 30 min, is quenched with saturated $NaHSO_4$, extracted with ethyl acetate (2×25 mL), dried over $MgSO_4$, concentrated and chromatographed on silica gel (25% ethyl acetate/hexane) to give 17β-(1-oxo-2-(cyclohexylethyl))-6-t-butoxycarbonyl-6-azaan-drost-4-en-3-one; yield: 302 mg (98%). This material may be deprotected as described in example 1, part G above to give, on crystallization from ether, 17β-(1-oxo-2-(cyclohexylethyl)-6-azaandrost-4-en-3-one; yield: 121 mg (50%); m.p. 214°–216° C. Anal. Calcd. for $C_{26}H_{39}NO_2.½H_2O$; C, 76.80; H, 9.92; N, 3.44. Found: C, 76.61; H, 9.89; N, 3.49.

Example 3

17β-Hydroxymethyl-(trimethylacetate)-6-azaandrost-4-en-3-one (Compound 3)

A. 17β-Hydroxymethyl-3β-hydroxy-6-t-butoxycarbonyl-6-azaandrost-4-ene

A solution of 17β-carbomethoxy-6-t-butoxycarbonyl-6-azaandrost-4-en-3-one (2.30 g, 5.33 mmol), example 1, part E, in methylene chloride (70 mL) at −78° C. is treated with diisobutylaluminum hydride (1.5M in toluene, 15 mL, 22.5 mmol). After 20 minutes the reaction is quenched with methanol (4 mL), methylene chloride added (150 mL), washed with 2N NaOH and water, dried over MgSO$_4$ and concentrated to give crude 17hydroxymethyl-3-hydroxy-6-t-butoxycarbonyl-6-azaandrost-4-ene of sufficient purity to carry on to the following steps; yield: 2.16 g (99%).

B. 17β-Hydroxymethyl-6-t-butoxycarbonyl-6-azaandrost-4-en-3-one

A solution of 17β-Hydroxymethyl-3b-hydroxy-6-t-butoxycarbonyl-6-azaandrost-4-ene (prepared as described in Example 5 above), in chloroform (250 mL) is treated with activated manganese(IV) oxide. After stirring 3.5 h, the manganese salts are removed by filtration through Celite. The solution is concentrated and chromatographed on silica gel (50% ethyl acetate/hexanes) to give 17β-hydroxymethyl-6-t-butoxycarbonyl-6-azaandrost-4-en-3-one of sufficient purity to carry on to subsequent steps; yield 9.75 g (98%).

C. 17β-Hydroxymethyl-(trimethylacetate)-6-azaandrost-4-en-3-one

A solution of 17β-hydroxymethyl-6-t-butoxycarbonyl-6-azaandrost-4-en-3-one (1.28 g, 3.17 mmol) in dichloromethane (32 mL) is cooled to 0° C. and treated with triethylamine (0.67 mL, 4.8 mmol), 4-dimethylaminopyridine (58.4 mg, 0.48 mmol), and trimethylacetyl chloride (0.6 mL, 4.8 mmol). After stirring 1 h at 0° C. and 3 h at room temperature, the reaction is diluted with dichloromethane, washed with saturated aqueous NaHSO$_4$, saturated aqueous NaHCO$_3$, and saturated aqueous NaCl, dried over MgSO$_4$, filtered, concentrated, and chromatographed on silica gel (25% ethyl acetate/hexanes) to give the crude ester. This material is treated with trifluoroacetic acid as described in Example 4 above to give, after recrystallization from dichloromethane/acetonitrile, 17β-Hydroxymethyl-(trimethylacetate)-6-azaandrost-4-en-3-one as a white powder; yield: 843 mg (69%); m.p. 239°–241° C. Anal. Calcd. for $C_{24}H_{37}NO_3$: C, 74.38; H, 9.62; N, 3.61. Found: C, 74.17; H, 9.64; N, 3.58.

Example 4–86

Following the general procedure of example 1, part G, wherein the hydrochloride salt of the amine is reacted with the acid chloride in the presence of sodium bicarbonate or by reaction with the free base or metal salt of the amine, for preparation of amides as the Z substituent in compounds of formula (I); the general procedure of example 2 for preparation of ketones as the Z substituent in compounds of formula (I); and the general procedure of example 3 for preparation of compounds where Z=CH$_2$OCOR$^5$ and Z=CH$_2$OCO$_2$R$^5$ in compounds of formula (I) the following compounds were prepared:

Example 4

17β-N-5-Indanylcarbamoyl-6-azaandrost-4-en-3-one (Compound 4)

Melting Point: >270° C. Anal. Calcd. for $C_{28}H_{36}N_2O_2 \cdot \frac{3}{4}H_2O$; C, 75.39; H, 8.47; N, 6.30. Found: C, 75.29; H, 8.42; N, 6.20.

Example 5

17β-N-Phenyl-(4-morpholino)-carbamoyl-6-azaandrost-4-en-3-one (Compound 5)

Melting Point: >250° C. Anal. Calcd. for $C_{29}H_{39}N_3O_3 \cdot \frac{1}{4}H_2O$; C, 72.24; H, 8.26; N, 8.72. Found: C, 72.26; H, 8.26; N, 8.73.

Example 6

17β-N-4-Benzodioxan-carbamoyl-6-azaandrost-4-en-3-one (Compound 6)

Melting Point: >260° C. Anal. Calcd. for $C_{27}H_{34}N_2O_4$; C, 71.97; H, 7.61; N, 6.22. Found: C, 71.70; H, 7.68; N, 6.18.

Example 7

17β-N-3,4-Methylenedioxy)phenyl-carbamoyl-6-azaandrost-4-en-3-one (Compound 7)

Melting Point: >264° C. Anal. Calcd. for $C_{26}H_{32}N_2O_4 \cdot H_2O$; C, 68.70; H, 7.54; N, 6.16. Found: C, 68.78; H, 7.60; N, 5.96.

Example 8

17β-N-2-(3-Indolyl)ethyl-carbamoyl-6-azaandrost-4-en-3-one (Compound 8)

Melting Point: 196°–202° C. Anal. Calcd. for $C_{29}H_{37}N_3O_2 \cdot \frac{1}{2}H_2O$; C, 74.33; H, 8.17; N, 8.97. Found: C, 74.31; H, 8.15; N, 8.87.

Example 9

17β-N-(2-Trifluoromethyl)phenyl-carbamoyl-6-azaandrost-4-en-3-one (Compound 9)

Melting Point: 249°–253° C. Anal. Calcd. for $C_{26}H_{31}N_2O_2F_3 \cdot \frac{1}{3}H_2O$; C, 66.93; H, 6.84; N, 6.00. Found: C, 67.02; H, 7.00; N, 5.71.

Example 10

17β-N-(2,5-Di-t-butyl)phenyl-carbamoyl-6-azaandrost-4-en-3-one (Compound 10)

Melting Point: 178°–186° C. Anal. Calcd. for $C_{33}H_{48}N_2O_2 \cdot \frac{1}{4}H_2O$; C, 77.83; H, 9.60; N, 5.50. Found: C, 77.72; H, 9.61; N, 5.49.

Example 11

17β-N-(4-Chlorophenyl)(phenyl)methyl-carbamoyl-6-azaandrost-4-en-3-one (Compound 11)

Melting Point: 245°–250° C. (decomp.). Anal. Calcd. for $C_{32}H_{37}N_2O_2Cl \cdot \frac{3}{8}H_2O$; C,73.37; H,7.26;N, 5.35;Cl,6.78. Found: C,73.24; H,7.23; N,5.38Cl,6.76.

Example 12

17β-N-(4-Methyl)phenethyl-carbamoyl-6-azaandrost-4-en-3-one (Compound 12)

Melting Point: 244°–246° C. Anal. Calcd. for $C_{28}H_{38}N_2O_2 \cdot \frac{1}{4}H_2O$; C, 76.59; H, 8.84; N, 6.38. Found: C, 76.97; H, 8.93; N, 6.40.

Example 13

7.6β-N-(α-Methyl)phenethyl-carbamoyl-6-azaandrost-4-en-3-one (Compound 13)

Melting Point: 188°–189° C. Anal. Calcd. for $C_{28}H_{38}N_2O_2 \cdot \frac{1}{4}H_2O$; C, 76.59; H, 8.84; N, 6.38. Found: C, 76.32; H, 9.00; N, 6.29.

Example 14

17β-N-(2,6-Di-i-propyl)phenyl-carbamoyl-6-azaandrost-4-en-3-one (Compound 14)

Example 15

17β-N-1-Fluorenyl-carbamoyl-6-azaandrost-4-en-3-one (Compound 15)

Melting Point: 215°–230° C. (decomp.). Anal. Calcd. for $C_{32}H_{36}N_2O_2 \cdot ¾H_2O$; C, 77.78; H, 7.65; N, 5.67. Found: C, 77.91; H, 7.56; N, 5.76.

Example 16

17β-N-(3,3-Diphenyl)propyl-carbamoyl-6-azaandrost-4-en-3-one (Compound 16)

Melting Point: 136°–141° C. Anal. Calcd. for $C_{34}H_{42}N_2O_2 \cdot ½H_2O$; C, 78.57; H, 8.34; N, 5.39. Found: C, 78.86; H, 8.29; N, 5.40.

Example 17

17β-N-(α-Phenyl)phenethyl-carbamoyl-6-azaandrost-4-en-3-one (Compound 17)

Melting Point: >250° C. Anal. Calcd. for $C_{33}H_{40}N_2O_2$; C, 79.80; H, 8.12; N, 5.64. Found: C, 79.74; H, 8.11; N, 5.60.

Example 18

17β-N-(4-Fluorophenyl)(2-thiophene)methyl-carbamoyl-6-azaandrost-4-en-3-one (Compound 18)

Melting Point: 172°–180° C. Anal. Calcd. for $C_{30}H_{35}N_2O_2S \cdot ⅜H_2O$; C,70.16; H,7.02;N,5.46; S,6.25. Found: C,70.18; H,6.99;N,5.50;S,6.24.

Example 19

17β-N-(2-Furanyl)methyl-carbamoyl-6-azaandrost-4-en-3-one (Compound 19)

Melting Point: 156°–158° C. Anal. Calcd. for $C_{24}H_{32}N_2O_3 \cdot 1¼H_2O$; C, 68.79; H, 8.30; N, 6.68. Found: C, 68.59; H, 8.18; N, 6.59.

Example 20

17β-N-2-(2-Pyridyl)ethyl-carbamoyl-6-azaandrost-4-en-3-one (Compound 20)

Melting Point: 132°–135° C. Anal. Calcd. for $C_{26}H_{35}N_3O_2 \cdot H_2O$; C, 71.04; H, 8.48; N, 9.55. Found: C, 70.99; H, 8.46; N, 9.12.

Example 21

17β-N-(1,1-Dimethyl)-2-hydroxyethyl-carbamoyl-6-azaandrost-4-en-3-one (Compound 21)

Melting Point: 170° C. (decomp.). FAB mass spec. for $C_{23}H_{36}N_2O_3$; 388.54 Found: 389 MH$^+$

Example 22

17β-N-(2,2-Diphenyl)ethyl-carbamoyl-6-azaandrost-4-en-3-one (Compound 22)

Melting Point: >250° C. FAB mass spec. for $C_{33}H_{40}N_2O_2$; 496.7 Found: 497 MH$^+$

Example 23

17β-N-2-(Phenylthio)ethyl-carbamoyl-6-azaandrost-4-en-3-one (Compound 23)

Melting Point: 130°–131° C. Anal. Calcd. for $C_{27}H_{36}N_2O_2S \cdot H_2O$; C, 68.90; H, 8.13; N, 5.95. Found: C, 68.59; H, 7.76; N, 5.94.

Melting Point: 198°–200° C. Anal. Calcd. for $C_{31}H_{44}N_2O_2 \cdot ½H_2O$; C, 76.66; H, 9.33; N, 5.76. Found: C, 76.77; H, 9.09; N, 5.77.

Example 24

17β-N-Bis-(4-fluorophenyl)methyl-carbamoyl-6-azaandrost-4-en-3-one (Compound 24)

Melting Point: 178°–184° C. Anal. Calcd. for $C_{32}H_{36}N_2O_2F_2 \cdot ¼H_2O$; C, 73.47; H, 7.03; N, 5.36. Found: C, 73.55; H, 7.04; N, 5.33.

Example 25

17β-N-(2,2-Diphenyl)-hydrazidyl-6-azaandrost-4-en-3-one (Compound 25)

Melting Point: 194°–196° C. Anal. Calcd. for $C_{31}H_{37}N_3O_2 \cdot ½H_2O$; C,75.55; H,7.78; N,8.53. Found: C, 75.44; H, 7.82; N, 8.50.

Example 26

17β-(1-Oxo-1-(2,4-difluorophenyl)methyl)-6-azaandrost-4-en-3-one (Compound 26)

Melting Point: 238° C. (decomp.). Anal. Calcd. for $C_{25}H_{29}NO_2F_2 \cdot ¼H_2O$; C,71.83; H7.11; N,3.35. Found: C, 72.07; H, 6.97; N, 3.64.

Example 27

17β-Hydroxymethyl-(3-methylbutyrate)-6-azaandrost-4-en-3-one (Compound 27)

Melting Point: 137°–138° C. Anal. Calcd. for $C_{24}H_{37}NO_3 \cdot H_2O$; C, 71.07; H, 9.69; N, 3.45. Found: C, 70.82; H, 9.69; N, 3.46.

Example 28

17β-Hydroymethyl-(2,2-diphenylacetate)-6-azaandrost-4-en-3-one (Compound 28)

Melting Point: 200°–201° C. Anal. Calcd. for $C_{33}H_{39}NO_3 \cdot ¼H_2O$; C, 78.93; H, 7.93; N, 2.79. Found: C, 79.14; H, 7.97; N, 2.79.

Example 29

17β-N-2-(3-N-Methylpyrrole)ethyl-carbamoyl-6-azaandrost-4-en-3-one (Compound 29)

Melting Point: 134°–136° C. Anal. Calcd. for $C_{26}H_{37}N_3O_2 \cdot ½H_2O$; C, 72.19; H, 8.85; N, 9.71. Found: C, 71.88; H, 8.77; N, 9.60.

Example 30

17β-N-(4-Trifluoromethyl)methyl-carbamoyl-6-azaandrost-4-en-3-one (Compound 30)

Melting Point: 160°–168° C. Anal. Calcd. for $C_{27}H_{33}N_2O_2F_3 \cdot ¼H_2O$; C, 67.69; H, 7.05; N, 5.85. Found: C, 67.75; H, 7.09; N, 5.86.

Example 31

17β-N-methylenecyclohexyl-carbamoyl-6-azaandrost-4-en-3-one (Compound 31)

Melting Point: 172°–174° C. Anal. Calcd. for $C_{26}H_{40}N_2O_2 \cdot ¾H_2O$; C, 73.28; H, 9.82; N, 6.57. Found: C, 73.03; H, 9.88; N, 6.54.

Example 32

17β-N-(1,1-Dimethyl)-2-(4-flourophenyl)ethyl-carbamoyl-6-azaandrost-4-en-3-one (Compound 32)

Melting Point 144–148° C. Anal. Calcd. for $C_{29}H_{39}N_2O_2F$; C, 74.63; H, 8.43; N, 6.01. Found: C, 74.66; H, 8.48; N, 5.92.

Example 33

17β-(1-Oxo-1(4-isopropoxyphenyl)methyl)-6-azaandrost-4-en-3-one (Compound 33)

Melting Point: >260° C. Anal. Calcd. for $C_{28}H_{37}NO_3 \cdot \frac{2}{3}H_2O$; C, 75.13; H, 8.63; N, 3.13. Found: C, 75.24; H, 8.57; N, 3.13.

Example 34

17β-N-(Dicyclohexyl)methyl-carbamoyl-6-azaandrost-4-en-3-one (Compound 34)

Melting Point: 245°–246° C. Anal. Calcd. for $C_{32}H_{50}N_2O_2$; C, 77.68; H, 10.19; N, 5.66. Found: C, 77.54; H, 10.20; N, 5.60.

Example 35

17β-N-(1-Phenyl)ethyl-carbamoyl-6-azaandrost-4-en-3-one (Compound 35)

Melting Point: 160°–177° C. Anal. Calcd. for $C_{27}H_{36}N_2O_2 \cdot H_2O$; C, 73.94; H, 8.73; N, 6.39. Found: C, 73.95; H, 8,72; N, 6.37.

Example 36

17β-N-(4-Decyl)phenyl-carbamoyl-6-azaandrost-4-en-3-one (Compound 36)

Melting Point: 151°–154° C. Anal. Calcd. for $C_{35}H_{52}N_2O_2 \cdot H_2O$; C, 76.32; H, 9.88; N, 5.09. Found: C, 75.99; H, 9.62; N, 5.06.

Example 37

17β-N-(4-Benzyl)piperidyl-carbamoyl-6-azaandrost-4-en-3-one (Compound 37)

Melting Point: 250°–251° C. Anal. Calcd. for $C_{31}H_{42}N_2O_2 \cdot \frac{1}{4}H_2O$; C, 77.70; H, 8.94; N, 5.85. Found: C, 77.39; H, 8.88; N, 6.00.

Example 38

17β-Hydroxymethyl-(1-adamantylcarboxylate)-6-azaandrost-4-en-3-one (Compound 38)

Melting Point: >275° C. Anal. Calcd. for $C_{30}H_{43}NO_3$; C, 77.38; H, 9.31; N, 3.01. Found: C, 77.05; H, 9.20; N, 3.07.

Example 39

17β-N-Myrantyl-carbamoyl-6-azaandrost-4-en-3-one (Compound 39)

Melting Point: 182°–185° C. (foams). Anal. Calcd. for $C_{29}H_{44}N_2O_2 \cdot \frac{3}{4}H_2O$; C, 74.71; H, 9.84; N, 6.01. Found: C, 74.69; H, 9.78; N, 6.00.

Example 40

17β-N-(-2,4,6-Trimethyl)phenyl-carbamoyl-6-azaandrost-4-en-3-one (Compound 40)

Melting Point: 243°–251° C. Anal. Calcd. for $C_{28}H_{38}N_2O_2 \cdot 2TFA$; C, 58.00; H, 6.08; N, 4.23. Found: C, 59.62; H, 6.73; N, 4.73.

Example 41

17β-N-Hydroxy-N-t-butyl-carbamoyl-6-azaandrost-4-en-3-one (Compound 41)

Melting Point: 252°–254° C. (decomp.). Anal. Calcd. for $C_{23}H_{36}N_2O_3$; C, 71.10; H, 9.34; N, 7.21. Found: C, 71.03; H, 9.39; N, 7.20.

Example 42

17β-N-(2,4-Difluoro)benzyl-carbamoyl-6-azaandrost-4-en-3-one (Compound (42)

Melting Point: 134°–137° C. Anal. Calcd. for $C_{26}H_{32}N_2O_2F_2 \cdot H_2O$; C, 67.80; H, 7.44; N, 6.08. Found: C, 67.70; H, 7.25; N, 6.09.

Example 43

17β-(1-Oxo-3,3-diphenylpropyl)-6-azaandrost-4-en-3-one (Compound 43)

Melting Point: 106° C. (shrinks). FAB mass spec. for $C_{33}H_{39}NO_2$; 481.68 Found: 482 MH$^+$

Example 44

17β-N-(2-Chloro-5-trifluoromethyl)phenyl-carbamoyl-6-azaandrost-4-en-3-one (Compound 44)

Melting Point: 173°–174° C. Anal. Calcd. for $C_{26}H_{30}N_2O_2ClF_3$; C, 63.09; H, 6.11; N, 5.66. Found: C, 62.88; H, 6.48; N, 5.62.

Example 45

17β-N-(2,2-Diphenyl-1-methyl)ethyl-carbamoyl-6-azaandrost-4-en-3-one (Compound 45)

Melting Point: >240° C. Anal. Calcd. for $C_{34}H_{42}N_2O_2 \cdot \frac{1}{4}H_2O$; C, 79.26; H, 8.31; N, 5.44. Found: C, 79.17; H, 8.35; N, 5.46.

Example 46

17β-N-(2,6-Dimethyl-4-bromo)phenyl-carbamoyl-6-azaandrost-4-en-3-one (Compound 46)

Melting Point: >256° C. Anal. Calcd. for $C_{27}H_{35}N_2O_2Br \cdot \frac{1}{3}H_2O$; C, 64.15; H, 7.11; N, 5.54. Found: C, 64.30; H, 7.10; N, 5.53.

Example 47

17β-N-Bis-(4-chlorophenyl)methyl-carbamoyl-6-azaandrost-4-en-3-one (Compound 47)

Melting Point: 188°–194° C. Anal. Calcd. for $C_{32}H_{36}N_2O_2Cl_2 \cdot \frac{1}{4}H_2O$; C, 69.67; H, 6.58; N, 5.08. Found: C, 69.51; H, 6.56; N, 5.02.

Example 48

17β-N-(2,6-Dimethyl-4-t-butyl)phenyl-carbamoyl-6-azaandrost-4-en-3-one (Compound 48)

Melting Point: 203° C. (shrinks). Anal. Calcd. for $C_{31}H_{44}N_2O_2 \cdot \frac{5}{4}H_2O$; C, 74.58; H, 9.39; N, 5.61. Found: C, 74.59; H, 9.30; N, 5.62.

Example 49

17β-N-(2,6-Dibromo-4-isopropyl)phenyl-carbamoyl-6-azaandrost-4-en-3-one (Compound 49)

Melting Point: 182° C. (foams). Anal. Calcd. for $C_{28}H_{36}N_2O_2Br_2 \cdot \frac{1}{3}H_2O$; C, 56.20; H, 6.18; N, 4.68. Found: C, 56.08; H, 6.24; N, 4.61.

Example 50

17β-N-(2,5-Ditrifluoromethyl)phenyl-carbamoyl-6-azaandrost-4-en-3-one (Compound 50)

Melting Point: 144° C. (shrinks). Anal. Calcd. for $C_{27}H_{30}N_2O_2F_6 \cdot \frac{2}{3}H_2O$; C, 59.99; H, 5.84; N, 5.18. Found: C, 60.06; H, 6.10; N, 5.01.

Example 51

17β-N-(4-t-Butyl)cyclohexyl-carbamoyl-6-azaandrost-4-en-3-one (Compound 51)

Melting Point: 229°–231° C. Anal. Calcd. for $C_{29}H_{46}N_2O_2 \cdot \frac{1}{4}H_2O$; C, 75.85; H, 10.21; N, 6.10. Found: C, 75.72; H, 10.22; N, 6.08.

Example 52

17β-N-(2-Bromo)phenyl-carbamoyl-6-azaandrost-4-en-3-one (Compound 52)

Melting Point: >280° C. Anal. Calcd. for $C_{25}H_{31}N_2O_2Br$; C, 63.69; H, 6.63; N, 5.94. Found: C, 63.56; H, 6.67; N, 5.90.

Example 53

17β-N-(2-Phenyl)phenyl-carbamoyl-6-azaandrost-4-en-3-one (Compound 53)

Melting Point: >280° C. Anal. Calcd. for $C_{31}H_{36}N_2O_2 \cdot 2H_2O$; C, 73.78; H, 7.99; N, 5.55. Found: C, 73.62; H, 7.17; N, 5.47.

Example 54

17β-N-(2,6-Diethyl-3,5-dichloro)phenyl-carbamoyl-6-azaandrost-4-en-3-one (Compound 54)

Melting Point: >250° C. Anal. Calcd. for $C_{29}H_{39}N_2O_2Cl_2 \cdot H_2O$; C, 65.04; H, 7.53; N, 5.23. Found: C, 65.38; H, 7.49; N, 5.25.

Example 55

17β-N-(2,6-Diethyl-3-chloro)phenyl-carbamoyl-6-azaandrost-4-en-3-one (Compound 55)

Melting Point: 230°–232° C. Anal. Calcd. for $C_{29}H_{39}N_2O_2Cl \cdot \frac{1}{4}H_2O$; C, 71.44; H, 8.17; N, 5.75. Found: C, 71.41; H, 8.20; N, 5.75.

Example 56

17β-N-(2-t-Butyl)phenyl-carbamoyl-6-azaandrost-4-en-3-one (Compound 56)

Melting Point: 174°–180° C. Anal. Calcd. for $C_{29}H_{40}N_2O_2 \cdot \frac{1}{2}H_2O$; C, 76.11; H, 9.03; N, 6.12. Found: C, 76.12; H, 9.02; N, 6.14.

Example 57

17.6-N-(3,5-Ditrifluoromethyl)phenyl-carbamoyl-6-azaandrost-4-en-3-one (Compound 57)

Melting Point: 194° C. (shrinks). Anal. Calcd. for $C_{27}H_{30}N_2O_2F_6 \cdot \frac{1}{3}H_2O$; C, 60.67; H, 5.78; N, 5.24. Found: C, 60.72; H, 5.82; N, 5.03.

Example 58

17β-N-(2,4,6-Trichloro)phenyl-carbamoyl-6-azaandrost-4-en-3-one (Compound 58)

Melting Point: >250° C. Anal. Calcd. for $C_{25}H_{29}N_2O_2Cl_3 \cdot \frac{1}{3}H_2O$; C, 60.55; H, 5.89; N, 5.65. Found: C, 60.52; H, 5.93; N, 5.65.

Example 59

17β-N-(3,5-Tetramethyl)cyclohexyl-carbamoyl-6-azaandrost-4-en-3-one (Compound 59)

Melting Point: 193°–195° C. Anal. Calcd. for $C_{29}H_{46}N_2O_2Br_2 \cdot H_2O$; C, 73.68; H, 10.24; N, 5.93. Found: C, 73.72; H, 10.34; N, 5.99.

Example 60

17β-(1-Oxo-1-((2,4,6-tri-i-propyl)phenyl)methyl)-6-azaandrost-4-en-3-one (Compound 60)

Melting Point: >230° C. Anal. Calcd. for $C_{34}H_{49}NO_2 \cdot \frac{1}{2}H_2O$; C, 79.64; H, 9.82; N, 2.73. Found: C, 79.53; H, 9.57; N, 2.73.

Example 61

17β-N-(2-Bromo-5-trifluoromethyl)phenyl-carbamoyl-6-azaandrost-4-en-3-one (Compound 61)

Melting Point: 170°–190° C. (decomp.). Anal. Calcd. for $C_{26}H_{30}N_2O_2BrF_3$; C, 57.89; H, 5.61; N, 5.19. Found: C, 57.83; H, 5.63; N, 5.15.

Example 62

17β-N-(2-t-Butyl-6-methyl)phenyl-carbamoyl-6-azaandrost-4-en-3-one (Compound 62)

Melting Point: 190°–220° C. (decomp.). FAB mass spec. for $C_{30}H_{42}N_2O_2$; 462.68 Found: 463 MH$^+$

Example 63

17β-N-(1-Methyl-1-phenyl)ethyl-carbamoyl-6-azaandrost-4-en-3-one (Compound 63)

Melting Point: 156° C. (shrinks). Anal. Calcd. for $C_{28}H_{38}N_2O_2 \cdot \frac{1}{2}H_2O$; C, 75.81; H, 8.86; 6.31. Found: C, 75.90; H, 8.84; N, 6.30.

Example 64

17β-N-1-(4-Chlorophenyl)cyclopentyl-carbamoyl-6-azaandrost-4-en-3-one (Compound 64)

Melting Point: 186°–189° C. Anal. Calcd. for $C_{30}H_{39}N_2O_2Cl$; C, 72.77; H, 7.94; N, 5.66. Found: C, 72.54; H, 7.92; N, 5.63.

Example 65

17β-N-(1-(4-Chlorophenyl)-2-methyl)propyl-carbamoyl-6-azaandrost-4-en-3-one (Compound 65)

Melting Point: 177°–179° C. Anal. Calcd. for $C_{29}H_{39}N_2O_2Cl \cdot \frac{1}{4}H_2O$; C, 71.43; H, 8.17; N, 5.75. Found: C, 71.43; H, 8.20; N, 5.79.

Example 66

17β-N-(1,1-Di-4-chlorophenyl)ethyl-carbamoyl-6-azaandrost-4-en-3-one (Compound 66)

Melting Point: 186°–194° C. Anal. Calcd. for $C_{33}H_{38}N_2O_2Cl_2$; C, 70.00; H, 6.78; N, 4.96; Cl, 12.54. Found: C, 69.89; H, 6.84; N, 4.92; Cl, 12.41.

Example 67

17β-N-(1-Phenyl-1-(4-t-butyl)phenyl)methyl-carbamoyl-6-azaandrost-4-en-3-one (Compound 67)

Melting Point: 188°–192° C. Anal. Calcd. for $C_{36}H_{46}N_2O_2 \cdot \frac{1}{4}H_2O$; C, 79.59; H, 8.63; N, 5.16. Found: C, 79.52; H, 8.67; N, 5.10.

Example 68

17β-(1-Oxo-1-(2-norbornyl)methyl)-azaandrost-4-en-3-one (Compound 68)

Melting Point: 128° C. (shrinks). High res. mass spec. for $C_{26}H_{37}NO_2$; 396.2903 Found: 396.2911 MH$^+$

Example 69

17β-N-(2,6-Dibromo-4-chloro)phenyl-carbamoyl-6-azaandrost-4-en-3-one (Compound 69)

Melting Point: 240°–244° C. (decomp.). Anal. Calcd. for $C_{25}H_{29}N_2O_2Br_2Cl.\frac{1}{2}H_2O$; C, 50.57; H, 5.09; N, 4.72. Found: C, 50.41; H, 4.94; N, 4.62.

Example 70

17β-N-(2,6-Diethyl-4-bromo)phenyl-carbamoyl-6-azaandrost-4-en-3-one (Compound 70)

Melting Point: 212°–216° C. Anal. Calcd. for $C_{29}H_{39}N_2O_2Br$; C, 66.01; H, 7.46; N, 5.31; Br, 15.16. Found: C, 65.94; H, 7.46; N, 5.29; Br, 15.24.

Example 71

17β-N-(2-Bromo-4-t-butyl)phenyl-carbamoyl-6-azaandrost-4-en-3-one (Compound 71)

Melting Point: >250° C. Anal. Calcd. for $C_{29}H_{39}N_2O_2Br$; C, 66.01; H, 7.46; N, 5.31; Br, 15.16. Found: C, 65.91; H, 7.42; N, 5.31; Br, 15.09.

Example 72

17β-N-(2-Chloro-4-t-butyl)phenyl-carbamoyl-6-azaandrost-4-en-3-one (Compound 72)

Melting Point: 235°–246° C. (decomp.). Anal. Calcd. for $C_{29}H_{39}N_2O_2Cl$; C, 71.44; H, 8.16; N, 5.74; Cl, 7.27. Found: C, 71.52; H, 8.19; N, 5.75; Cl, 7.26.

Example 73

17β-N-(1-t-Butyl-1-(4-t-butylphenyl))methyl-carbamoyl-6-azaandrost-4-en-3-one (Compound 73)

Melting Point: 198°–204° C. Anal. Calcd. for $C_{34}H_{50}N_2O_2Br_2$; C, 76.72; H, 9.75; N, 5.26. Found: C, 76.81; H, 9.65; N, 5.26.

Example 74

17β-N-(5-Bromo-2-t-butyl)phenyl-carbamoyl-6-azaandrost-4-en-3-one (Compound 74)

Melting Point: 192°–195° C. Anal. Calcd. for $C_{29}H_{39}N_2O_2Br.H_2O$; C, 63.85; H, 7.58; N, 5.14. Found: C, 63.75; H, 7.58; N, 5.16.

Example 75

17β-N-(5-Chloro-2-t-butyl)phenyl-carbamoyl-6-azaandrost-4-en-3-one (Compound 75)

Melting Point: 235°–246° C. (decomp.). Anal. Calcd. for $C_{29}H_{39}N_2O_2Cl.H_2O$; C, 69.51; H, 8.25; N, 5.59. Found: C, 69.34; H, 8.22; N, 5.98.

Example 76

17β-N-(2,6-Diethyl)phenyl-carbamoyl-6-azaandrost-4-en-3-one (Compound 76)

Melting Point: 190°–196° C. Anal. Calcd. for $C_{29}H_{40}N_2O_2.\frac{3}{8}H_2O$; C, 76.49; H, 9.02; N, 6.15. Found: C, 76.59; H, 9.01; N, 6.10.

Example 77

17β-N-(4-Bromo-2-t-butyl)phenyl-carbamoyl-6-azaandrost-4-en-3-one (Compound 77)

Melting Point: 162° C. (foams). Anal. Calcd. for $C_{29}H_{39}N_2O_2Br$; C, 66.01; H, 7.46; N, 5.31. Found: C, 65.94; H, 7.60; N, 5.20.

Example 78

17β-N-(2-t-Butyl-5-cyano)phenyl-carbamoyl-6-azaandrost-4-en-3-one (Compound 78)

Melting Point: >300° C. Anal. Calcd. for $C_{30}H_{39}N_3O_2.\frac{3}{4}H_2O$; C, 73.96; H, 8.38; N, 8.63. Found: C, 74.11; H, 8.48; N, 8.68.

Example 79

17β-N-(2-(O-4-Tolyl)-5-trifluoromethyl)phenyl-carbamoyl-6-azaandrost-4-en-3-one (Compound 79)

Melting Point: 134°–142° C. Anal. Calcd. for $C_{33}H_{37}N_2O_3F_3.\frac{1}{3}$i-propanol; C,69.95; H6.58;N,4.94. Found: C, 69.61; H, 6.86; N, 4.73.

Example 80

17β-N-(2-(O-2-Methoxyphenyl)-5-trifluoromethyl))phenyl-carbamoyl-6-azaandrost-4-en-3-one (Compound 80)

Melting Point: 132°–142° C. FAB mass spec. for $C_{33}H_{37}N_2O_4F_3$; 582.67 Found: 583 $MH^+$

Example 81

17β-N-(2-(O-4-Chlorophenyl)-5-trifluoromethl)phenyl-carbamoyl-6-azaandrost-4-en-3-one (Compound 81)

Melting Point: 132°–142° C. Anal. Calcd. for $C_{32}H_{34}N_2O_3ClF_3.\frac{1}{3}$i-propanol$.\frac{1}{2}H_2O$; C, 64.65; H, 6.14; N, 4.57. Found: C,64.74; H,6.23; N,4.58.

Example 82

17β-N-(2-Nitro-4-butyl)phenyl-carbamoyl-6-azaandrost-4-en-3-one (Compound 82)

Melting Point: >265° C. Anal. Calcd. for $C_{29}H_{39}N_3O_4$; C, 70.56; H, 7.96; N, 8.51. Found: C, 70.42; H, 7.98; N, 8.42.

Example 83

17β-N-(2-(O-Phenyl)-5-(1,1-dimethyl)propyl)-phenyl-carbamoyl-6-azaandrost-4-en-3-one (Compound 83)

Melting Point: 147°–152° C. Anal. Calcd. for $C_{36}H_{46}N_2O_3.\frac{1}{2}H_2O$; C, 76.70; H, 8.40; N, 4.97. Found: C, 76.55; H, 8.39; N, 4.95.

Example 84

17β-N-(2-Ethyl-4-cyano)phenyl-carbamoyl-6-azaandrost-4-en-3-one (Compound 84)

Melting Point: >250° C. Anal. Calcd. for $C_{28}H_{35}N_3O_2$; C, 75.47; H, 7.92; N, 9.43. Found: C, 75.26; H, 7.95; N, 9.35.

Example 85

17β-N-(2-Ethylsulfonyl-5-trifluoromethyl)phenyl-carbamoyl-6-azaandrost-4-en-3-one (Compound 85)

Melting Point: >250° C. Anal. Calcd. for $C_{28}H_{35}N_2O_4F_3S.H_2O$; C, 58.93; H, 6.54; N, 4.91. Found: C, 58.87; H, 6.54; N, 4.89.

Example 86

17β-N-(3.5-Di-t-butyl)phenyl-carbamoyl-6-azaandrost-4-en-3-one (Compound 86)

Melting Point: 212°–216° C. Anal. Calcd. for $C_{33}H_{48}N_2O_2$; C, 77.49; H, 9.61; N, 5.48. Found: C, 77.59; H, 9.57; N, 5.53.

Example 87

17β-N-(2-t-Butyl-5-trifluoromethyl)phenyl-carbamoyl-6-azaandrost-4-en-3-one (Compound 87)

A. 4-Trifluoromethyl-α,α-dimethylbenzyl alcohol

To magnesium turnings (30.2 g, 1.24 mol) in THF (30 mL) is added 1,2-dibromoethane (0.7 mL) followed by dropwise addition, over 1 h, of 4-bromotrifluoromethylbenzene (200 g, 0.89 mol) dissolved in THF (700 mL). The reaction is heated occasionally to maintain a gentle reflux and is stirred 45 min after the addition is complete. The dark reaction mixture is then cooled in an ice bath and acetone (103 g, 1.78 mol) added dropwise. After stirring an additional 1.5 h the reaction is carefully quenched with aqueous saturated $NaHSO_4$, ethyl acetate added, the organics dried over $MgSO_4$, concentrated and purified by silica gel chromatography (9:1 to 3:2, hexane to ethyl acetate) to give 4-trifluoromethyl-$\alpha,\alpha$-dimethylbenzyl alcohol of sufficient purity to carry to the next step; yield: 114 g (63%).

B. 4-Trifluoromethyl-$\alpha,\alpha$-dimethylbenzyl chloride

The alcohol from step A above (54 g, 0.27 mol) is treated with ethereal HCl (1.3 L, 1M) followed by anhydrous zinc chloride (53 mL, 1M in ether) and the reaction allowed to stir for 22 h at room temperature. The reaction is then washed with water, aqueous 2 N NaOH, dried over $MgSO_4$, concentrated and purified by silica gel chromatography (8:1 hexane to ethyl acetate) to give 4-trifluoromethyl-$\alpha,\alpha$-dimethylbenzyl chloride of sufficient purity to carry to the next step; yield: 50.5 g (85%).

C. 4-Trifluoromethyl-t-butylbenzene

To a toluene solution of dimethylzinc (150 mL, 2.0M, 0.30 mol) at −78° C. is added a $CH_2Cl_2$ solution of titanium tetrachloride (150 mL, 1.0 M, 0.15 mol) and after stirring for 30 min 4-trifluoromethyl-$\alpha,\alpha$-dimethylbenzyl chloride (83.3 g, 0.373 mol) in $CH_2Cl_2$ (100 mL) is added dropwise over 20 min. After the addition is complete the reaction is allowed to warm to −40° C. over 1.5 h. After an additional 2 h at −40° C. the brown reaction mixture is carefully poured onto crushed ice, extracted with $CH_2Cl_2$ (2×500 mL), the combined extracts dried over $MgSO_4$ and concentrated to give 4-trifluoromethyl-t-butylbenzene; yield: 60.3 g (80%). Anal. Calcd. for $C_{11}H_{13}F_3$: C, 65.32; H, 6.48. Found: C, 65.11; H, 6.38.

D. 2-t-Butyl-5-trifluoromethyinitrobenzene

To a solution of 4-trifluoromethyl-t-butylbenzene (25.6 g, 126 mmol) in $H_2SO_4$ (143 mL) at 0° C. is added a mixture of $HNO_3$ (90%, 42 mL) and $H_2SO_4$ (87 mL). After 30 min the ice bath is removed and the reaction stirred for 2.5 h further.

The yellow mixture is then poured onto crushed ice and extracted with ethyl acetate, the ethyl acetate washed with 2N NaOH and water, dried ($MgSO_4$) and concentrated to a dark oil. Purification by silica gel chromatography (14:1 hexane to ethyl acetate) gives 2-t-butyl-5-trifluoromethylnitrobenzene of sufficient purity to carry to the next step; yield: 18.0 g (58%).

E. 2-t-Butyl-5-trifluoromethylaniline

A solution of 2-t-butyl-5-trifluoromethylnitrobenzene (26.0 g, 105 mmol) in ethanol (95%, 100 mL) is treated with 10% Pd/C (2 g) and placed under a hydrogen atmosphere (40 psi) on a Parr apparatus for 1.5 h. The mixture is filtered, concentrated and purified by silica gel chromatography (7:1 hexane to ethyl acetate) to give 2-t-butyl-5-trifluoromethylaniline as an oil; yield: 20.2 g (89%).

Anal. Calcd. for $C_{11}H_{14}F_3N$: C, 60.80; H, 6.50; N, 6.45. Found: C, 60.89; H, 6.50; N, 6.51.

F. 17β-N-(2-t-Butyl-5-trifluoromethyl)phenyl-carbamoyl-6-azaandrost-4-en-3-one

The aniline prepared above is reacted with the acid chloride of 17β-carboxy-6-t-butoxycarbonyl-6-azaandrost-4-en-3-one (prepared as in example 1, part G) and deprotected as in example 1, part G to give: 7β-N-(2-t-butyl-5-trifluoro)phenyl-carbamoyl-6-azaandrost-4-en-3-one.

Melting Point: 186°–190° C. Anal. Calcd. for $C_{30}H_{39}N_2O_2F_3$: C,69.73; H,7.61; N,5.42. Found: C, 69.45; H, 7.66; N, 5.38.

Examples 88–92

Following the general procedure of example 1, part G, wherein the hydrochloride salt of the amine is reacted with the acid chloride in the presence of sodium bicarbonate or by reaction with the free base or metal salt of the amine, for preparation of amides as the Z substituent in compounds of formula (I); the general procedure of example 2 for preparation of ketones as the Z substituent in compounds of formula (I); and the general procedure of example 3 for preparation of compounds where $Z=CH_2OCOR^5$ and $Z=CH_2OCO_2R^5$ in compounds of formula (I) the following compounds were prepared:

Example 88

17β-N-(2-t-Butyl-5-phenyl)phenyl-carbamoyl-6-azaandrost-4-en-3-one (Compound 88)

Melting Point: 207°–209° C. Anal. Calcd. for $C_{35}H_{44}N_2O_2 \cdot \frac{1}{4}H_2O$; C, 79.43; H, 8.48; N, 5.29. Found: C, 79.53; H, 8.54; N, 5.31.

Example 89

17β-Hydroxymethyl-(menthylcarbonate)-6-azaandrost-4-en-3-one (Compound 89)

Melting Point: 152°–155° C. Anal. Calcd. for $C_{30}H_{47}NO_4 \cdot H_2O$; C, 71.53; H, 9.81; N, 2.78. Found: C, 71.63; H, 9.79; N, 2.80.

Example 90

17β-Hydroxymethyl-(phenylcarbonate)-6-azaandrost-4-en-3-one (Compound 90)

Melting Point: 247°–249° C. (decomp.). Anal. Calcd. for $C_{26}H_{33}NO_4 \cdot \frac{1}{8}CH_2Cl_2$; C, 72.27; H, 7.72; N, 3.23. Found: C, 71.82; H, 7.77; N, 3.25.

Example 91

17β-N-(2-t-Butyl-5-(N-methyl methylsulfonamide phenyl-6-azaandrost-4-en-one (Compound 91)

Melting Point: 290°–292° C. (decomp.). Anal. Calcd. for $C_{31}H_{45}N_3O_4S$; C, 65.40; H, 8.23; N, 7.38. Found: C, 65.41; H, 8.23; N, 7.42.

Example 92

17β-(3-Nitro-4-t-butyl)phenyl-carbamoyl-6-azaandrost-4-en-3-one (Compound 92)

Melting Point: 214°–217° C. Anal. Calcd. for $C_{29}H_{39}N_3O_4$; C, 69.30; H, 8.02; N, 8.36. Found: C, 69.11; H, 8.09; N, 8.12.

Example 93

17β-N-(2,6-Di-i-propyl)phenyl-carbamoyl-6-azaandrost-1,4-dien-3-one (Compound 93)

A. 17β-Carbomethoxy-6-t-butoxycarbonyl-6-azaandrost-1,4-dien-3-one

A solution of 17β-carbomethoxy-6-t-butoxycarbonyl-6-azaandrost-4-en-3-one (2.00 g, 4.63 mmol), prepared in example 1, part E, in dioxane (50 mL) is treated with 2,3-dichloro-5,6-dicyano-1,4-benzoquinone (DDQ, 1.37 g, 6.02 mmol) and p-nitrophenol (10 mg). The reaction is heated to reflux for 2 hrs, poured into ice water (150 mL), extracted with ethyl acetate (3×100 mL), extracts washed with saturated aqueous $NaHSO_3$, 2N NaOH, saturated aqueous NaCl, dried over $MgSO_4$, concentrated and chromatographed on silica gel (40% ethyl acetate/hexanes) to give crude 17β-carbomethoxy-6-t-butoxycarbonyl-6-azaandrost-1,4-dien-3-one as a tan solid of sufficient purity to carry on to the following steps; yield: 1.53 g (76%).

B. 17β-N-(2,6-Di-i-propyl)phenyl-carbamoyl-6-t-butoxycarbonyl-6-azaandrost-1,4-dien-3-one A sample of crude 17β-carbomethoxy-6-t-butoxycarbonyl-6-azaandrost-1,4-dien-3-one (0.90 g, 2.20 mmol), prepared in part A, is demethylated as in example 1, part F and then coupled via the acid chloride (described in example 1, part G) with the lithium artion of 2,6-di-i-propylaniline to give after chromatography (30–50% ethyl acetate/hexanes), 17β-N-(2,6-di-i-propyl)phenyl-carbamoyl-6-t-butoxycarbonyl-6-azaandrost-1,4-dien-3-one as a white foam; yield: 0.210 g (16%).

C. 17β-N-(2,6-Di-i-propyl)phenyl-carbamoyl-6-azaandrost-1,4-dien-3-one

A sample of 17β-N-(2,6-di-i-propyl)phenyl-carbamoyl-1–6-t-butoxycarbonyl-6-azaandrost-1,4-dien-3-one (188 mg, 0.320 mmol), prepared in part B above, is treated with trifluoroacetic acid as described in example 1, part G above to give, after chromatography (50% ethyl acetate/hexanes to 5% methanol/chloroform), 17β-N-(2,6-di-i-propyl)phenyl-carbamoyl-6-azaandrost-1,4-dien-3-one as a white solid; yield: 98 mg (62%); m.p. 273–276° C. Anal. Calcd. for $C_{31}H_{42}N_2O_2.H_2O$; C, 75.73; H, 8.81; N, 5.69. Found: C, 75.84; H, 8.95; N, 5.68.

Example 94

17β-N-(2,6-Di-i-propyl)phenyl-carbamoyl-6-azaandrost-4-methyl-1,4-dien-3-one (Compound 94)

A. 17β-Carbomethoxy-6-t-butoxycarbonyl-6-azaandrost-4-methyl-1,4-dien-3-one

A solution of 17β-carbomethoxy-6-t-butoxycarbonyl-6-azaandrost-1,4-dien-3-one (2.57 g, 5.98 mmol), prepared in example 93, part A in methylene chloride (60 mL) containing anhydrous $K_2CO_3$ (8.03 g, 58 mmol) at 0° C. is treated with bromine (6.1 mmol) dissolved in methylene chloride (12 mL). After 30 min the mixture is filtered, washed with 10% aqueous $NaHSO_3$, dried over $Na_2SO_4$ and concentrated to a foam. This material is dissolved in dimethylformamide (20 mL), treated with phenyltdimethyltin (2.0 mL, 11.4 mmol) and lithium chloride (180 mg, 4.3 mmol), heated to 130° C. and treated with $PdCl_2(PPh_3)2$ (400 mg, 0.57 mmol). After 1.5 hr the reaction is allowed to cool to room temperature, filtered through Celite, poured into water, the water extracted with ethyl acetate (3×30 mL), extracts washed with water (3×100 mL) and 1% aqueous ammonia (2×100 mL), dried over $Na_2SO_4$, concentrated and chromatographed (5–10% ethyl acetate/methylene chloride) to give 17β-carbomethoxy-6-t-butoxycarbonyl-6-azaandrost-4-methyl-1,4-dien-3-one; yield: 1.25 g (47%).

B. 17β-N-(2,6-Di-i-propyl)phenyl-carbamoyl-6-azaandrost-4-methyl-1,4-dien-3-one

A sample of crude 17β-carbomethoxy-6-t-butoxycarbonyl-6-azaandrost-4-methyl-1,4-dien-3-one (0.45 g, 1.01 mmol), prepared in part A, is hydrolized as in example 1, part F and then coupled with 2,6-di-i-propylaniline as described in example 93, part B, deprotected as in example 1, part G, to give after chromatography (2.5–10% methanol/methylene chloride), 17β-N-(2,6-di-i-propyl)phenyl-carbamoyl-6-azaandrost-4-methyl-1,4-dien-3-one as a white powder; yield: 70 mg (14%); m.p. 181°–184° C. Anal. Calcd. for $C_{32}H_{44}N_2O_2.\frac{1}{4}H_2O$; C, 77.93; H, 9.09; N, 5.67. Found: C, 77.81; H, 9.12; N, 5.58.

Example 95

17β-(N-i-Propyl-N-(N-i-propylcarbamoyl))-carbamoyl-6-azaandrost-4-en-3-one (Compound 95)

A solution of 17β-carboxy-6-t-butoxycarbonyl-6-azaandrost-4-en-3-one (500 mg, 1.2 mmol), example 1, part F, is dissolved in methylene chloride (70 mL), treated with diisopropyl carbodiimide (0.21 mL, 1.3 mmol) and stirred at room temperature for 20 hrs. The reaction mixture is then concentrated, the solid dissolved in ethyl acetate (70 mL), the ethyl acetate washed with saturated aqueous $NaHCO_3$ (2×70 mL), 1N HCl (3×70 mL), saturated aqueous NaCl (70 mL), dried over $Na_2SO_4$, and concentrated to a yellow foam. Chromatography on silica gel (50% ethyl acetate/hexanes) gives 17β-(N-i-propyl-N-(N-i-propylcarbamoyl))-carbamoyl-6-t-butoxycarbonyl-6-azaandrost-4-en-3-one as a white foam; yield: 600 mg (65%). FAB mass spec. for $C_{31}H_{49}N_3O_5$; 543.75 Found: 544 MH$^+$ This material is deprotected with TFA as in example 1, part G to give, after crystallization from acetonitrile, 17β-(N-i-propyl-N-(N-i-propylcarbamoyl))-carbamoyl-6-azaandrost-4-en-3-one as a white solid; yield: 220 mg (64%); m.p. 162° C. (decomp.).

Anal. Calcd. for $C_{26}H_{41}N_3O_3.H_2O$; C, 67.64; H, 9.39 N, 9.10. Found: C, 67.58; H, 9.42; N, 9.09.

Example 96

17β-(N-cyclohexyl-N-(N-cyclohexylcarbamoyl))-carbamoyl-6-azaandrost-4-en-3-one (Compound 96)

Prepared as described in example 95.

Melting Point: 186°–187° C. Anal. Calcd. for $C_{32}H_{49}N_3O_3.\frac{1}{4}H_2O$; C, 72.76; H, 9.44; N, 7.95. Found: C, 72.74; H, 9.45; N, 7.68.

Example 97

17β-Aminomethyl-(aceteamide)-6-azaandrost-4-en-3-one (Compound 97)

A. 17β-Azidomethyl-6-t-butoxycarbonyl-6-azaandrost-4-en-3-one

A solution of 17β-hydroxymethyl-6-t-butoxycarbonyl-6-azaandrost-4-en-3-one (2.03 g, 5.04 mmol) prepared in example 3, part 15, in dichloromethane (50 mL) is treated with triethylamine (0.88 mL, 6.3 mmol), DMAP (0.155 g, 1.27 mmol) and methanesulfonyl chloride (0.43 mL, 5.6 mmol). After 3 hrs, the reaction is diluted with dichloromethane (50 mL), washed with 1N HCl, saturated aqueous NaCl and dried over $MgSO_4$. Concentration gives a white foam which is dissolved in dimethylformamide (50 mL), treated with sodium azide (0.94 g, 14.5 mmol) and heated to 75° C. for 16 hrs. The reaction is poured into ethyl acetate, washed with water (5×100 mL), dried over $MgSO_4$, concentrated and chromatographed on silica gel (20% ethyl acetate/hexane) to give 17β-azidomethyl-6-t-butoxycarbonyl-6-azaandrost-4-en-3-one as a white foam of sufficient purity to carry on to the next step.

B. 17β-Aminomethyl-(acetamide)-6-azaandrost-4-en-3-one

A sample of the azide from step A above (20 mg, 50 mmol) is dissolved in 1:1 ethanol/tetrahydrofuran (2 mL), treated with 10% Pd(C) (3.2 mg) and placed under a hydrogen atmosphere for 10 min. The reaction is filtered, concentrated, dissolved in dichloromethane (2 mL) and treated with pyridine (0.1 mL) and acetic arthydride (0.06 mL). After 64 hrs the reaction is diluted with dichloromethane, dried over $Na_2SO_4$, concentrated and chromatographed on silica gel (ethyl acetate) to give 17β-aminomethyl-(acetamide)-6-t-butoxycarbonyl-6-azaandrost-4-en-3-one which is deprotected with TFA as in example 1, part G to give 17β-aminomethyl-(acetamide)-6-azaandrost-4-en-3-one as a white solid; yield: 3 mg (17%). FAB mass spec. for $C_{21}H_{32}N_2O_2$; 344.5. Found: 345 MH$^+$.

Example 98

17β-Aminomethyl-(1-adamantylurea-6-azaandrost-4-en-3-one (Compound 98)

A sample of the azide from example 97, part A (100 mg, 230 mmol) is dissolved in 1:2 ethanol/tetrahydrofuran (6 mL), treated with 10% Pd(C) (60 mg) and placed under a hydrogen atmosphere for 1 hr. The reaction is filtered, concentrated, dissolved in tetrahydrofuran and treated with 1-adamantylisocyanate at room temperature for 6 days. The reaction is concentrated and chromatographed on silica gel (40–70% ethyl acetate/hexanes) to give 17β-aminomethyl-(1-adamantylurea)-6-t-butoxycarbonyl-6-azaandrost-4-en-3-one which is deprotected with TFA as in example 1, part G to give 17β-aminomethyl-(1-adamantylurea)-6-azaandrost-4-en-3-one as a white solid; yield: 47 mg (35%); m.p. 227°–229° C. (foams.). Anal. Calcd. for $C_{30}H_{45}N_3O_2.H_2O$; C, 72.40; H, 9.52; N, 8.44. Found: C, 72.37; H, 9.42; N, 8.46.

Example 99–148

Following the general procedure of example 1, part G, wherein the hydrochloride salt of the amine is reacted with the acid chloride in the presence of sodium bicarbonate or by reaction with the free base or metal salt of the amine, for preparation of amides as the Z substituent in compounds of formula (I); the general procedure of example 3 for preparation of compounds where $Z=CH_2OCONR^{14}R^{15}$ in compounds of formula (I); the general procedure of example 8 and 11 in WO 93/13124 for preparation of compounds of formula (I), where $R^3=Cl$ and Me respectively, the following compounds were prepared. Novel amines used to prepare compounds of formula (I) where the Z substituent is an amide were prepared as described in example 87 above or by the method of Stille, J. K. *Pure Appl. Chem.*, 57, 1771 (1985). When either $R^{14}$ or $R^5$ is an aryl substituted cycloalkyl residue the amine may be prepared by Curtius rearrangement of the corresponding acid, where available, or by the method of He, X. et al, *J. Med. Chem.*, 36, 1188 (1993), i.e. by reacting the corresponding cycloalkanone with the appropriate aryl Grignard reagent followed by conversion of the resulting alcohol to the amine by treatment with sodium azide and trifluoroacetic acid followed by reduction of the azide with lithium aluminum hydride. Aryl substituted cyclopropylamines are prepared by rodium catalyzed insertion of the appropriate aryl-α-diazo-ester (prepared by the method of Baum, J. S. et al, *Synthetic Comm.*, 17, 1709 (1987))into the appropriate olefin (as described by Davies, H. W. et al, *Tetrahedron Lett.*, 30, 5057 (1989)) followed by saponification of the ester and Curtius rearrangement of the acid to give the desired amine.

Example 99

17β-Hydroxymethyl-(2,6-diidopropylphenylcarbamate)-6-azaandrost-4-en-3-one (Compound 99)

Melting Point: 161°–163° C. Anal. Calcd. for $C_{32}H_{46}N_2O_3.H_2O$; C, 73.25; H, 9.22; N, 5.34. Found: C, 73.08; H, 9.19; N, 5.29.

Example 100

17β-N-(4-t-Butyl-2-triflouoromethyl)phenyl-carbamoyl-6-azaandrost-4en-3-one (Compound 100)

Melting Point: 186°–190° C. Anal. Calcd. for $C_{30}H_{39}N_2O_2F_3.¼H_2O$; C, 69.14; H, 7.64; N, 5.38. Found: C, 69.12; H, 7.65; N, 5.35.

Example 101 cl 17β-N-1-(2,4-Dichlorophenyl)cyclopropyl-carbamoyl-6-azaandrost-4en-3-one (Compound 101)

Melting Point: 160°–180° C. (decomp.). Anal. Calcd. for $C_{28}H_{34}N_2O_2Cl_2.½H_2O$; C, 65.86; H, 6.91; N, 5.49. Found: C, 69.64; H, 6.89; N, 5.47.

Example 102

17β-N-1-(3-Trifluoromethylphenyl)cyclopentyl-carbamoyl-6-azaandrost-4en-3-one (Compound 102)

Melting Point: 156°–159° C. Anal. Calcd. for $C_{31}H_{39}N_2O_2F_3.H_2O$; C, 68.11; H, 7.56; N, 5.12. Found: C, 67.79; H, 7.48; N, 5.02.

Example 103

17β-N-(1-Ethyl-1-phenyl)propyl-carbamoyl-6-azaandrost-4en-3-one (Compound 103)

Melting Point: 157°–160° C. Anal. Calcd. for $C_{30}H_{42}N_2O_2.¾H_2O$; C, 75.67; H, 9.20; N, 5.88. Found: C, 75.80; H, 9.09; N, 5.78.

Example 104

17β-N-1-(4-Flourophenyl)cyclopentyl-carbamoyl-6-azaandrost-4en-3-one (Compound 104)

Melting Point: 220°–223° C. Anal. Calcd. for $C_{30}H_{39}N_2O_2F.½H_2O$; C, 73.71; H, 8.17; N, 5.75. Found: C, 73.89; H, 8.27; N, 5.74.

1-Amino-1-(4-fluorophenyl)cyclopentane: $^{13}C$ NMR ($CDCl_3$) δ 5 162.8, 159.6, 45.2, 127.0, 126.8, 114.8, 114.5, 63.5, 41.5, 23.4.

Example 105

17β-N-(2-t-Butyl-5-N,N-diethylcarbamoyl)phenyl-carbamoyl-6-azaandrost-4-en-3-one (Compound 105)

Melting Point: 167°–169° C. Anal. Calcd. for $C_{34}H_{49}N_3O_3.½H_2O$; C, 73.34; H, 9.05; N, 7.55. Found: C, 73.41; H, 9.10; N, 7.42.

Example 106

17β-N-(4-Trifluoromethylphenyl)cyclopentyl-carbamoyl-6-azaandrost-4-en-3-one (Compound 106)

Melting Point: 201°–203° C. Anal. Calcd. for $C_{31}H_{39}N_2O_2F_3.½H_2O$; C, 69.51; H, 7.55; N, 5.09. Found: C, 69.25; H, 7.50; N, 5.21.

1-Amino-1-(4-trifluoromethylphenyl)cyclopentane: $^{13}C$ NMR ($CDCl_3$) 8 153.6, 153.5, 128.5, 128.1,126.0, 125.7, 125.1,125.1,125.0, 125.0, 122.4, 63.8, 41.7, 23.5.

Example 107

17β-N-(3-Cyano)phenyl-carbamoyl-6-azaandrost-4-en-3-one (Compound 107)

Melting Point: 202°–208° C. Anal. Calcd. for C$_{26}$H$_{31}$N$_{3}$O$_{2}$.H$_{2}$O; C, 71.70; H, 7.64; N, 9.65. Found: C, 71.88; H, 7.69; N, 9.48.

Example 108

17β-N-(4-t-Butyl)phenyl-carbamoyl-6-azaandrost-4-en-3-one (Compound 108)

Melting Point: 304°–307° C. Anal. Calcd. for C$_{29}$H$_{40}$N$_{2}$O$_{2}$.¼H$_{2}$O; C, 76.86; H, 9.00; N, 6.18. Found: C, 76.83; H, 8.92; N, 6.54.

Example 109

17β-N-1-(4-Flourophenyl)cyclohexyl-carbamoyl-6-azaandrost-4-en-3-one (Compound 109)

Melting Point: 167°–169° C. Anal. Calcd. for C$_{31}$H$_{41}$N$_{2}$O$_{2}$F.⅓H$_{2}$O; C, 74.66; H, 8.42; N, 5.61. Found: C, 74.72; H, 8.43; N, 5.53.

Example 110

17β-N-1-(2,2-Dimethyl)indanyl-carbamoyl-6-azaandrost-4en-3-one (Compound 110)

Melting Point: 178°–182° C. Anal. Calcd. for C$_{30}$H$_{40}$N$_{2}$O$_{2}$; C, 75.99; H, 8.82; N, 5.91. Found: C, 75.64; H, 8.84; N, 5.88.

Example 111

17β-N-1-(4-Methoxyphenyl)cyclohexyl-carbamoyl-6-azaandrost-4en-3-one (Compound 111)

Melting Point: 167°–169° C. Anal. Calcd. for C$_{32}$H$_{44}$N$_{2}$O$_{3}$.¾H$_{2}$O; C, 74.17; H, 8.85; N, 5.41. Found: C, 73.95; H, 8.92; N, 5.38.

Example 112

17β-N-(2-Phenyl-5-triflouromethyl)phenyl-carbamoyl-6-azaandrost-4en-3-one (Compound 112)

Melting Point: 304°–306° C. Anal. Calcd. for C$_{32}$H$_{35}$N$_{2}$O$_{2}$F$_{3}$; C, 71.62; H, 6.57; N, 5.22. Found: C, 71.56; H, 6.56; N, 5.27.

Example 113

17β-N-(2-Methoxy-5-chloro)phenyl-carbamoyl-6-azaandrost-4en-3-one (Compound 113)

Melting Point: 237°–238° C. Anal. Calcd. for C$_{26}$H$_{33}$N$_{2}$O$_{3}$Cl.¾H$_{2}$O; C, 66.37; H, 7.39; N, 5.95. Found: C, 66.17; H, 7.31; N, 5.96.

Example 114

17β-N-(2-Carboethoxy)phenyl-carbamoyl-6-azaandrost-4en-3-one (Compound 114)

Melting Point: 282°–286° C. Anal. Calcd. for C$_{28}$H$_{36}$N$_{2}$O$_{4}$; C, 72.39; H, 7.81; N, 6.03. Found: C, 72.15; H, 7.88; N, 6.10.

Example 115

17β-N-1-(4-Methoxyphenyl)cyclopentyl-carbamoyl-6-azaandrost-4en-3-one (Compound 115)

Melting Point: 160° C. Anal. Calcd. for C$_{31}$H$_{42}$N$_{2}$O$_{3}$.H$_{2}$O; C, 73.19; H, 8.72; N, 5.51. Found: C, 73.26; H, 8.67; N, 5.46.

Example 116

17β-N-(2,5-bis(Trifluoromethyl))phenyl-carbamoyl-6-azaandrost-4en-3-one (Compound 116)

Melting Point: 142°–146° C. Anal. Calcd. for C$_{28}$H$_{32}$N$_{2}$O$_{2}$F$_{6}$; C, 61.96; H, 5.95; N, 5.16. Found: C, 61.70; H, 5.99; N, 5.07.

Example 117

17β-N-(2-t-Butyl-5-trifluoromethyl)phenyl-carbamoyl-6-azaandrost-4en-3-one (Compound 117)

Melting Point: 188° C. Anal. Calcd. for C$_{31}$H$_{41}$N$_{2}$O$_{2}$F$_{3}$.¾H$_{2}$O; C, 68.42; H, 7.87; N, 5.15. Found: C, 68.31; H, 7.71; N, 5.08.

Example 118

17β-N-(2,5-Di-t-butyl)phenyl-carbamoyl-6-azaandrost-4en-3-one (Compound 118)

Melting Point: 168°–176° C. Anal. Calcd. for C$_{34}$H$_{50}$N$_{2}$O$_{2}$.½H$_{2}$O; C, 77.37; H, 9.74; N, 5.31. Found: C, 77.32; H, 9.74; N, 5.28.

Example 119

17β-N-(2,5-Diethoxy)phenyl-carbamoyl-6-azaandrost-4-en-3-one (Compound 117)

Melting Point: 277°–279° C. Anal. Calcd. for C$_{29}$H$_{40}$N$_{2}$O$_{4}$.¼H$_{2}$O; C, 71.80; H, 8.41; N, 5.77. Found: C, 71.50; H, 8.45; N, 5.74.

Example 120

17β-N-(2-t-Butyl-5-(4-chlorophenyl))phenyl-carbamoyl-6-azaandrost-4-en-3-one (Compound 120)

Melting Point: 214°–216° C. Anal. Calcd. for C$_{35}$H$_{43}$N$_{2}$O$_{2}$Cl.1 ½H$_{2}$O; C, 71.71; H, 7.91; N, 4.78. Found: C, 71.46; H, 7.88; N, 4.81.

Example 121

17β-N-1-(4-t-Butylphenyl)cyclopentyl-carbamoyl-6-azaandrost-4-en-3-one (Compound 121)

Melting Point: 222°–232° C. Anal. Calcd. for C$_{34}$H$_{48}$N$_{2}$O$_{2}$.¾H$_{2}$O; C, 77.01; H, 9.41; N, 5.28. Found: C, 77.05; H, 9.46; N, 5.25.

1-Amino-1-(4-t-butylphenyl)cyclopentane: $^{13}$C NMR (CDCl$_{3}$) δ 148.9, 146.4, 125.1, 125.0, 124.9, 63.7, 41.2, 34.3, 31.4, 31.3, 23.6.

Example 122

17β-N-1-(4-t-Butylphenyl)cyclohexyl-carbamoyl-6-azaandrost-4-en-3-one (Compound 122)

Melting Point: 203° C. Anal. Calcd. for C$_{35}$H$_{50}$N$_{2}$O$_{2}$; C, 76.60; H, 9.55; N, 5.10. Found: C, 76.43; H, 9.59; N, 5.05.

1-Amino-1-(4-t-butylphenyl)cyclohexane: $^{13}$C NMR (CDCl$_{3}$) δ 148.8, 146.8, 125.0, 124.6, 53.4, 39.2, 34.2, 31.2, 25.7, 22.4.

Example 123

17β-N-(2-Benzoyl)phenyl-carbamoyl-6-azaandrost-4-en-3-one (Compound 123)

Melting Point: 290°–294° C. Anal. Calcd. for C$_{32}$H$_{36}$N$_{2}$O$_{3}$.½H$_{2}$O; C, 76.01; H, 7.38; N, 5.54. Found: C, 76.19; H, 7.35; N, 5.47.

Example 124

17β-N-1-(3,4-Methylenedioxyphenyl)cyclohexyl-carbamoyl-6-azaandrost-4-en-3-one (Compound 124)

Melting Point: 192° C. Anal. Calcd. for C$_{32}$H$_{42}$N$_{2}$O$_{4}$.¾H$_{2}$O; C, 72.22; H, 8.24; N, 5.26. Found: C, 72.01; H, 8.25; N, 5.14.

1-Amino-1-(3,4-methylenedioxyphenyl)cyclohexane: $^{13}$C NMR (CDCl$_3$) δ 147.5, 145.6, 144.1, 117.9, 107.6, 106.1, 100.7, 53.6, 39.5, 25.6, 22.4.

Example 125

17β-N-1-(4-Chlorophenyl)cyclopentyl-carbamoyl-6-azaandrost-4-methyl-4-en-3-one (Compound 125)

Melting Point: 166° C. High res. mass spec. for C$_{31}$H$_{41}$N$_2$O$_2$Cl; 509.2935. Found: 509.2941.

Example 126

17β-N-(2,5-bis(Trifluoromethyl))phenyl-carbamoyl-6-azaandrost-4-chloro-4-en-3-one (Compound 126)

Melting Point: 148°–154° C. Anal. Calcd. for C$_{27}$H$_{29}$N$_2$O$_2$ClF$_6$; C, 57.48; H, 5.19; N, 4.98. Found: C, 57.43; H, 5.21; N, 4.91.

Example 127

17β-N-(2-t-Butyl-5-trifluoromethyl)phenyl-carbamoyl-6-azaandrost-4-chloro-4-en-3-one (Compound 127)

Melting Point: 174°–178° C. Anal. Calcd. for C$_{30}$H$_{38}$N$_2$O$_2$ClF$_3$; C, 65.37; H, 6.95; N, 5.08. Found: C, 65.49; H, 7.01; N, 5.05.

Example 128

17β-N-(2-Methoxy-5-t-butyl)phenyl-carbamoyl-6-azaandrost-4-en-3-one (Compound 128)

Melting Point: 170°–175° C. Anal. Calcd. for C$_{30}$H$_{42}$N$_2$O$_3$.H$_2$O; C, 72.55; H, 8.93; N, 5.64. Found: C, 72.50; H, 8.94; N, 5.69.

Example 129

17β-N-(2-Fluoro-5-trifluoromethyl)phenyl-carbamoyl-6-azaandrost-4-en-3-one (Compound 129)

Melting Point: 167°–170° C. Anal. Calcd. for C$_{26}$H$_{30}$N$_2$O$_2$F$_4$.¾H$_2$O; C, 63.47; H, 6.45; N, 5.69. Found: C, 63.46; H, 6.26; N, 5.76.

Example 130

17β-N-(1-(4-Biphenyl)-2,2-diethyl)cyclopropyl-carbamoyl-6-azaandrost-4-en-3-one (Compound 130)

Melting Point: 178°–182° C. Anal. Calcd. for C$_{38}$H$_{48}$N$_2$O$_2$; C, 79.54; H, 8.61; N, 4.88. Found: C, 79.68; H, 8.55; N, 4.86.

1-Amino-1-(1-(4-biphenyl)-2,2-diethyl)cyclopropane: $^{13}$C NMR (CDCl$_3$) δ 144.6, 140.9, 139.1, 128.8, 128.7, 127.1, 127.0, 127.0, 46.9, 33.2, 25.6, 24.1, 22.3, 11.6, 10.5.

Example 131

17β-N-(1-(4-Trifluoromethylphenyl)-2,2-diethyl)cyclopropyl-carbamoyl-6-azaandrost-4en-3-one (Compound 131)

Melting Point: 176°–182° C. Anal. Calcd. for C$_{33}$H$_{43}$N$_2$O$_2$F$_3$.⅓H$_2$O; C, 70.44; H, 7.82; N, 4.98. Found: C, 70.44; H, 7.83; N, 4.97.

1-Amino-1-(1-(4-trifluoromethylphenyl)-2,2-diethyl)cyclopropane: $^{13}$C NMR (CDCl$_3$) δ 149.5, 149.5, 129.7, 128.8, 128.4, 126.1, 126.0, 125.5, 125.5, 125.4, 125.3, 122.5, 46.9, 33.4, 25.6, 24.3, 22.2, 11.5, 10.4.

Example 132

17β-N-3-(2-Carbomethoxy-5-t-butyl)thiophenyl-carbamoyl-6-azaandrost-4en-3-one (Compound 132)

Melting Point: 273°–275° C. Anal. Calcd. for C$_{29}$H$_{40}$N$_2$O$_4$S; C, 67.94; H, 7.86; N, 5.46. Found: C, 67.67; H, 7.90; N, 5.42.

Example 133

17β-N-(2-Phenylsulfonyl)phenyl-carbamoyl-6-azaandrost-4en-3-one (Compound 133)

Melting Point: 175°–180° C. Anal. Calcd. for C$_{31}$H$_{36}$N$_2$O$_4$S.¼H$_2$O; C, 69.31; H, 6.84; N, 5.22. Found: C, 69.18; H, 7.01; N, 5.15.

Example 134

17β-N-(4-Carboethoxy)phenyl-carbamoyl-6-azaandrost-4en-3-one (Compound 134)

Melting Point: 299°–301° C. Anal. Calcd. for C$_{28}$H$_{36}$N$_2$O$_4$.¼H$_2$O; C, 71.69; H, 7.84; N, 5.97. Found: C, 71.74; H, 7.83; N, 5.98.

Example 135

17β-N-(2-(4-t-Butyl)phenyl-5-trifluoromethyl)phenyl-carbamoyl-6-azaandrost-4-en-3-one (Compound 135)

Melting Point: 185°–189° C. Anal. Calcd. for C$_{36}$H$_{43}$N$_2$O$_2$F$_3$; C, 72.95; H, 7.31; N, 4.73. Found: C, 72.84; H, 7.36; N, 4.65.

Example 136

17β-N-1-(4-t-Butylphenyl)cycloheptyl-carbamoyl-6-azaandrost-4-en-3-one (Compound 136)

Melting Point: 190°–194° C. Anal. Calcd. for C$_{36}$H$_{52}$N$_2$O$_2$.¾H$_2$O; C, 77.27; H, 9.65; N, 5.00. Found: C, 77.44; H, 9.66; N, 5.01.

1-Amino-1-(4-t-butylphenyl)cycloheptane: $^{13}$C NMR (CDCl$_3$) 5 148.7, 148.2, 125.0, 124.7, 57.3, 42.9, 34.2, 31.2, 29.7, 23.1.

Example 137

17β-N-(3-Carboxy)phenyl-carbamoyl-6-azaandrost-4-en-3-one (-Compound 137)

Melting Point: 258°–260° C. Anal. Calcd. for C$_{26}$H$_{32}$N$_2$O$_4$.HCl.1 ¼H$_2$O; C, 63.02; H, 7.22; N, 5.65. Found: C, 63.02; H, 7.22; N, 5.62.

Example 138

17β-N-1-(9-Fluorenonyl)-carbamoyl-6-azaandrost-4-en-3-one (Compound 138)

Melting Point: 260°–264° C. Anal. Calcd. for C$_{32}$H$_{34}$N$_2$O$_3$.1¼H$_2$O; C, 74.32; H, 7.11; N, 5.42. Found: C, 74.49; H, 7.12; N, 5.38.

Example 139

17β-N-1-(4-Butylphenyl)cyclohexyl-carbamoyl-6-azaandrost-4-chloro-4-en-3-one (Compound 139)

Melting Point: 158° C. FAB mass spec. for C$_{35}$H$_{49}$N$_2$O$_2$Cl; 565.2. Found: 565.2 M$^+$.

Example 140

17β-N-(2,6-Diethyl-4-(4-chlorophenyl )phenyl-carbamoyl-6-azaandrost-4-en-3-one (Compound 140)

Melting Point: >300° C. Anal. Calcd. for C$_{35}$H$_{43}$N$_2$O$_2$Cl.¼H$_2$O; C, 74.58; H, 7.78; N, 4.97. Found: C, 74.27; H, 7.80; N, 4.97.

Example 141

17β-N-(2-Phenyl)-hydrazidyl-carbamoyl-6-azaandrost-4-en-3-one (Compound 141)

Example 142

17β-N-(2-t-Butylcarbamoyl-5-trifluoromethyl phenyl-carbamoyl-6-azaandrost-4-en-3-one (Compound 142)

Melting Point: 198°–200° C. Anal. Calcd. for $C_{31}H_{40}N_3O_3F_3$; C, 66.53; H, 7.20; N, 7.51. Found: C, 66.41; H, 7.32; N, 7.36.

Example 143

17β-N-4-4-Butylphenyl)tetrahydrothiooyranyl-carbamoyl-6-azaandrost-4-en-3-one (Compound 143)

Melting Point: 197° C. Anal. Calcd. for $C_{34}H_{48}N_2O_2S.\frac{3}{4}H_2O$; C, 72.62; H, 8.87; N, 4.98. Found: C, 72.46; H, 8.97; N, 4.99.

4-Amino-4-(4-t-butylphenyl)tetrahydrothiopyran: $^{13}C$ NMR (CDCl$_3$) δ 149.3, 146.7, 125.3, 124.3, 52.6, 39.8, 34.2, 31.3, 24.3.

Example 144

17β-N-9-(4-t-Butylphenyl)bicyclo[3.3.1]nonyl-carbamoyl-6-azaandrost-4en-3-one (Compound 144)

Melting Point: >260° C. Anal. Calcd. for $C_{38}H_{54}N_2O_2.1\frac{1}{4}H_2O$; C, 76.92; H, 9.60; N, 4.72. Found: C, 76.82; H, 9.63; N, 4.67.

9-Amino-9-(4-t-Butylphenyl)bicyclo[3.3.1]nonane: $^{13}C$ NMR (CDCl$_3$) δ 148.6, 144.8, 125.4, 125.3, 124.7, 124.3, 64.1, 55.4, 38.9, 35.3, 34.2, 31.7, 31.3, 31.3, 29.1, 27.0, 24.4, 21.1, 20.5.

Example 145

17β-N-4-(4-t-Butylphenyl)tetrahydropyranyl-carbamoyl-6-azaandrost-4en-3-one (Compound 145)

Melting Point: 181° C. Anal. Calcd. for $C_{34}H_{48}N_2O_3.\frac{3}{4}H_2O$; C, 74.75; H, 9.13; N, 5.13. Found: C, 74.72; H, 9.11; N, 5.15.

4-Amino-4-(4-t-butylphenyl)tetrahydropyran: $^{13}C$ NMR (CDCl$_3$) δ 149.4, 146.5, 125.3, 124.3, 64.1, 51.2, 38.9, 31.3, 22.4.

Example 146

17β-N-1-(4-Chlorophenylcyclohexyl)-carbamoyl-6-azaandrost-4en-3-one (Compound 146)

Melting Point: 184° C. Anal. Calcd. for $C_{31}H_{41}N_2O_2Cl$; C, 73.13; H, 8.11; N, 5.50. Found: C, 72.74; H, 8.39; N, 5.38.

Example 147

17β-N-(2-t-Butyl-5-(4-t-butyl)phenyl)phenyl-carbamoyl-6-azaandrost-4-en-3-one (Compound 147)

Melting Point: >300 Anal. Calcd. for $C_{39}H_{52}N_2O_2$; C,78.22; H,9.09; N,4.68. Found: C,77.98; H,8.99; N,4.65

Example 148

17β-N-1-(4-Chlorophenyl)cyclopentyl-carbamoyl-6-azaandrost-4-chloro-4-en-3-one (Compound 148)

FAB mass spec. for $C_{30}H_{38}N_2O_2Cl_2$ 529.55 Found: 529.3M$^+$

Melting Point: 193°–195° C. Anal. Calcd. for $C_{25}H_{33}N_3O_2.H_2O$; C, 70.56; H, 8.29; N, 9.87. Found: C, 70.17; H, 8.26; N, 9.87.

Example 149

Pharmaceutical formulations (A) Transdermal System—For 1000 Patches

| Ingredients | Amount |
| --- | --- |
| Active compound | 40 g |
| Silicone fluid | 450 g |
| Colloidal silicon dioxide | 25 g |

The silicon fluid and active compound are mixed together and the colloidal silicon dioxide is added to increase viscosity. The material is then dosed into a subsequently heat sealed polymedc laminate comprised of the following: polyester release liner, skin contact adhesive composed of silicone or acrylic polymers, a control membrane which is a polyolefin (e.g. polyethylene, polyvinyl acetate or polyurethane), and an impermeable backing membrane made of a polyester multilaminate. The resulting laminated sheet is then cut into 10 sq. cm patches.

(B) Oral Tablet—For 1000 Tablets

| Ingredients | Amount |
| --- | --- |
| Active compound | 20 g |
| Starch | 20 g |
| Magnesium Stearate | 1 g |

The active compound and the starch are granulated with water and dried. Magnesium stearate is added to the dried granules and the mixture is thoroughly blended. The blended mixture is compressed into tablets.

(C) Suppository—For 1000 Suppositories

| | Amount |
| --- | --- |
| Active compound | 25 g |
| Theobromine sodium salicylate | 250 g |
| Witepsol S55 | 1725 g |

The inactive ingredients are mixed and melted. The active compound is then distributed in the molten mixture, poured into molds and allowed to cool.

(D) Injection—For 1000 Ampules

| Ingredients | Amount |
| --- | --- |
| Active Compound | 5 g |
| Buffering Agents | q.s. |
| Propylene glycol | 400 mg |
| Water for injection | 600 mL |

The active compound and buffering agents are dissolved in the propylene glycol at about 50° C. The water for injection is then added with stirring and the resulting solution is filtered, filled into ampules, sealed and sterilized by autoclaving.

(E) Capsule—For 1000 Capsules

| Ingredients | Amount |
| --- | --- |
| Active Compound | 20 g |
| Lactose | 450 g |
| Magnesium stearate | 5 g |

The finely ground active compound is mixed with the lactose and stearate and packed into gelatin capsules.

We claim:

1. A compound of formula (I):

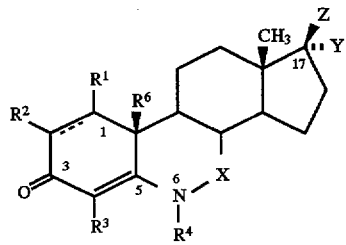

wherein $R^1$ and $R^2$ i) are independently hydrogen or lower alkyl and the bond between the carbons bearing $R^1$ and $R^2$ is a single or a double bond, or ii) taken together are a —$CH_2$— group forming a cyclopropane ring, and the bond between the carbons bearing $R^1$ and $R^2$ is a single bond;

$R^3$ is hydrogen, —$Alk^1$—H (optionally substituted with one or more halogens), lower cycloalkyl, lower cycloalkyl-lower alkyl), halogen, —$(Alk^1)_n$—$CO_2H$, —$(Alk^1)_n$—$CO_2R^7$, —$(Alk^1)_n$—$Ar^1$, —$(Alk^1)_n$—$CONR^8R^9$, —$(Alk^1)_n$—$NR^8R^9$, —$(Alk^1)_n$—$S(O)_rR^7$, —$(Alk^1)_n$—CN, —$(Alk^1)$—OH, —$(Alk^1)_n$—$COR^7$; or —$(Alk^1)_n$—$OR^7$; wherein $Alk^1$ is lower alkylene, lower alkenylene or lower alkynylene, n is 0 or 1, r is 0, 1 or 2, $R^7$ is —$Alk^1$—H, —$(Alk^1)_n$—$Ar^1$ or lower cycloalkyl, $R^8$ and $R^9$ are independently hydrogen, —$Alk^1$—H or lower cycloalkyl, $Ar^1$ is a homocyclic aryl group of 6 to 14 carbons;

$R^4$ is hydrogen, —$Alk^1$—H, lower cycloalkyl, lower cycloalkyl-lower alkyl, —$(Alk^1)_n$—$S(O)_rR^7$, —$(Alk^1)_n$-phthalimidyl, —$(Alk^1)$—$CO_2H$, —$(Alk^1)_n$—$CO_2R^7$, —$(Alk^1)_n$—$COR^7$, —$(Alk^1)_n$—$Ar^1$, —$(Alk^1)_n$-$CONR^8R^9$, —$(Alk^1)_n$—$NR^8R^9$, —$(Alk^1)_n$—OH or —$(Alk^1)_n$—$OR^7$;

X is,

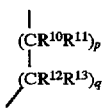

wherein $R^{10}$, $R^{11}$, $R^{12}$ and $R^{13}$ are independently hydrogen or lower alkyl, p and q are independently either 0 or 1; and, i) Y is hydrogen or hydroxy and Z is —$(Alk^2)_n$—$COR^5$, —$(Alk^2)_n$—$CO_2R^5$, —$(Alk^2)_n$—$COSR^5$, —$(Alk^2)_n$—$CONR^{14}R_{15}$, —$(Alk^2)$—$OCO_2R^5$, —$(Alk^2)$—$OCOR^5$, —$(Alk^2)$—$OCONR^{14}R^{15}$, —$(Alk^2)$—$OR^5$, —$(Alk^2)$—$NR^{5'}COR^5$, —$(Alk^2)$—$NR^{5'}CO_2R^5$, —$(Alk^2)$—$NR^5CONR^{14}R^{15}$, —$(Alk^2)_n$—$CONR^5NR^{14}R^{15}$, —$(Alk^2)_n$—$CONR^5CONR^{14}R^{15}$, —$(Alk^2)$—$NR^5CSNR^{14}R^{15}$ or —$(Alk^2)_n$—$CONR^5CSNR^{14}R^{15}$;

wherein $Alk^2$ is $(C_{1-12})$ alkylene, $(C_{2-12})$ alkenylene or $(C_{2-12})$ alkynylene, $R^5$ and $R^{5'}$ are independently hydrogen, —$Alk^1$—H (optionally substituted independently with one or more $CO_2H$, $CO_2R^7$, $Ar^2$, $Ar^3$ or cyano groups), $(Alk^1)_n$-(lower cycloalkyl (optionally substituted independently with one or more —$Alk^1$—H groups)), adamantyl, norbornyl, $Ar^2$, $Ar^3$, (lower cycloalkyl)-$Ar^2$ or (lower cycloalkyl)-$Ar^3$; wherein $Ar^2$ is a homocyclic aromatic group of 6 to 14 carbon ring atoms (optionally substituted independently with one or more —$Alk^2$-H (optionally substituted independently with one or more halogens), —$(Alk^1)_n COR^7$, —$(Alk^1)_n$—OH, —$(Alk^1)_n$—$OR^{16}$, —$(Alk^1)_n$—$Ar^3$, —$(Alk^1)_n$—$CO_2H$, —$(Alk^1)_n$—$CO_2R^7$, $S(O)_rR^7$, $NR^8S(O)_rR^{16}$, $NR^8R^9$, $CONR^8R^9$, lower cycloalkyl, lower alkoxy, —$(Alk^1)_n$—$Ar^1$ (optionally substituted with one or more —$Alk^1$—H or halogen), methylenedioxy, ethylenedioxy, morpholino, thiomorpholino, cyano, nitro or halogens); wherein $R^{16}$ is —$Alk^1$—H (optionally substituted independently with one or more halogens), lower cycloalkyl (optionally substituted independently with one or more halogens, or —$Alk^1$—H (optionally substituted independently with one or more halogens)) or —$(Alk^1)_n$—$Ar^1$ (wherein $Ar^1$ is optionally substituted independently with one or more lower alkoxy, cyano, halogen or —$Alk^1$—H (optionally substituted independently with one or more halogens);

$Ar^3$ is an aromatic group of 5 to 14 ring atoms, at least one of which is O, N or S (optionally substituted independently with one or more —$Alk^1$—H (optionally substituted independently with one or more halogens), lower cycloalkyl, lower alkoxy, $CO_2H$, $CO_2R^7$, —$(Alk^1)_n$—$Ar^1$, cyano or halogen);

$R^{14}$ and $R^{15}$ are a) independently, hydroxy, hydrogen, —$Alk^2$-H, lower alkoxy, —$(Alk^1)_n$-adamantyl, —$(Alk^1)_n$-myrantyl, —$(Alk^1)_n$-norbornyl, —$(Alk^1)_n$-fluorenyl, —$(Alk^1)_n$-fluorenonyl, —$(Alk^1)_n$-indanyl (optionally substituted with one or more —$Alk^1$-H), —$Alk^1$—H (optionally substituted independently with one or more halogens, cyano, cycloalkyl, $SR^5$, $COR^5$, $CONR^5R^7$, $NR^{5'}COR^5$, $NR^{5'}CO_2R^5$, $NR^{5'}CONHR^5$, $CO_2R^5$, $OR^5$, $Ar^2$ or $Ar^3$), $Ar^2$ or $Ar^3$ or a saturated $C_{4-18}$ bicyclic ring or $C_{3-11}$ saturated ring, optionally containing an oxygen or sulfur atom (said rings optionally substituted independently with one or more cyano, $R^{16}$, $Ar^2$ or $Ar^3$);

b) alkylene groups (optionally substituted with one or more $R^7$ groups, taken together with the linking nitrogen to form a 4 to 8 atom heterocyclic group)

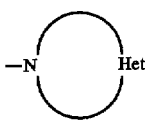

wherein;

Het represents —O—, —CH$_2$—, —S(O)$_r$—,—(NH)— or —(N(Alk$^1$—H))—;

with the proviso that when Z is —(Alk$^2$)$_n$—COR$^5$, —(Alk$^2$)$_n$—CO$_2$R$^5$ or —(Alk$^2$)$_n$-CO-thiopyridyl and R$^5$ is hydrogen, —Alk$^1$—H, lower cycloalkyl, or adamantyl or when Z is —(Alk$^2$)$_n$—CONR$^{14}$R$^{15}$ and R$^{14}$ and R$^{15}$ are a) independently hydrogen, —Alk$^2$-H, lower cycloalkyl, lower alkoxy, adamantyl, —Ar$^1$, benzyl, diphenylmethyl, triphenylmethyl or —(Alk$^1$)$_n$-norbornyl; or b) carbon atoms, optionally substituted with one or more lower alkyl groups, taken together with the linking nitrogen to form a 4 to 8 atom heterocylic ring as herein before defined, Y is hydroxy; or ii) Y is hydrogen and Z is OR$^5$, OCOR$^5$, OCONR$^{14}$R$^{15}$, NR$^{5'}$COR$^5$, NR$^{5'}$CO$_2$R$^5$, NR$^5$CONR$^{14}$R$^{15}$ or NR$^5$CSR$^{14}$R$^{15}$; and iii) Y and Z taken together are =O, =CH—(Alk$^1$)$_n$—COR$^5$, =CH—(Alk$^1$)$_n$—CO$_2$R$^5$ or =CH—(Alk$^1$)$_n$—CONR$^{14}$R$^{15}$;

R$^6$ is hydrogen or methyl;

or a pharmaceutically acceptable salt or solvate thereof.

2. A compound of claim 1 which is a compound of formula (IA), (IB), (IC) or (ID)

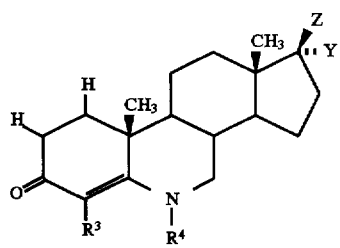 (IA)

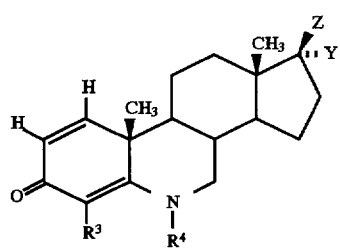 (IB)

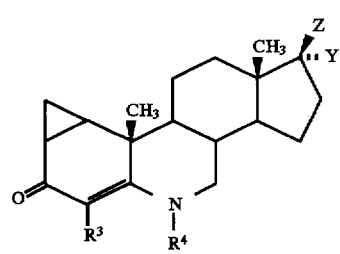 (IC)

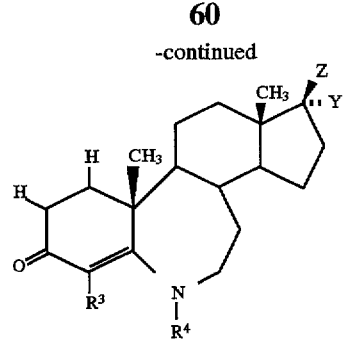 (ID)

3. A compound as claimed in claim 1 wherein R$^3$ is hydrogen, halogen, lower alkyl, lower cycloalkyl or lower cycloalkyl-lower alkyl.

4. A compound as claimed in claim 3 wherein R$^3$ is hydrogen, halogen or lower alkyl.

5. A compound of claim 1 wherein R$^3$ is methyl, ethyl, cyano, iodo, bromo, chloro or dimethylaminomethyl.

6. A compound as claimed in claim 1 wherein R$^4$ is hydrogen, lower alkyl, lower cycloalkyl or lower cycloalkyl-lower alkyl.

7. A compound as claimed in claim 6 wherein R$^4$ is hydrogen or lower alkyl.

8. A compound as claimed in claim 1 wherein R$^4$ is methyl, ethyl, propyl, i-propyl, butyl, i-butylhexyl, 3-hydroxypropyl, propenyl, methylene-cyclopropyl, benzyl, 2-methoxyethyl, 2-acetic acid, 3-proponic acid, 5-pentanoic acid, 6-hexanoic acid, methyl-5-pentanoate, ethyl-6-hexanoate, 3-phthalimidylpropyl and 4-phthalimidylpropyl.

9. A compound according to claim 1 wherein X is —CH$_2$—.

10. A compound as claimed in claim 1 wherein Y is hydrogen and Z is —(Alk$^2$)$_n$—COR$^5$, —(Alk$^2$)$_n$—CONR$^{14}$R$^{15}$, —(Alk$^2$)—OCO$_2$R$^5$, —(Alk$^2$)—OCOR$^5$, —(Alk$^2$)—NR$^{5'}$COR$^5$, —(Alk$^2$)$_n$—CONR$^5$NR$^{14}$R$^{15}$, —(Alk$^2$)—NR$^5$CONR$^{14}$R$^{15}$, or —(Alk$^2$)$_n$—CONR$^5$CONR$^{14}$R$^{15}$.

11. A compound as claimed in claim 10 wherein Z is —COR$^5$, —CONR$^{14}$R$^{15}$, —CH$_2$OCO$_2$R$^5$, —CH$_2$OCOR$^5$, —CH$_2$NR$^{5'}$COR$^5$, —CONR$^5$NR$^{14}$R$^{15}$, —CH$_2$NR$^5$CONR$^{14}$R$^{15}$ or —CONR$^5$CONR$^{14}$R$^{15}$.

12. A compound as claimed in claim 11 wherein Z is —CONR$^{14}$R$^{15}$.

13. A compound as claimed in claim 1 wherein Ar$^1$ is a phenyl group.

14. A compound as claimed in claim 1 wherein Ar$^2$ is a phenyl group optionally substituted independently with one or more —Alk$^2$-H (optionally substituted independently with one or more halogens), —OR$^{16}$, —S(O)$_r$R$^7$, Ar$^1$, methylenedioxy, ethylenedioxy, morpholino, thiomorpholino, cyano, nitro or halogen groups.

15. A compound as claimed in claim 1 wherein R$^{14}$ is hydrogen or hydroxy, and R$^{15}$ is hydrogen, lower cycloalkyl (optionally substituted independently with one or more R$^7$ or Ar$^2$ groups), —(Alk$^1$)-adamantyl, —(Alk$^1$)$_n$-myrantyl, —(Alk$^1$)$_n$-norbornyl, —(Alk$^1$)$_n$-fluorenyl, —(Alk$^1$)$_n$-indanyl, —Alk$^1$—H (optionally substituted independently with one or more lower cycloalkyl, SR$^5$, OR$^5$, Ar$^2$ or Ar$^3$ groups), Ar$^2$ or Ar$^3$; or R$^{14}$ and R$^{15}$ are carbon atoms, optionally substituted with one or more R$^7$ groups, taken together with the linking nitrogen to form a 5 to 7 atom heterocyclic group

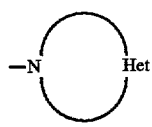

wherein Het represents —CH$_2$—.

16. A compound as claimed in claim 1 wherein Ar$^3$ is an aromatic group of five or six ring atoms, at least one of which is O, N or S, optionally substituted independently with one or more Alk$^1$H groups.

17. A compound as claimed in claim 16 wherein Ar$^3$ is an optionally substituted pyrrolyl, thienyl, furyl or pyridyl group.

18. A compound as claimed in claim 1 wherein R$^5$ is hydrogen, lower alkyl optionally substituted independently with one or more Ar$^2$ groups, (lower alkyl)$_n$-lower cycloalkyl, menthyl, adamantyl, norbornyl or Ar$^2$.

19. A compound as claimed in claim 1 wherein Z is —COR$^5$.

20. A compound which is:

17β-(1-Oxo-2-cyclohexylethyl)-6-azaandrost-4-en-3-one;

17β-(1-Oxo-1-(2,4-difluorophenyl)methyl)-6-azaandrost-4-en-3-one;

17β-(1-Oxo-1-(4-isopropoxyphenyl)methyl)-6-azaandrost-4-en-3-one;

17β-(1-Oxo-3,3-diphenylpropyl)-6-azaandrost-4-en-3-one; or

17β-(1-Oxo-1-(2-norbornyl)methyl)-6-azaandrost-4-en-3-one or a pharmaceutically acceptable salt or solvate thereof.

21. A compound as claimed in claim 1 wherein Z is —CONR$^{14}$R$^{15}$, R$^{14}$ is hydrogen and R$^{15}$ is Ar$^2$ or a C$_{3-11}$ saturated ring, optionally containing an oxygen or sulphur atom (optionally substituted independently with one or more R$^7$ or Ar$^2$ groups).

22. A compound as claimed in claim 1 wherein R$^{15}$ is a group of formula Ar$^{2a}$

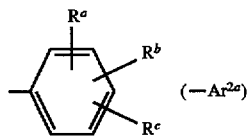

wherein R$^a$ and R$^b$ are independently hydrogen, lower alkyl, trifluoromethyl, halogen or phenyl (optionally substituted with one or more halogens or branched C$_{4-7}$alkyl) and R$^c$ is hydrogen or one or more halogens, or R$^{15}$ is a C$_{3-11}$ saturated ring, optionally containing an oxygen or sulphur atom substituted with a group of formula Ar$^{2a}$.

23. A compound as claimed in claim 1 wherein R$^{15}$ is a group of formula Ar$^{2aa}$

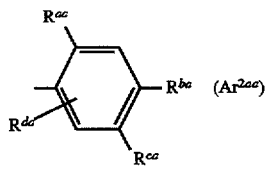

where R$^{aa}$ is branched C$_{4-7}$alkyl, trifluoromethyl or phenyl optionally substituted with one or more halogens; one of R$^{ba}$ and R$^{ca}$ is branched C$_{4-7}$alkyl, trifluoromethyl, halogen or phenyl optionally substituted with one or more halogens, and the other is hydrogen or halogen; and R$^{da}$ is hydrogen or halogen.

24. A compound as claimed in claim 1 which is:

17β-N-((2,6-Di-i-propyl)phenyl)-carbamoyl-6-azaandrost-4-en-3-one

17β-N-(2,4,6-trimethyl)phenyl-carbamoyl-6-azaandrost-4-en-3-one

17β-N-(2-Chloro-5-trifluoromethyl)phenyl-carbamoyl-6-azaandrost-4-en-3-one

17β-N-(2,6-Dimethyl-4-bromo)phenyl-carbamoyl-6-azaandrost-4-en-3-one

17β-N-(2,6-Dimethyl-4-t-butyl)phenyl-carbamoyl-6-azaandrost-4-en-3-one

17β-N-(2,6-Dibromo-4-isopropyl)phenyl-carbamoyl-6-azaandrost-4-en-3-one

17β-N-(2,5-Ditrifluoromethyl)phenyl-carbamoyl-6-azaandrost-4-en-3-one

17β-N-(2-Phenyl)phenyl-carbamoyl-6-azaandrost-4-en-3-one

17β-N-(2,6-Diethyl-3,5-dichloro)phenyl-carbamoyl-6-azaandrost-4-en-3-one

17β-N-(2,6-Diethyl-3-chloro)phenyl-carbamoyl-6-azaandrost-4-en-3-one

17β-N-(2-t-Butyl)phenyl-carbamoyl-6-azaandrost-4-en-3-one

17β-N-(2,4,6-Trichloro)phenyl-carbamoyl-6-azaandrost-4-en-3-one

17β-N-(2-Bromo-5-trifluoromethyl)phenyl-carbamoyl-6-azaandrost-4-en-3-one

17β-N-(2-t-Butyl-6-methyl)phenyl-carbamoyl-6-azaandrost-4-en-3-one

17β-N-1-(4-Chlorophenyl)cyclopentyl-carbamoyl-6-azaandrost-4-en-3-one

17β-N-(2,6-Dibromo-4-chloro)phenyl-carbamoyl-6-azaandrost-4-en-3-one

17β-N-(2,6-Diethyl-4-bromo)phenyl-carbamoyl-6-azaandrost-4-en-3-one

17β-N-(2-Bromo-4-t-butyl)phenyl-carbamoyl-6-azaandrost-4-en-3-one

17β-N-(2-Chloro-4-t-butyl)phenyl-carbamoyl-6-azaandrost-4-en-3-one

17β-N-(5-Bromo-2-t-butyl)phenyl-carbamoyl-6-azaandrost-4-en-3-one

17β-N-(5-Chloro-2-t-butyl)phenyl-carbamoyl-6-azaandrost-4-en-3-one

17β-N-(2,6-Diethyl)phenyl-carbamoyl-6-azaandrost-4-en-3-one

17β-N-(4-Bromo-2-t-butyl)phenyl-carbamoyl-6-azaandrost-4-en-3-one

17β-N-(2-t-Butyl-5-cyano)phenyl-carbamoyl-6-azaandrost-4-en-3-one

17β-N-(2-(O-4-Tolyl)-5-trifluoromethyl)phenyl-carbamoyl-6-azaandrost-4-en-3-one

17β-N-(2-(O-4-Chlorophenyl)-5-trifluoromethyl)phenyl-carbamoyl-6-azaandrost-4-en-3-one 17β-N-(2-Nitro-4-t-butyl)phenyl-carbamoyl-6-azaandrost-4-en-3-one 17β-N-(2-(O-Phenyl)-5-(1,1-dimethyl)propyl)phenyl-carbamoyl-6-azaandrost-4-en-3-one 17β-N-(2-Ethylsulfonyl-5-trifluoromethyl)phenyl-carbamoyl-6-azaandrost-4-en-3-one 17β-N-(3,5-Di-t-butyl)phenyl-carbamoyl-6-azaandrost-4-en-3-one 17β-N-(2-t-Butyl-5-trifluoromethyl)phenyl-carbamoyl-6-azaandrost-4-en-3-one 17β-N-(2-t-Butyl-5-phenyl)phenyl-carbamoyl-6-azaandrost-4-en-3-one 17β-N-(2,6-Di-i-propyl)phenyl-carbamoyl-6-azaandrost-1,4-dien-3-one 17β-N-(2,6-Di-i-propyl)phenyl-carbamoyi-6-azaandrost4-methyl-1,4-dien-3-one 17β-N-1-(4-Trifluoromethylphenyl)cyclopentyl-carbamoyl-6-azaandrost-4-en-3-one 17β-N-1-(4-Fluorophenyl)cyclohexyl-carbamoyl-6azaandrost-4-en-3-one 17β-N-1-(4-Methoxyphenyl)cyclohexyl-carbamoyl-6-azaandrost-4-en-3-one 17β-N-1-(4-Methoxyphenyl)cyclopentyl-carbamoyl-6-azaandrost-4-en-3-one 17β-N-(2,5-bis(Trifluoromethyl))phenyl-carbamoyl-6-azaandrost-4-methyl-4-en-3-one 17β-N-(2t-Butyl-5trifurmethy)phenyl-carbamoyl-6azaandrost4-methyl-4en3-one 17β-N-(2,5-Di-t-butyl)phenyl-carbamoyl-6-azaandrost-4-methyl-4-en-3-one 17β-N-(2-t-Butyl-5-(4-chlorophenyl))phenyl-carbamoyl-6-azaandrost-4-en-3-one 17β-N-1-(4-t-Butylphenyl)cyclopentyl-carbamoyl-6-azaandrost-4-en-3-one 17β-N-1-(4-t-Butylphenyl)cyclohexyl-carbamoyl-6-azaandrost-4-en-3-one 17β-N-1-(4-Chlorophenyl)cyclopentyl-carbamoyl-6-azaandrost-4-methyl-4-en-3-one 17β-N-(2,5-bis(Trifluoromethyl))phenyl-carbamoyl-6-azaandrost-4-chloro-4-en-3-one 17β-N-(2-t-Butyl-5trifurmethyl)phenyl-carbamoyl6azaandrost-4-chloro-4en-3-one 17β-N-1-(4-t-Butylphenyl)cycloheptyl-carbamoyl-6-azaandrost-4-en-3-one 17β-N-1-(4-t-Butylphenyl)cyclohexyl-carbamoyl-6-azaandrost-4-chloro-4-en-3-one 17β-N-(2,6-Diethyl-4-(4-chlorophenyl))phenyl-carbamoyl-6-azaandrost-4-en-3-one 17β-N-4-(4-t-Butylphenyl)tetrahydrothiopyranyl-carbamoyl-6-azaandrost-4-en-3-one 17β-N-9-(4-t-Butylphenyl)bicyclo[3.3.1]nonyl-carbamoyl-6-azaandrost-4-en-3-one 17β-N-4-(4-t-Butylphenyl)tetrahydropyranyl-carbamoyl-6-azaandrost-4-en-3-one 17β-N-1-(4-Chlorophenyl)cyclohexyl-carbamoyl-6-azaandrost-4-en-3-one 17β-N-(2-t-Butyl-5-(4-t-butyl)phenyl)phenyl-carbamoyl-6-azaandrost-4-en-3-one or 17β-N-1-(4-Chlorophenyl)cyclopentyl-carbamoyl-6-azaandrost-4-chloro-4-en-3-one or a pharmaceutically acceptable salt or solvate thereof.

25. 17β-N-(2-t-Butyl-5-trifluoromethyl)phenyl-carbamoyl-6-azaandrost-4-en-3-one or a pharmaceutically acceptable salt or solvate thereof.

26. A compound of formula (I)

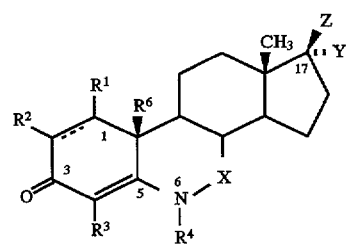

wherein

R¹ and R² are,
i) independently hydrogen or lower alkyl and the bond between the carbons bearing $R^1$ and $R^2$ is a single or a double bond, or
ii) taken together are a —CH₂— group to form a cyclopropane ring, and the bond between the carbons bearing $R^1$ and $R^2$ is a single bond;

$R^3$ is hydrogen or lower alkyl;

$R^4$ is hydrogen or lower alkyl'

X is,

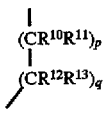

wherein $R^{10}$, $R^{11}$, $R^{12}$ and $R^{13}$ are independently hydrogen or lower alkyl, p and q are independently either 0 or 1;

Y is hydrogen; and

Z is —COR⁵, CONR¹⁴R¹⁵, —CH₂OCO₂R⁵, —CH₂OCOR⁵, —CH₂NR⁵'COR⁵, —CONR⁵NR¹⁴R¹⁵, —CH₂NR⁵CONR¹⁴R⁵, or —CON⁵CONR¹⁴R¹⁵ wherein $R^5$ and $R^{5'}$ are independently hydrogen, lower alkyl optionally substituted independently with one or more Ar² groups (lower alkyl)n-lower cycloalkyl, menthyl, adamantyl, norbornyl or Ar²;

Ar² is phenyl group optionally substituted independently with one or more —Alk-H (optionally substituted independently with one or more halogens), —OR¹⁶, —S(O)ᵣR⁷, phenyl, methylenedioxy, ethylenedioxy, morpholino, thiomorpholino, cyano, nitro or halogen groups;

Alk is lower alkylene, lower alkenylene or lower alkynylene;

n is 0 or 1;

r is 0, 1 or 2;

R⁷ is —Alk-H, —(Alk)ₙ-phenyl or lower cycloalkyl;

R⁶ is —Alk-H (optionally substituted independently with one or more halogens), lower cycloalkyl (optionally substituted independently with one or more halogens, or —Alk-H (optionally substituted independently with one or more halogens)) or —(Alk)n-phenyl (wherein phenyl is optionally substituted independently with one or more lower alko, cyano, halogen or —Alk-H groups (optionally substituted independently with one or more halogens));

R¹⁴ is hydrogen or hydroxy, and R⁵ is hydrogen, lower cycloalkyl, (optionally substituted independently with one or more R⁷ or Ar² groups), —(Alk)-adamantyl, —(Alk)ₙ-myrantyl, —(Alk)ₙ-norbornyl, —(Alk)$_n$-fluorenyl, —(Alk)$_n$-indanyl, —Alk-H (optionally substituted independently with one or more lower cycloalkyl, SR$^5$, OR$^5$, Ar$^2$ or Ar$^3$ groups), Ar$^2$ or Ar$^3$, or R$^{14}$ and R$^{15}$ taken together with the linking nitrogen form a pyrrolidinyl, piperidinyl or perhydroazepinyl ring optionally substituted with one or more R$^7$ groups; Ar$^3$ is a pyrrolyl, thienyl, furyl or pyridyl group optionally substituted independently with one or more Alk-H groups; with the provisos that when Z is COR$^5$, R$^5$ is substituted lower alkyl, lower alkyl lower cycloalkyl, menthyl, norbornyl or Ar$^2$;

when Z is CONR$^{14}$R$^{15}$ and R$^{15}$ is hydrogen, —Alk-H, lower cycloalkyl, lower lakoxy, adamantyl, phenyl, benzyl, diphenylmethyl, triphenylmethyl or —(Alk)$_n$-norbornyl, R$^{14}$ is hydroxy; and when Z is CONR$^{14}$R$^{15}$ and R$^{14}$ andR$^{15}$ taken together with the linking nitrogen form a pyrrolidinyl, piperidinyl or pergydroazepinyl ring, said ring is substituted with one or more lower alkenyl, lower alkynyl, —(Alk)$_n$-phenyl or lower cycloalkyl groups; or a pharmaceutically acceptable salt or solvate thereof.

27. A compound of formula (I)

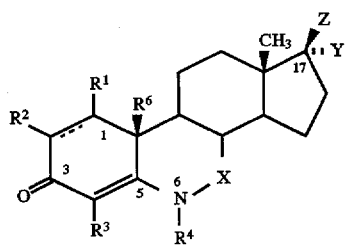

wherein:

R$^1$ and R$^2$ are,
  i) independently hydrogen or lower alkyl and the bond between the carbons bearing R$^1$ and R$^2$ is a single or a double bond, or
  ii) taken together are a —C H$_2$— group to form a cyclopropane ring, and the bond between the carbons bearing R$^1$ and R$^2$ is a single bond;

R$^3$ is hydrogen, —Alk$^1$—H , —Alk$^1$—H substituted with one or more halogens, lower cycloalkyl, lower cycloalkyl-lower alkyl, halogen, —(Alk$^1$)$_n$—CO$_2$H, —(Alk$^1$)$_n$—CO$_2$R$^7$, —(Alk$^1$)$_n$—Ar$^1$, —(Alk$^1$)$_n$—CONR$^8$R$^9$, —(Alk$^1$)$_n$—NR$^8$R$^9$, —(Alk$^1$)$_n$—S(O)$_r$R$^7$, —(Alk$^1$)$_n$—CN, —(Alk$^1$)—OH or —(Alk$^1$)$_n$—OR$^7$;
wherein Alk$^1$ is lower alkylene, lower alkenylene or lower alkynylene, n is 0or 1, r is0,1or 2, R$^7$ is —Alk$^1$—H, —(Alk$^1$)$_n$—Ar$^1$or lower cycloalkyl, R$^8$ and R$^9$ are independently hydrogen, —Alk$^1$—H or lower cycloalkyl, Ar$^1$ is a homocyclic aryl group of 6 to 14 carbons;

R$^4$ is hydrogen, —Alk$^1$—H, lower cycloalkyl, lower cycloalkyl-lower alkyl, —(Alk$^1$)$_n$—S(O)$_r$R$^7$, —(Alk$^1$)$_n$-phthalimidyl, (—Alk$^1$)—CO$_2$H, —(Alk$^1$)$_n$—CO$_2$R$^7$, —(Alk$^1$)$_n$—Ar$^1$, —(Alk$^1$)$_n$—CONR$^8$R$^9$, —(Alk$^1$)$_n$—NR$^8$R$^9$, —(Alk$^1$)$_n$—OH or —(Alk$^1$)$_n$—OR$^7$;

X is,

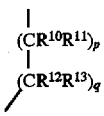

wherein
R$^{10}$, R$^{11}$, R$^{12}$ and R$^{13}$ are independently hydrogen or lower alkyl, p and q are independently either 0or 1;

Y and Z are,
i) Y is hydrogen or hydroxy and
Z is —(Alk$^2$)$_n$—COR$^5$, —(Alk$^2$)$_n$—CO$_2$R$^5$, —(Alk$^2$)$_n$—COSR$^5$, —(Alk$^2$)$_n$—CONR$^{14}$R$^{15}$, —(Alk$^2$)—OCOR$^5$, —(Alk$^2$)—OCONR$^{14}$R$^{15}$, —(Alk$^2$)—OR$^5$, —(Alk$^2$)—NR$^5$COR$^5$, —(Alk$^2$)—NR$^5$CO$_2$R$^5$, —(Alk$^2$)—NR$^5$CONR$^{14}$R$^{15}$, —(Alk$^2$)—CONR$^5$NR$^{14}$R$^{15}$, —(Alk$^2$)$_n$—CONR$^5$CONR$^{14}$R$^{15}$, (—Alk$^2$-)NR$^5$CSNR$^{14}$R$^{15}$ or —(Alk$^2$)$_n$—CONR$^5$CSNR$^{14}$R$^{15}$;
wherein Alk$^2$ is (C$_{1-12}$) alkylene, (C$_{2-12}$) alkenylene or (C$_{2-12}$) alkynylene, R$^5$ is hydrogen, —Alk$^1$—H, —(Alk$^1$)$_n$-(lower cycloalkyl), adamantyl, —(Alk$^1$)$_n$—Ar$^2$, —(Alk$^1$)$_n$—Ar$^3$, (lower cycloalkyl)$_n$Ar$^2$, (lower cycloalkyl)$_n$Ar$^3$or —Alk$^1$-substituted independently with one or more CO$_2$H, CO$_2$R$^7$, Ar$^2$ or Ar$^3$ groups;
wherein Ar$^2$ is an aromatic group of 6 to 14 carbon ring atoms, optionally substituted with one or more Alk$^1$, Alk$^1$ substituted with one or more halogens, —(Alk$^1$)$_n$-OH, —(Alk$^1$)$_n$—OR$^7$, —(Alk$^1$)$_n$—CO$_2$H, —(Alk$^1$)$_n$—CO$_2$R$^7$, S(O)$_r$R$^7$or NR$^8$R$^9$, lower cycloalkyl, lower alkoxy, —(Alk$^1$)$_n$—Ar$^1$, methylenedioxy, ethylenedioxy, morpholino, thiomorpholino, cyano or halogen groups;

Ar$^3$ is an aromatic group of 5 to 14 ring atoms, at least one of which is O, N or S, optionally substituted with one or more Alk$^1$, lower cycloalkyl, lower alkoxy, CO$_2$H, CO$_2$R$^7$, —(Alk$^1$)$_n$—Ar$^1$, cyano or halogen groups;

R$^{14}$ and R$^{15}$ are,
a) independently, hydrogen or —Alk$^2$-H, lower cycloalkyl, lower alkoxy, adamantyl, —(Alk$^1$)$_n$-norbornyl, Ar$^2$, Ar$^3$, —Alk$^1$-substituted independently with one or more SR$^5$, COR$^5$, CONR$^5$R$^7$, NR$^5$COR$^5$, NR$^5$CO$_2$R$^5$, NR$^5$CONHR$^5$, CO$_2$R$^5$, OR$^5$, Ar$^2$or Ar$^3$ groups, —(Alk$^1$)$_n$-fluorenyl, or —(Alk$^1$)$_n$-indanyl; or
b) carbon atoms, optionally substituted with one or more lower alkyl groups, taken together with the linking nitrogen to form a 4 to 8 atom heterocyclic group

wherein;
Her represents —O—, —CH$_2$—, —S(O)$_r$—, —(NH)—or —(N(Alk$^1$))—;

with the proviso that
when Z is (—Alk$^2$-)$_n$COR$^5$, (—Alk$^2$-)$_n$CO$_2$R$^5$or —(Alk$^2$)$_n$-CO-thiopyridyl and R$^5$ is hydrogen, —Alk$^1$—H, lower cycloalkyl, —(Alk$^1$)$_n$—Ar$^1$, adamantyl or when Z is $(-Alk^2-)_n CONR^{14}R^{15}$ and $R^{14}$ and $R^{15}$ are
  (a) independently hydrogen, $-Alk^2$-H, lower cycloalkyl, lower alkoxy, adamantyl, $-Ar^1$, benzyl, diphenylmethyl, triphenylmethyl or $-(Alk^1)_n$-norbornyl; or
  (b) carbon atoms, optionally substituted with one or more lower alkyl groups, taken together with the linking nitrogen to form a 4 to 8 atom heterocylic ring as herein before defined, Y is hydroxy;
  ii) Y is hydrogen and
Z is $OR^5$, $OCOR^5$, $OCONR^{14}R^{15}$, $NR^5COR^5$, $NR^5CO_2R^5$, $NR^5CONR^{14}R^{15}$ or $NR^5CSR^{14}R^{15}$;
  iii) Y and Z taken together are $=O$, $=CH-(Alk^1)_n-COR^5$, $=CH-(Alk^1)_n-CO_2R^5$ or $=CH-(Alk^1)_n-CONR^{14}R^{15}$;

$R^6$ is hydrogen or methyl;

and pharmaceutically acceptable salts thereof.

28. A compound of formula (I):

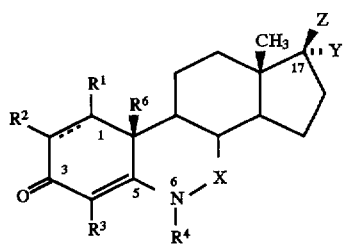

wherein $R^1$ and $R^2$
  i) are independently hydrogen or lower alkyl and the bond between the carbons bearing $R^1$ and $R^2$ is a single or a double bond, or
  ii) taken together are a $-CH_2-$ group forming a cyclopropane ring, and the bond between the carbons bearing $R^1$ and $R^2$ is a single bond; $R^3$ is, hydrogen, $-Alk^1-H$ (optionally substituted with one or more halogens), lower cycloalkyl, lower cycloalkyl-lower alkyl), halogen, $-(Alk^1)_n-CO_2H$, $-(Alk^1)_n-CO_2R^7$, $-(Alk^1)_n-Ar^1$, $-(Alk^1)_n-CONR^8R^9$, $-(Alk^1)_n-NR^8R^9$, $-(Alk^1)_n-S(O)_rR^7$, $-(Alk^1)_n-CN$, $-(Alk^1)-OH$, $-(Alk^1)_n-COR^7$ or $-(Alk^1)_n-OR^7$; wherein $Alk^1$ is lower alkylene, lower alkenylene or lower alkynylene,
n is 0 or 1,
r is 0, 1 or 2,
$R^7$ is $-Alk^1-H$, $-(Alk^1)_n-Ar^1$ or lower cycloalkyl,
$R^8$ and $R^9$ are independently hydrogen, $-Alk^1-H$ or lower cycloalkyl,
$Ar^1$ is a homocyclic aryl group of 6 to 14 carbons;

$R^4$ is, hydrogen, $-Alk^1-H$, lower cycloalkyl, lower cycloalkyl-lower alkyl, $-(Alk^1)_n-S(O)_rR^7$, $-(Alk^1)_n$-phthalimidyl, $-(Alk^1)-CO_2H$, $-(Alk^1)_n-CO_2R^7$, $-(Alk^1)_n-COR^7$, $-(Alk^1)_n-Ar^1$, $-(Alk^1)_n-CONR^8R^9$, $-(Alk^1)_n-NR^8R^9$, $-(Alk^1)_n-OH$ or $-(Alk^1)_n-OR^7$;

X is,

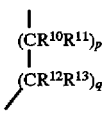

wherein
$R^{10}$, $R^{11}$, $R^{12}$ and $R^{13}$ are independently hydrogen or lower alkyl, p and q are independently either 0 or 1; and, i) Y is hydrogen or hydroxy and
Z is $-(Alk^2)_n-COR^5$, $-(Alk^2)_n-CO_2R^5$, $-(Alk^2)_n-COSR^5$, $-(Alk^2)_n-CONR^{14}R^{15}$, $-(Alk^2)-OCO_2R^5$, $-(Alk^2)-OCOR^5$, $-(Alk^2)-OCONR^{14}R^{15}$, $-(Alk^2)-OR^5$, $-(Alk^2)-NR^5COR^5$, $-(Alk^2)-NR^5CO_2R^5$, $-(Alk^2)-NR^5CONR^{14}R^{15}$, $-(Alk^2)_n-CONR^5NR^{14}R^{15}$, $-(Alk^2)_n-CONR^5CONR^{14}R^{15}$, $-(Alk^2)-NR^5CSNR^{14}R^{15}$ or $-(Alk^2)_n-CONR^5CSNR^{14}R^{15}$; wherein $Alk^2$ is $(C_{1-12})$ alkylene, $(C_{2-12})$ alkenylene or $(C_{2-12})$ alkynylene, $R^5$ and $R^{5'}$ are independently hydrogen, $-Alk^1-H$ (optionally substituted independently with one or more $CO_2H$, $CO_2R^7$, $Ar^2$, $Ar^3$ or cyano groups), $-(Alk^1)_n$-(lower cycloalkyl (optionally substituted independently with one or more $-Alk^1-H$ groups)), adamantyl, norbornyl, $Ar^2$, $Ar^3$, (lower cycloalkyl)-$Ar^2$ or (lower cycloalkyl)-$Ar^3$;

wherein
$Ar^2$ is a homocyclic aromatic group of 6 to 14 carbon ring atoms (optionally substituted independently with one or more $-Alk^2-H$ (optionally substituted independently with one or more halogens), $-(Alk^1)_n-OH$, $-(Alk^1)_n-OR^{16}$, $-(Alk^1)_n-Ar^3$, $-(Alk^1)_n-CO_2H$, $-(Alk^1)_n-CO_2R^7$, $S(O)_rR^7$, $NR^8S(O)_rR^{16}$, $NR^8R^9$, $CONR^8R^9$, lower cycloalkyl, lower alkoxy, $-(Alk^1)_n-Ar^1$, methylenedioxy, ethylenedioxy, morpholino, thiomorpholino, cyano, nitro or halogens); wherein $R^{16}$ is $-Alk^1-H$ (optionally substituted independently with one or more halogens), lower cycloalkyl (optionally substituted independently with one or more halogens, or $-Alk^1-H$ (optionally substituted independently with one or more halogens)) or $-(Alk^1)_n-Ar^1$ (wherein $Ar^1$ is optionally substituted independently with one or more, lower alkoxy, cyano groups, halogens or $-Alk^1-H$ (optionally substituted independently with one or more halogens));

$Ar^3$ is an aromatic group of 5 to 14 ring atoms, at least one of which is O, N or S, (optionally substituted independently with one or more $-Alk^1-H$ (optionally substituted independently with one or more halogens), lower cycloalkyl, lower alkoxy, $CO_2H$, $CO_2R^7$, $-(Alk^1)_n-Ar^1$, cyano or halogen);

$R^{14}$ and $R^{15}$ are,
  a) independently, hydroxy, hydrogen, $-Alk^2-H$, lower cycloalkyl (optionally substituted independently with one or more cyano, $R^{16}$, $Ar^2$, $Ar^3$), lower alkoxy, $-(Alk^1)_n$-adamantyl, $-(Alk^1)_n$-myrantyl, $-(Alk^1)_n$-norbornyl, $-(Alk^1)_n$-fluorenyl, $-(Alk^1)_n$-indanyl, $-Alk^1-H$ (optionally substituted independently with one or more, halogens, cyano, cycloalkyl, $SR^5$, $COR^5$, $CONR^5R^7$, $NR^{5'}COR^5$, $NR^{5'}CO_2R^5$, $NR^{5'}CONHR^5$, $CO_2R^5$, $OR^5$, $Ar^2$ or $Ar^3$), $Ar^2$ or $Ar^3$;

b) alkylene groups (optionally substituted with one or more R⁷ groups, taken together with the linking nitrogen to form a 4 to 8 atom heterocyclic group)

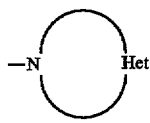

wherein;

Her represents —O—, —CH₂—, —S(O)ᵣ—, —(NH)— or —(N(Alk¹—H))—;

with the proviso that when Z is —(Alk²)ₙ—COR⁵, —(Alk²)ₙ—CO₂R⁵or —(Alk²)ₙ—CO-thiopyridyl and R⁵ is hydrogen, —Alk¹—H, lower cycloalkyl, —(Alk¹)ₙ—Ar¹, adamantyl or when Z is —(Alk²)ₙ—CONR¹⁴R¹⁵ and R¹⁴ and R¹⁵ are a) independently hydrogen, —Alk²-H, lower cycloalkyl, lower alkoxy, adamantyl, —Ar¹, benzyl, diphenylmethyl, triphenylmethyl or —(Alk¹)ₙ-norbornyl; or b) carbon atoms, optionally substituted with one or more lower alkyl groups, taken together with the linking nitrogen to form a 4 to 8 atom heterocyclic ring as herein before defined, Y is hydroxy; or ii) Y is hydrogen and Z is OR⁵, OCOR⁵, OCONR¹⁴R¹⁵, NR⁵'COR⁵'NR⁵'CO₂R⁵, NR⁵CONR¹⁴R¹⁵or NR⁵CSR¹⁴R¹⁵; and iii) Y and Z taken together are =O, =CH—(Alk¹)ₙ—COR⁵, =CH—(Alk¹)ₙ—CO₂R⁵or =CH—(Alk¹)ₙ—CONR¹⁴R¹⁵;

R⁶ is, hydrogen or methyl;

and pharmaceutically acceptable salts thereof.

29. A pharmaceutical composition comprising a compound of formula (I) as defined in claim 1 together with a pharmaceutically acceptable carrier.

30. A method of inhibiting testosterone-5α-reductases comprising contacting testosterone-5α-reductases with a compound of formula (I) as defined in claim 1.

31. A method of treatment of androgen responsive or mediated disease comprising administering an effective amount of a compound of formula (I) as defined in claim 1 to a patient in need thereof in combination.

32. A method of treatment of androgen responsive or mediated disease comprising administering an effective amount of a compound of formula (I) as defined in claim 1 to a patient in need thereof in combination with an antiandrogen.

33. A method of treatment of androgen responsive or mediated disease comprising administering an effective amount of a compound of formula (I) as defined in claim 1 to a patient in need thereof in combination with an alpha 1 adrenergic receptor blocker.

34. A method of treatment of androgen responsive or mediated disease comprising administering an effective amount of a compound of formula (I) as defined in claim 1 to a patient in need thereof in combination with an antiestrogen.

35. A method of treatment as claimed in claim 31 wherein the androgen responsive or mediated disease is benign prostatic hyperplasia, prostatitis, prostate cancer, acne, male pattern baldness and hirsutism.

36. A process for preparing a compound of formula (I) as defined in claim 1 or a pharmaceutically acceptable salt or solvate thereof which comprises (A) reacting a compound of formula (IX)

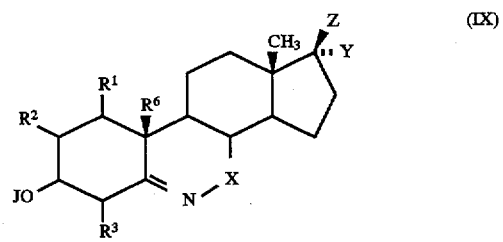

Wherein JO is hydroxy or a protected hydroxygroup, with an oxidismagent.

37. A process as claimed in claim 36 wherein a compound of formula (IX) wherein JO is a protected hydroxy group is deprotected and then oxidised with an appropriate oxidising agent to give a compound of formula (I) where R⁴ is hydrogen.

38. A process as claimed in claim 37 wherein the oxidising agent is Jones reagent.

39. A process as claimed in claim 36 wherein a compound of formula (IX) wherein JO is a protected hydroxy group is treated with an acylating agent, deprotected and then oxidised with an appropriate oxidising agent to give a compound of formula (I) where R⁴ is acyl.

40. A process as claimed in claim 39 wherein the oxidising agent is pyridinium dichromate.

* * * * *